United States Patent
Fryburg et al.

(10) Patent No.: US 6,967,204 B2
(45) Date of Patent: Nov. 22, 2005

(54) TREATMENT OF INSULIN RESISTANCE SYNDROME AND TYPE 2 DIABETES WITH PDE9 INHIBITORS

(75) Inventors: David A. Fryburg, East Lyme, CT (US); Earl Michael Gibbs, Oakdale, CT (US)

(73) Assignee: Pfizer Inc, New York, NY (US)

( * ) Notice: Subject to any disclaimer, the term of this patent is extended or adjusted under 35 U.S.C. 154(b) by 95 days.

(21) Appl. No.: 10/283,814

(22) Filed: Oct. 29, 2002

(65) Prior Publication Data

US 2004/0023989 A1 Feb. 5, 2004

Related U.S. Application Data

(60) Provisional application No. 60/336,981, filed on Nov. 2, 2001.

(51) Int. Cl.[7] ................................................. A61K 31/52
(52) U.S. Cl. .................................................... 514/262.1
(58) Field of Search ....................................... 514/262.1

(56) References Cited

U.S. PATENT DOCUMENTS

| | | | |
|---|---|---|---|
| 4,666,908 A | 5/1987 | Hamilton | 514/229 |
| 5,861,396 A | 1/1999 | Niewohner et al. | 514/234.2 |
| 6,225,456 B1 | 5/2001 | Gu et al. | 536/23.5 |
| 6,255,456 B1 | 7/2001 | Fisher et al. | 530/350 |
| 6,352,985 B1 * | 3/2002 | Yamasaki et al. | 514/227.8 |
| 6,444,816 B1 * | 9/2002 | Das et al. | 544/286 |

FOREIGN PATENT DOCUMENTS

| | | | |
|---|---|---|---|
| EP | 0911333 | 4/2002 | C07D/487/04 |
| WO | WO 0023091 | 4/2000 | A61K/38/00 |
| WO | WO 0213798 | 2/2002 | A61K/31/00 |
| WO | WO 02/102386 A1 | 12/2002 | |

OTHER PUBLICATIONS

Dousa, Kidney International, vol. 55, 1999, pp. 29–62.
Soderling, et al., The Journal of Biological Chemistry, vol. 273, No. 25, Issue of Jun. 19, pp. 15553–15558, 1998.
Etgen, G. J., et al., Diabetes, vol. 46, Issue 11, pp. 1915–1919, 1997, "Nitric Oxide Stimulants Skeletal Muscle Glucose Transport Through a Calcium/Contraction and Phosphatidylinositol–3–Kinase–Independent Pathway".

* cited by examiner

*Primary Examiner*—Kevin E. Weddington
(74) *Attorney, Agent, or Firm*—Peter C. Richardson; Gregg C. Benson; William F. Mulholland

(57) ABSTRACT

This invention is directed to a method of treating insulin resistance syndrome (IRS), hypertension and/or type 2 diabetes in a mammal comprising administering to said mammal a cGMP PDE9 inhibitor or a pharmaceutical composition thereof. This invention is also directed to such methods wherein said cGMP PDE9 inhibitor is used in combination with other agents to treat IRS, hypertension and/or type 2 diabetes.

4 Claims, No Drawings

TREATMENT OF INSULIN RESISTANCE SYNDROME AND TYPE 2 DIABETES WITH PDE9 INHIBITORS

CROSS REFERENCE TO RELATED APPLICATION

This application claims the benefit of U.S. Provisional Application No. 60/336,981 filed Nov. 2, 2001.

FIELD OF THE INVENTION

This invention relates to the use of cGMP PDE9 inhibitors for the treatment of type 2 diabetes, hyperglycemia, dyslipidemia, impaired glucose tolerance, type 1 diabetes and/or insulin resistance syndrome (IRS). This invention also relates to combinations comprising cGMP PDE9 inhibitors and other agents, said combinations being useful in treating type 2 diabetes, hyperglycemia, dyslipidemia, impaired glucose tolerance, type 1 diabetes and/or insulin resistance syndrome.

BACKGROUND OF THE INVENTION

IRS, as defined herein, means the concomitant existence in a subject of two or more of: hyperinsulinemia, dyslipidemia, hypertension, type 2 diabetes or impaired glucose tolerance, hyperuricemia or gout, a pro-coagulant state, atherosclerosis and/or truncal obesity. At the center of IRS, also known as "Syndrome X" and "Metabolic Syndrome" in the biomedical literature, is the common feature of tissue resistance to the action of insulin. This impaired biological response to insulin is manifested in the metabolic and vascular effects of insulin. Although there are monogenic syndromes of insulin resistance (IR), in which a definite gene has been identified as the cause of insulin resistance (such as leprechaunism), these are relatively rare. By contrast, the more common presentation of the IRS is associated with obesity (particularly abdominal) and appears to be polygenic.

The adaptive response to IR in individuals having IRS produces compensatory hyperinsulinaemia. As subjects with IRS become progressively insulin resistant, they manifest varying degrees of change in clinical parameters, including blood pressure, and/or increased levels of serum glucose, and/or cholesterol and/or triglycerides, and/or uric acid, and/or factors that increase coagulation. Once these clinical parameters have changed enough, the patient with IRS may differentially manifest well-recognized clinical conditions or diagnoses.

2. These conditions include: type 2 diabetes, hypertension (high blood pressure), hyperlipidemia or dyslipidemia, particularly (but not limited to) hypertriglyceridemia, hyperuricemia or gout, and hypercoagulability (defined as an abnormal, increased tendency for clots to form, particularly inside blood vessels). These clinical conditions are well-recognized risk factors for cardiovascular (coronary artery and cerebrovascular) disease.

While it is difficult to estimate the prevalence of IRS in the general populace due to both the diversity of the collective risk factors associated with the syndrome and the likelihood that many individuals affected by IRS go undetected because they may exhibit no exterior symptoms and have no prior history of coronary heart disease, it is postulated that at a minimum the patient population at risk for the development of IRS includes individuals with obesity, particularly truncal (abdominal) obesity. Obesity is an extremely common problem in the industrialized world and is associated with the clinical conditions mentioned above. Thus, it is very likely that the prevalence of IRS is very high. Considering this potential patient group alone forms an immense population potentially at risk for the development of complications of IRS. For example in the United States in 1994, 23% of the population aged between 20 and 74 had hypertension, which accounted for 5 deaths per 100,000 population (1997). There will be an estimated 154,392,000 patients with diabetes world-wide in the year 2000. Of these, 15,000,000 will be in the US and 934,000 in the UK. The burden of disease for ischaemic heart disease for both sexes in the WHO region estimated for 1998 was 51,948,000 with a mortality of 7,375,000, constituting 13.7% of total mortality and ranking the highest in the mortality score. The burden of diabetes in both sexes in the WHO region estimated for 1998 was 11,668,000. Thus there exists a large medical need for an effective and safe oral therapy for the treatment of IRS and prevention of the development of IRS and its clinical consequences.

Resistance to the effects of insulin is also observed in the diminished biological response of the endothelium to the vascular effects of insulin. That is, insulin promotes relaxation of blood vessels at least in part through the action of nitric oxide (NO). Nitric oxide generated in the endothelium then stimulates cGMP production in blood vessels and causes them to relax or dilate. This opening of the blood vessel allows more blood to flow, which is particularly important when more blood flow is needed to critical organs, like the heart. It has been demonstrated that there is a decreased release of NO from the endothelium of patients with IR. This decreased release of NO is not only from insulin, but also from other important vasodilators like acetylcholine. This so-called "endothelial dysfunction" contributes to the risk factors for cardiovascular disease which are associated with IRS. The vascular effect of insulin contributes to the effect of insulin to regulate metabolism, particularly, but not necessarily limited to, glucose metabolism.

NO also has direct effects on glucose uptake by skeletal muscle. That is, treatment with a NO-donor substance, such as nitroprusside, or with an analogue of cGMP in vitro increases glucose uptake (transport by GLUT4 glucose transporters). This vasodilation-independent pathway is described in G. J. Etgen, D. A. Fryburg and E. M. Gibbs in *Diabetes*, 46, 1997 pp. 1915–1919, which is incorporated herein by reference. Taken together, NO and cGMP have direct target tissue (skeletal muscle) and vascular actions that influence, mediate, or mimic the action of insulin.

Further effects of impaired NO release by the endothelium include: increases in vascular smooth muscle cell (VSMC) growth, proliferation and migration which are key steps in atherosclerotic plaque formation that can lead to stroke; an increase in platelet aggregation and adhesiveness; an increase of lipid peroxidation and an effect on the inhibition of cell adhesion molecule expression including vascular cell adhesion molecule (VCAM-1), intracellular adhesion molecule (ICAM), E-selectin. Impaired endothelial NO release also impacts on the activity of inflammatory cytokines such as tumour necrosis factor-$\alpha$ (TNF-$\alpha$), and the production of monocyte chemoattractant factor through decreased activity of the transcriptional activator nuclear factor kappa B. These effects on the platelet are also cGMP driven.

Finally, there are examples in which the treatment of factors contributing to IRS (e.g., obesity) or the treatment of IRS itself improves many of these clinical conditions which at first glance appear to be unrelated. For example, dieting alone or pharmacotherapeutic agents that induce weight loss will decrease blood pressure, blood glucose and triglycerides. Agents that are designed to improve insulin sensitivity can also favorably alter blood pressure, lipids, and blood glucose.

Successful diagnosis and treatment of patients with IRS with a PDE9 inhibitor will lead to clinically relevant improvements in blood pressure, and/or serum glucose and/or insulin and/or lipids and/or uric acid, and/or procoagulant factors. This treatment can occur alone or in combination with other therapeutics that improve IRS. Improvement in these clinical conditions should reduce the risk of the development of cardiovascular disease in these patients as well as other complications of these individual disorders (including, but not limited to diabetic neuropathy, nephropathy, and retinopathy).

While IRS has many manifestations, an important underlying mechanistic basis for the condition resides in a resistance to both the vascular and metabolic effects of insulin. It is also understood that the underlying pathology of vascular resistance in insulin resistance syndrome, is a diminished amount of NO produced by the endothelial cells in response to insulin. There is impaired signaling of insulin for glucose uptake in insulin resistant individuals.

Amplification of the cGMP signal, using CGMP PDE9 inhibitors in patients with IRS enhances the insulin glucose uptake signal and improves insulin action at key tissues. Enhancing insulin sensitivity improves clinical parameters of IRS results, inter alia, in:

1. Blood glucose control: In patients with type 2 diabetes or impaired glucose tolerance, an improvement in insulin sensitivity results in a decrease in plasma glucose concentrations (either fasting or after an oral glucose tolerance test or a meal). In a related manner, as regulated by the patient's pathophysiology, there will be an improvement in serum insulin concentrations in either the fasting state or after a glucose load or meal. These improvements in blood glucose control, should the subjects have type 2 diabetes, manifest as improvements in measures of long-term blood glucose control, such as, but not limited to, hemoglobin A1c (glycosylated hemoglobin) or fructosamine.
2. Blood pressure: It is believed that improvement in insulin sensitivity yields improvements in both systolic and diastolic blood pressure.
3. Lipids: Improvement in insulin resistance yields improvements in serum lipids, including, but not limited to, serum cholesterol and triglycerides.
4. Uric Acid: Improvement in insulin resistance yields improvements in serum uric acid.
5. Coagulation Factors: It is believed that improvement in insulin resistance restores normal factors that worsen the procoagulant state.

cGMP PDE 9 inhibitors prevent the effect of the phosphodiesterase 9 enzyme that converts cGMP to inactive GMP thus increasing the amount of accumulated cGMP. This accumulation amplifies the vasodilatory, metabolic, and anti-atherogenic effects of the available nitric oxide and insulin. This amplification action mitigates the adverse effects associated with IRS and improve one or more of the associated conditions.

Diabetes mellitus is characterized by metabolic defects in production and utilization of carbohydrates, resulting in elevated blood glucose or hyperglycemia due to the failure to maintain appropriate blood sugar levels. Research in the treatment of diabetes has centered on attempts to normalize fasting and postprandial blood glucose levels. Current treatments include administration of exogenous insulin, oral administration of drugs and dietary therapies and exercise regimens.

Two major forms of diabetes mellitus are recognized. Type 1 diabetes, or insulin-dependent diabetes, is the result of an absolute deficiency of insulin, the hormone which regulates carbohydrate utilization. Type 2 diabetes, or non-insulin dependent diabetes, often occurs with normal, or even elevated levels of insulin and appears to be the result of the inability of tissues to respond appropriately to insulin. Complications of type 2 diabetes include retinopathy, nephropathy, neuropathy, and coronary heart disease, and are believed to be triggered by excessive protein glycation, which in turn results from excessive levels of circulating glucose. Reduction in hyperglycemia by treatment with a PDE9 inhibitor will lower the level of protein glycation and result in a diminution in these diabetic complications.

Polycystic ovary syndrome (PCOS) also known as Stein-Leventhal syndrome or functional ovarian hyperandrogenism, is a complex endocrine disorder associated with a long-term lack of ovulation (anovulation) and an excess of androgens (male sex hormones, e.g., testosterone) circulating in the blood. The disorder is characterized by the formation of cysts in the ovaries, a process related to the failure of the ovary to release an egg (ovum). In the majority of cases, the ovaries become enlarged. PCOS afflicts up to 22% of women during their childbearing years, although only 10% of these women develop symptoms. It is one of the most frequent causes of infertility in women.

SUMMARY OF THE INVENTION

This invention is directed to a method of treating IRS in a mammal comprising administering to said mammal a cGMP PDE9 inhibitor, a prodrug or solvate thereof or a pharmaceutically acceptable salt of said PDE9 inhibitor, prodrug or solvate. In a preferred embodiment of this invention, said method comprises administering a pharmaceutical composition comprising a cGMP PDE9 inhibitor, a prodrug or solvate thereof or a pharmaceutically acceptable salt of said PDE9 inhibitor, prodrug or solvate. Preferably, said pharmaceutical composition additionally comprises a pharmaceutically acceptable vehicle, diluent or carrier.

This invention is also directed to a method of treating type 2 diabetes in a mammal comprising administering to said mammal a cGMP PDE9 inhibitor, a prodrug or solvate thereof or a pharmaceutically acceptable salt of said PDE9 inhibitor, prodrug or solvate. In a preferred embodiment of this invention, said method comprises administering a pharmaceutical composition comprising a cGMP PDE9 inhibitor, a prodrug or solvate thereof or a pharmaceutically acceptable salt of said PDE9 inhibitor, prodrug or solvate. Preferably, said pharmaceutical composition additionally comprises a pharmaceutically acceptable vehicle, diluent or carrier.

This invention is also directed to a method of treating type 1 diabetes in a mammal comprising administering to said mammal a cGMP PDE9 inhibitor, a prodrug or solvate thereof or a pharmacetically acceptable salt of said cGMP PDE9 inhibitor, prodrug or solvate. In a preferred embodiment of this invention, said method comprises administering a pharmaceutical composition comprising a cGMP PDE9 inhibitor, a prodrug or solvate thereof or a pharmaceutically acceptable salt of said cGMP PDE9 inhibitor, prodrug or solvate. Preferably, said pharmaceutical composition additionally comprises a pharmaceutically acceptable vehicle, diluent or carrier.

This invention is also directed to a method of treating impaired glucose tolerance in a mammal comprising administering to said mammal a cGMP PDE9 inhibitor, a prodrug or solvate thereof or a pharmacetically acceptable salt of said cGMP PDE9 inhibitor, prodrug or solvate. In a preferred embodiment of this invention, said method comprises administering a pharmaceutical composition comprising a cGMP PDE9 inhibitor, a prodrug or solvate thereof or a pharmaceutically acceptable salt of said cGMP PDE9 inhibitor, prodrug or solvate. Preferably, said pharmaceutical composition additionally comprises a pharmaceutically acceptable vehicle, diluent or carrier.

This invention is also directed to a method of treating dyslipidemia such as, but not limited to, hypertriglyceridemia and high LDL cholesterol, in a mammal comprising administering to said mammal a cGMP PDE9 inhibitor, a prodrug or solvate thereof or a pharmacetically acceptable salt of said cGMP PDE9 inhibitor, prodrug or solvate. Dyslipidemia, where used herein, means an alteration of the lipid profile in blood. In a preferred embodiment of this invention, said method comprises administering a pharmaceutical composition comprising a cGMP PDE9 inhibitor, a prodrug or solvate thereof or a pharmaceutically acceptable salt of said cGMP PDE9 inhibitor, prodrug or solvate. Preferably, said pharmaceutical composition additionally comprises a pharmaceutically acceptable vehicle, diluent or carrier.

This invention is also directed to a method of treating polycystic ovary syndrome in a mammal comprising administering to said mammal a cGMP PDE9 inhibitor, a prodrug or solvate thereof or a pharmacetically acceptable salt of said cGMP PDE9 inhibitor, prodrug or solvate. In a preferred embodiment of this invention, said method comprises administering a pharmaceutical composition comprising a cGMP PDE9 inhibitor, a prodrug or solvate thereof or a pharmaceutically acceptable salt of said cGMP PDE9 inhibitor, prodrug or solvate. Preferably, said pharmaceutical composition additionally comprises a pharmaceutically acceptable vehicle, diluent or carrier.

In a further embodiment, this invention is directed to a first combination comprising two active ingredients selected from a cGMP PDE9 inhibitor, a prodrug, solvate or salt thereof and one or more, independently selected, protein kinase inhibitor, prodrug, solvate or salt thereof; an AMP-activated protein kinase activator, prodrug, solvate or salt thereof; a weight loss agent, prodrug, solvate or salt thereof; insulin; a PPAR-γ agonist, prodrug, solvate or salt thereof; a PPAR-γ antagonist, prodrug, solvate or salt thereof, a PPAR-α agonist, prodrug, solvate or salt thereof; a dual PPAR-γ/PPAR-α agonist, prodrug, solvate or salt thereof; a sorbitol dehydrogenase inhibitor, prodrug, solvate or salt thereof; a glycogen phosphorylase inhibitor, prodrug, solvate or salt thereof; a biguamide such as metformin, prodrug, solvate or salt thereof; an HMG-CoA reductase inhibitor, prodrug, solvate or salt thereof; an aldose reductase inhibitor, prodrug, solvate or salt thereof; a PDE5 inhibitor, prodrug, solvate or salt thereof; a PDE11 inhibitor, prodrug, solvate or salt thereof; or a CETP inhibitor, prodrug, solvate or salt thereof. An especially preferred combination is a combination of a cGMP PDE9 inhibitor, a prodrug, solvate or salt thereof and a PDE5 inhibitor, a prodrug, solvate or salt therof. In a further embodiment, the invention is directed to a pharmaceutical composition comprising said first combination and a pharmaceutically acceptable vehicle, carrier or diluent. In a further embodiment, this invention is directed to methods of treating insulin resistance in a mammal comprising administering to said mammal said first combination or a pharmaceutical composition comprising said first combination. In a still further embodiment, this invention is directed to a method of treating type 2 diabetes in a mammal comprising administering to said mammal said first combination or a pharmaceutical composition comprising said first combination.

In a still further embodiment, this invention is directed to a second combination comprising three active ingredients selected from a cGMP PDE9 inhibitor, a prodrug, solvate or salt thereof; a cGMP PDE5 inhibitor, a prodrug, solvate or salt thereof; and a cGMP PDE11 inhibitor, a prodrug, solvate or salt thereof. In a further embodiment, the invention is directed to a pharmaceutical composition comprising said second combination and a pharmaceutically acceptable vehicle, carrier or diluent. In a further embodiment, this invention is directed to methods of treating insulin resistance in a mammal comprising administering to said mammal said second combination or a pharmaceutical composition comprising said second combination. In a still further embodiment, this invention is directed to a method of treating type 2 diabetes in a mammal comprising administering to said mammal said second combination or a pharmaceutical composition comprising said second combination.

This invention is also directed to a kit comprising:
a) a first unit dosage form comprising a cGMP PDE9 inhibitor, a prodrug or solvate thereof or a pharmaceutically acceptable salt of said compound, prodrug or solvate and a pharmaceutically acceptable carrier, vehicle or diluent;
b) a second unit dosage form comprising:
a protein kinase inhibitor;
an AMP-activated protein kinase;
a weight loss agent;
insulin;
a PPAR-γ agonist;
a PPAR-γ antagonist;
a PPAR-α agonist;
a dual PPAR-γ/PPAR-α agonist;
a sorbitol dehydrogenase inhibitor;
a glycogen phosphorylase inhibitor;
a biguamide such as metformin
an HMG-CoA reductase inhibitor;
an aldose reductase inhibitor;
a PDE5 inhibitor;
a PDE11 inhibitor; or
a CETP inhibitor;
a prodrug or solvate of said protein kinase inhibitor, AMP-activated protein, weight loss agent, insulin, PPAR-γ agonist, PPAR-α agonist, PPAR-α antagonist, dual PPAR-γ/PPAR-α agonist, sorbitol dehydrogenase inhibitor, glycogen phosphorylase inhibitor, biguamide, vastatin, aldose reductase inhibitor, PDE5 inhibitor, PDE11 inhibitor or CETP inhibitor; or a pharmaceutically acceptable salt thereof or of said prodrug or solvate and a pharmaceutically acceptable carrier, vehicle or diluent; and
c) a container.
This invention is also directed to a kit comprising:
a) a first unit dosage form comprising a cGMP PDE9 inhibitor, a prodrug or solvate thereof or a pharmaceutically acceptable salt of said compound, prodrug or solvate and a pharmaceutically acceptable carrier, vehicle or diluent;
b) a second unit dosage form comprising a cGMP PDE5 inhibitor, a prodrug or solvate thereof or a pharmaceutically acceptable salt of said compound, prodrug or solvate and a pharmaceutically acceptable carrier, vehicle or diluent;

c) a third unit dosage form comprising a cGMP PDE11 inhibitor, a prodrug or solvate thereof or a pharmaceutically acceptable salt of said compound, prodrug or solvate and a pharmaceutically acceptable carrier, vehicle or diluent; and d) a container.

A further aspect of the invention provides for a method for treating IRS as defined above in a polygenic insulin resistant mammal comprising administering to the mammal an effective amount of a cGMP PDE9 inhibitor or a pharmaceutical composition thereof. It is a further aspect of this invention to treat such polygenic insulin resistant mammals with a combination of a cGMP PDE9 inhibitor and a second compound as defined above, or with a pharmaceutical composition comprising such a combination and a pharmaceutically acceptable vehicle, carrier or diluent. In yet another aspect of this invention, such polygenic insulin resistant mammals are treated with a kit as described above.

The suitability of any particular cGMP PDE9 inhibitor can be readily determined by evaluation of its potency and selectivity using literature methods followed by evaluation of its toxicity, absorption, metabolism, pharmacokinetics, etc in accordance with standard pharmaceutical practice.

Preferably, the cGMP PDE9 inhibitors have an $IC_{50}$ at less than 100 nanomolar, more preferably, at less than 50 nanomolar, more preferably still at less than 15 nanomolar.

IC50 values for the cGMP PDE9 inhibitors may be determined using the PDE9 assay in the Test Methods Section hereinafter.

It is to be understood that the contents of the above published patent applications, and in particular the general formulae and exemplified compounds therein are incorporated herein in their entirety by reference thereto.

A preferred group of cGMP PDE9 inhibitors for use in the methods, compositions, combinations and kits of the instant invention include compounds of the formula (I)

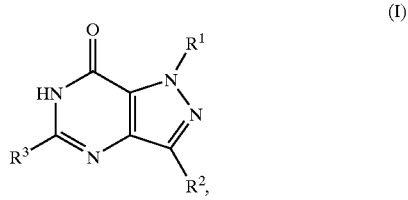

(I)

or a pharmaceutically acceptable salt, solvate or prodrug thereof, wherein:

$R^1$ is H or $(C_1-C_6)$alkyl;

$R^2$ is $(C_1-C_6)$alkyl, straight chain or branched chain, $(C_3-C_7)$cycloalkyl or heteroaryl;

$R^3$ is $(C_1-C_6)$alkyl, straight chain or branched chain, optionally substituted by 1–2 groups each independently selected from Ar, $(C_3-C_7)$cycloalkyl, OAr, SAr, NC(O)$(C_1-C_6)$alkyl, heteroaryl, xanthene, and naphthalene;

Ar is a group of formula

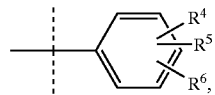

wherein $R^4$, $R^5$ and $R^6$ are each independently selected from H, halo, phenoxy, phenyl, $CF_3$, $OCF_3$, $S(C_1-C_6)$alkyl, $(C_1-C_6)$alkyl, $O(C_1-C_6)$alkyl, said alkyl optionally substituted heteroaryl group or by a phenyl group, wherein said phenyl group is optionally substituted by 1–3 groups selected from halo, $CF_3$, $OCF_3$ and $(C_1-C_6)$alkyl; or wherein $R^4$ and $R^5$ may combine to form a $(C_2-C_3)$alkyl link, wherein said link may optionally incorporate a heteroatom selected from O, S and N; and heteroaryl is aromatic 5–6 membered heterocycle containing 1–3 heteroatoms, each independently selected from O, S and N, said heterocycle optionally substituted by 1–3 substituents, each independently selected from $(C_1-C_6)$alkyl, halo and phenyl, said phenyl optionally substituted by 1–3 groups selected from halo and $(C_1-C_6)$alkyl;

with the proviso that when $R^1$ is —$CH_3$, $R^2$ cannot be —$CH_2CH_2CH_3$.

A particularly preferred group of compounds within the preferred group are those compounds wherein $R^1$ is H or $CH_3$. More preferably $R^1$ is H.

Another particularly preferred group of compounds within the preferred group are those compounds wherein $R^2$ is selected from $(C_3-C_4)$alkyl, cyclopentyl and pyridinyl. More preferably $R^2$ is 3-pyridinyl.

Another particularly preferred group of compounds within the preferred group are those compounds wherein $R^3$ is $(C_1-C_3)$alkyl, optionally substituted by 1–2 groups selected from: Ar, $(C_3-C_7)$cycloalkyl and heteroaryl. More preferably $R^3$ is $(C_1-C_3)$alkyl, optionally substituted by Ar. Most preferably $R^3$ is $C_1$ alkyl substituted by Ar, where $R^4$, $R^5$ and $R^6$ are each H.

Another particularly preferred group of compounds within the preferred group are those compounds wherein $R^4$, $R^5$ and $R^6$ are each independently selected from:

H, halo, phenoxy, phenyl, $CF_3$, $OCF_3$, $S(C_1-C_6)$alkyl, $(C_1-C_6)$alkyl, $O(C_1-C_6)$alkyl, said alkyl optionally substituted by a heteroaryl group or by a phenyl group, wherein said phenyl group is optionally substituted by 1–3 groups selected from halo, $CF_3$, $OCF_3$ and $(C_1-C_6)$alkyl; or wherein $R^4$ and $R^5$ may combine to form a $C_2$ alkyl link, said link incorporating an O atom. More preferably $R^4$, $R^5$ and $R^6$ are each independently selected from H, halo, $OCF_3$, $CF_3$, OAr, and $O(C_1-C_6)$alkyl optionally substituted by phenyl, optionally substituted by H, halo, phenoxy, phenyl, $CF_3$, $OCF_3$, $S(C_1-C_6)$alkyl, $(C_1-C_6)$alkyl, $O(C_1-C_6)$alkyl, said alkyl optionally substituted by a heteroaryl group or by a phenyl group, wherein said phenyl group is optionally substituted by H, halo, $CF_3$, $OCF_3$ and $(C_1-C_6)$alkyl. Yet more preferably $R^4$, $R^5$ and $R^6$ are each independently selected from Cl, H, $OCF_3$, $CF_3$ and $O(C_1-C_6)$ alkyl substituted by phenyl. Most preferably, $R^4$, $R^5$ and $R^6$ are each independently selected from H, Cl and $O(C_1-C_3)$alkyl substituted by phenyl.

Another particularly preferred group of compounds within the preferred group are those compounds wherein heteroaryl is an aromatic 5–6 membered heterocycle containing at least 2 nitrogen atoms, said heterocycle optionally substituted by 1–3 substituents, each independently selected from $(C_1-C_6)$alkyl, halo and phenyl, said phenyl optionally substituted by 1–3 groups selected from halo and $(C_1-C_6)$ alkyl. More preferably heteroaryl is an aromatic 5 membered heterocycle containing at least 2 nitrogen atoms, said heterocycle optionally substituted by 1 substituent, each independently selected from $(C_1-C_6)$alkyl, halo and phenyl, said phenyl optionally substituted by 1–3 groups selected from halo and $(C_1-C_6)$alkyl. Yet more preferably heteroaryl is an aromatic 5 membered heterocycle containing at least 2 nitrogen atoms, said heterocycle optionally substituted by phenyl optionally substituted by halo. Most preferably heteroaryl is an imidazole or an oxadiazole.

An especially preferred cGMP PDE9 inhibitor is 5-(3-chloro-benzyl)-3-isopropyl-1,6-dihydro-pyrazolo[4,3-d]pyrimidin-7-one, a prodrug thereof or a pharmaceutically acceptable salt thereof or of said prodrug.

According to a further aspect the present invention additionally provides for the use of a PDE9 inhibitor or a pharmaceutical composition thereof for the treatment of the insulin resistance syndrome in a subject having type 2 diabetes mellitus or impaired glucose tolerance or having a family history of diabetes and at least one of the following conditions: dyslipidemia, hypertension, hyperuricemia, a pro-coagulant state, atherosclerosis or truncal obesity.

According to a further aspect the present invention additionally provides a method of elevating intracellular cGMP in a mammal in need thereof comprising administering to said mammal a PDE9 inhibitor, a prodrug thereof, a pharmaceutically acceptable salt of said PDE9 inhibitor or of said prodrug, or a pharmaceutical composition comprising a PDE9 inhibitor. It is particularly preferred that type 2 diabetes, insulin resistance syndrome or hypertension is treated thereby.

According to a further aspect the invention additionally provides a method of treating hypertension in a mammal comprising administering to said mammal a PDE9 inhibitor, a prodrug thereof or a pharmaceutically acceptable salt of said PDE9 inhibitor or of said prodrug. It is particularly preferred that said PDE9 inhibitor is 5-(3-chloro-benzyl)-3-isopropyl-1,6-dihydro-pyrazolo[4,3-d]pyrimidin-7-one, a prod rug thereof or a pharmaceutically acceptable salt thereof or of said prodrug.

DETAILED DESCRIPTION OF THE INVENTION

The PDE9 inhibitors used in the pharmaceutical compositions and methods of this invention may be prepared as set forth in the Examples provided below or by following procedures analogous to those set forth in U.S. Pat. No. 6,235,742 B1, which is incorporated herein by reference.

The pharmaceutically acceptable salts of the cGMP PDE9 inhibitor compounds as disclosed herein for use in the treatment of the insulin resistance syndrome in accordance with the present invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. The cGMP PDE9 inhibitor compounds for use in the present invention can also provide pharmaceutically acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. Pharm, Sci., 66, 1–19, 1977.

The cGMP PDE9 inhibitor compounds suitable for use in accordance with the present invention, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the cGMP PDE9 inhibitor compounds suitable for use in accordance with the present invention or salts or solvates thereof can be administered orally, buccally or sublingually in the form of tablets, capsules (including soft gel capsules), multi-particulate, gels, films, ovules, elixirs, solutions or suspensions, which may contain flavouring or colouring agents, for immediate-, delayed-, modified-, sustained-, dual-, controlled-release or pulsatile delivery applications. Such compounds may also be administered via fast dispersing or fast dissolving dosages forms or in the form of a high energy dispersion or as coated particles. Suitable pharmaceutical formulations may be in coated or un-coated form as desired.

Such solid pharmaceutical compositions, for example, tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), hydroxypropyl methylcellulose acetate succinate (HPMCAS), sucrose, gelatin and acacia. Additionally, lubricating agents such as magnesium stearate, stearic acid, glyceryl behenate and talc may be included.

Solid compositions of a similar type may also be employed as fillers in gelatin capsules or HPMC capsules. Preferred excipients in this regard include lactose, starch, a cellulose, milk sugar or high molecular weight polyethylene glycols. For aqueous suspensions and/or elixirs, the cGMP PDE9 inhibitor compounds may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, HPMC, HPMCAS, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form, i.e., upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The cGMP PDE9 inhibitor compounds suitable for use in accordance with the present invention can also be administered parenterally, for example, intracavernosally, intravenously, intra-arterially, intraperitoneally, intrathecally, intraventricularly, intraurethrally, intrasternally, intracranially, intramuscularly or subcutaneously, or they may be administered by infusion or needle-free techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the cGMP PDE9 inhibitor compounds for use in the present invention or salts or solvates thereof will usually be from 1 to 500 mg (in single or divided doses). A preferred dosage range is about 1 mg to about 100 mg. For the treatment of IRS the dosage may by via single dose, divided daily dose, multiple daily dose, continuous (chronic) daily dosing for a specified period which may be from one to five or 5 or more, such as up to 10 or more days. Alternatively the treatment of IRS may be affected by continuous dosing, such as for example, via a controlled release dosage form wherein such continuous dosage form can be administered on a daily basis for a number of days or wherein such continuous dosing can be affected via a slow-release formulation which doses for more than one day at a time.

Thus, for example, tablets or capsules of the cGMP PDE9 inhibitor compounds suitable for use in accordance with the present invention or salts or solvates thereof may contain from 1 mg to 250 mg of active compound for administration singly or two or more at a time, as appropriate. Preferred tablets or capsules will contain about 1 mg to about 50 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The cGMP PDE9 inhibitor compounds suitable for use in accordance with the present invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The cGMP PDE9 inhibitor compounds suitable for use in accordance with the present invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the cGMP PDE9 inhibitor compounds suitable for use in accordance with the present invention or salts or solvates thereof can be administered in the form of a suppository or pessary, or they may be applied topically in the form of a gel, hydrogel, lotion, solution, cream, ointment or dusting powder. The cGMP PDE9 inhibitor compounds suitable for use in accordance with the present invention or salts or solvates thereof may also be dermally or transdermally administered, for example, by the use of a skin patch. They may also be administered by the pulmonary or rectal routes.

The compounds may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the cGMP PDE9 inhibitor compounds suitable for use in accordance with the present invention or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The cGMP PDE9 inhibitor compounds suitable for use in accordance with the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in International Patent Application Publication Nos. WO91/11172, WO94/02518 and WO98/55148.

Generally, in humans, oral administration is the preferred route, being the most convenient. In circumstances where the recipient suffers from a swallowing disorder or from impairment of drug absorption after oral administration, the drug may be administered parenterally, sublingually or buccally.

For veterinary use, a compound, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

It is to be appreciated that all references herein to treatment include curative, palliative and prophylactic treatment.

The present invention additionally comprises the use of a combination of a first and a second compound for the treatment of the insulin resistance syndrome or type 2 diabetes. The first compound of the combination is a cGMP PDE9 inhibitor compound as defined herein. The second compound of the combination is a naturally occurring or synthetic prostaglandin or ester thereof; an α-adrenergic receptor antagonist compound (also known as α-adrenoreceptors, α-receptors or α-blockers); a nitric oxide donor (also known as NO-donor or NO-agonist); a potassium channel opener or potassium channel modulator; a dopaminergic agent; a vasodilator agent; a thromboxane A2 agonist; an ergot alkaloid; a compound which modulates the action of a naturetic factor, particularly a compound which modulates the action of atrial naturetic factor (also known as atrial naturetic peptide), B type and C type naturetic factors; an angiotensin receptor antagonist; a substrate for NO-synthase; a calcium channel blocker; an antagonist of endothelin receptors; an inhibitor of endothelin converting enzyme; a cholesterol lowering agent such as an HMG-CoA reductase inhibitor; an antiplatelet or antithrombotic agent; an insulin sensitizing agent such as a glitazone; an insulin secretagogue such as a sulfonylurea; an acetylcholinesterase inhibitor; an estrogen receptor modulator; a PDE5 inhibitor; a PDE11 inhibitor; a neuropeptide Y (NPY) inhibitor, preferably an NPY5 inhibitor and even more preferably an NPY1 inhibitor, said NPY inhibitor having an IC50 of less than 100 nM, and more preferably an IC50 of less than 50 nM; a vasoactive intestinal protein (VIP) or a VIP mimetic, more particularly a VIP which is mediated by one or more of the VIP receptor subtypes VPAC1, VPAC or PACAP (pituitary adenylate cyclase activating peptide); a VIP receptor agonist; a VIP analogue or fragment; an α-adrenoreceptor antagonist/VIP combination (e.g., Invicorp®, Aviptadil); a serotonin receptor agonist, antagonist or modulator, more particularly, a modulator for 5HT1A; a testosterone replacement agent; estrogen; a combination of estrogen and medroxyprogesterone; a combination of estrogen and medroxyprogesterone acetate (MPA); a combination of estrogen and a methyl testosterone hormone replacement therapy agent (e.g., HRT); a modulator of transporters for noradrenaline, dopamine or serotonin; a purinergic receptor agonist or modulator; a neurokinin (NK) receptor antagonist; an opioid receptor agonist, antagonist or modulator, preferably an agonist for the ORL-1 receptor; an oxtocin/vasopressin receptor modulator or agonist, preferably a selective oxytocin agonist or modulator; a cannabinoid receptor modulator; a central nervous system (CNS) active agent; an angiotensin-converting enzyme inhibitor; a combinatino of an angiotensin converting-enzyme inhibitor and a neutral endopeptidase; L-Dopa; a combination of L-Dopa and carbidopa; a steroidal anti-inflammatory agent; a non-steroidal anti-inflammatory agent; a proten kinase C-β inhibitor; an AMP-activated protein kinase activator; insulin; a weight loss agent; a dipeptidyl peptidase IV (DPP IV) inhibitor; a glucagon antagonist; an I kappa B kinase-β (IKK-β) inhibitor such as salicylate; a PTP1B inhibitor; an agent that reduces the levels of PTP1B levels using antisense technology; a glycogen synthase kinase-3 inhibitor; a GLP-1 agonist; a PPAR-γ agonist; a PPAR-γ antagonist; a PPAR-α agonist; a dual PPAR-α/PPAR-γ agonist; a RXR antagonist; a biguamide such as metformin, a glycogen phosphorylase inhibitor; a sorbitol dehydrogenase inhibitor (SDI); an aldose reductase inhibitor (ARI); a soluble guanylate cyclase (sGC) activator; growth hormone; or a growth hormone secretagogue.

Any naturally occurring or synthetic prostaglandin or ester thereof may be used as the second compound of a combination of this invention. Suitable prostaglandins for use herein include alprostadil, prostaglandin $E_1$, prostaglandin $E_0$, 13, 14-dihydroprosta glandin $E_1$, prostaglandin $E_2$, eprostinol, natural synthetic and semi-synthetic prostaglandins and derivatives thereof including those described in International Patent Application Publication No. WO00/33825 and U.S. Pat. No. 6,037,346; $PGE_0$, $PGE_1$, $PGA_1$, $PGB_1$, $PGF_1\alpha$, 19-hydroxy $PGA_1$, 19-hydroxy—$PGB_1$, $PGE_2$, $PGB_2$, 19-hydroxy-$PGA_2$, 19-hydroxy-$PGB_2$, $PGE_3\alpha$, carboprost tromethamine dinoprost, tromethamine, dinoprostone, lipoprost, gemeprost, metenoprost, sulprostune, tiaprost and moxisylate.

The disclosures made in U.S. patents, International patent applications and all other references mentioned herein are hereby incorporated by reference.

Any α-adrenergic receptor antagonist compound may be used as the second compound of a combination of this invention. Suitable α-adrenergic receptor antagonists for use herein include the α-adrenergic receptor blockers described in International Patent Application Publication No. WO99/30697. Selective $\alpha_1$-adrenoceptor, $\alpha_2$-adrenoceptor blockers and non-selective adrenoceptor blockers may also be used as the second α-adrenergic receptor antagonist compound of this invention. Suitable α-adrenoceptor blockers include phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin. Suitable $\alpha_2$-adrenoceptor blockers include those disclosed in U.S. Pat. No. 6,037,346, dibenamine, tolazoline, trimazosin and dibenamine. Suitable α-adrenergic receptors for use as the second compound of a combination of this invention are also described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000. Other suitable $\alpha_2$-adrenoceptor blockers include clonidine, papaverine, papaverine hydrochloride, each of which may optionally be administered in the presence of a cariotonic agent such as, but not limited to, pirxamine.

Any nitric oxide donor (NO-donor or NO-agonist) compound may be used as the second compound of a combination of this invention. Suitable NO-donor compounds for use herein include organic nitrates, such as mono-, di- or tri-nitrates; organic nitrate esters such as glyceryl binitrate (also known as nitroglycerin), isosorbide 5-mononitrate, isosorbide dinitrate, pentaerythritol tetranitrate, erythrityl tetranitrate, amylnitrate, a diazenium diolate (NONOate), and 1,5-pentanedinitrate; sodium nitroprusside (SNP); 3-morpholinosydnonimine molsidomine; S-nitroso-N-acetyl penicilliamine (SNAP); S-nitroso-N-glutathione (SNO-GLU); N-hydroxy-L-arginine; linsidomine; linsidomine chlorohydrate; (SIN-1) S-nitroso-N-cysteine; L-arginine; ginseng; zizphi fructus; molsidomine; Re-2047; and nitrosylated maxisylyte derivatives such as NMI-678–11 and NMI-937 (International Patent Application Publication No. WO00/12075).

Any potassium channel opener or modulator may be used as the second compound of a combination of this invention. Suitable potassium channel openers/modulators for use herein include nicorandil, cromokalim, levcromakalim, lemakalim, pinacidil, cliazoxide, minoxidil, charybdotoxin, glyburide, glipizide, 4-aminipyridine and barium chloride ($BaCl_2$).

Any dopaminergic agent may be used as the second compound of a combination of this invention. Preferred dopaminergic agents include apomorphine and selective D2, D3 and D2/$D_3$agonists such as pramipexole, ropirinol (International Patent Application Publication No. WO00/23056), L-Dopa, L-Dopa in combination with carbidopa, PNU95666 (International Patent Application Publication No. WO00/40226).

Any vasodilator agent may be used as the second compound of a combination of this invention. Suitable vasodilator agents for use herein include nimodepine, pinacidil, cyclandelate, isoxsuprine, chloroprumazine, haloperidol, Rec 15/2739 and trazodone.

Any ergot alkoloid may be used as the second compound of a combination of this invention. Suitable ergot alkaloids include those disclosed in U.S. Pat. No. 6,037,346; acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride.

Any angiotensin receptor antagonist may be used as the second compound of a combination of this invention. Suitable angiotensin receptor antagonists include losartan, candersartan, eprosartan, irbesartan and valsartan.

Any substrate for NO-synthase may be used as the second compound of a combination of this invention. Suitable NO-synthase substrates include, inter alia, L-arginine.

Any calcium channel blocker may be used as the second compound of a combination of this invention. Suitable calcium channel blockers include, amlodipine (amlodipine besylate is also known as Norvasc®), bepridil, which may be prepared as disclosed in U.S. Pat. No. 3,962,238 or U.S. Reissue No. 30,577; clentiazem, which may be prepared as disclosed in U.S. Pat. No. 4,567,175; diltiazem, which may be prepared as disclosed in U.S. Pat. No. 3,562, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572,909; bamidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578.

Any one cholesterol lowering agent may be used as the second compound of a combination of this invention. Suitable cholesterol lowering agents include vastatins such as simvastatin, disclosed in U.S. Pat. No. 4,444,784; pravastatin, disclosed in U.S. Pat. No. 4,346,227; cerivastatin, disclosed in U.S. Pat. No. 5,502,199; mevastatin, disclosed in U.S. Pat. No. 3,983,140; velostatin, disclosed in U.S. Pat. Nos. 4,448,784 and 4,450,171; fluvastatin, disclosed in U.S. Pat. No. 4,739,073; compactin, disclosed in U.S. Pat. No. 4,804,770; lovastatin, disclosed in U.S. Pat. No. 4,231,938; dalvastatin, disclosed in European Patent Application Publication No. 738510 A2; fluindostatin, disclosed in European Patent Application Publication No. 363934 A1; atorvastatin, disclosed in U.S. Pat. No. 4,681,893; atorvastatin calcium (atorvastatin calcium is also known as Lipitor®), disclosed in U.S. Pat. No. 5,273,995; and dihydrocompactin, disclosed in U.S. Pat. No. 4,450,171. Other suitable cholesterol lowering agents include fibrates.

Any antiplatelet and antithrombotic agent may be used as the second compound of a combination of this invention. Suitable antiplatelet and antithrombotic agents include, e.g., tPA, uPA, warfarin, hirudin and other thrombin inhibitors, heparin and thromboplastin activating factor inhibitors.

Any insulin sensitising agent may be used as the second compound of a combination of this invention. Suitable insulin sensitizing agents include Avandia®, Actos® and hypoglycaemic agents such as, but not limited to, sulfonylureas such as glipizide, metformin and acarbose.

Any acetylcholinesterase inhibitor may be used as the second compound of a combination of this invention. A suitable acetylcholinesterase inhibitor is, e.g., donezipil.

Any estrogen receptor modulator, estrogen agonist or estrogen antagonist may be used as the second compound of a combination of this invention. Suitable estrogen receptor modulators, estrogen agonists or estrogen antagonists include the compounds disclosed in International Patent Application Publication No. WO96/21656 and U.S. Pat. No. 5,552,412. Preferred such compounds include raloxifene, lasofoxifene, (–)-cis-6-phenyl-5-[4-(2-pyrrolidin-1-yl-ethoxy)-phenyl]-5,6,7,8-tetrahydronaphthalene-2-ol and pharmaceutically acceptable salts thereof.

Any PDE5 or PDE11 inhibitor may be used as the second compound of a combination of this invention. It is particularly preferred that a PDE5 inhibitor be used as the second compound of this invention. Suitable PDE5 inhibitors include the pyrazolo [4,3-d]pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in International Patent Application Publication No. WO93/07149; the quinazolin-4-ones disclosed in International Patent Application Publication No. WO93/12095; the pyrido [3,2-d]pyrimidin-4-ones disclosed in International Patent Application Publication No. WO94/05661; the purin-6-ones disclosed in International Patent Application Publication No. WO94/00453; the pyrazolo [4,3-d]pyrimidin-7-ones disclosed in International Patent Application Publication No. WO98/49166; the pyrazolo [4,3-d]pyrimidin-7-ones disclosed in International Patent Application Publication No. WO99/54333; the pyrazolo [4,3-d]pyrimidin-4-ones disclosed in EP-A-0995751; the pyrazolo [4,3-d]pyrimidin-7-ones disclosed in International Patent Application Publication No. WO00/24745; the pyrazolo [4,3-d]pyrimidin-4-ones disclosed in EP-A-0995750; the compounds disclosed in International Patent Application Publication No. WO95/19978; the compounds disclosed in International Patent Application Publication No. WO99/24433; he pyrazolo [4,3-d]pyrimidin-7-ones disclosed in International Patent Application Publication No. WO01/27112; the pyrazolo [4,3-d]pyrimidin-7-ones disclosed in International Patent Application Publication No. WO01/27113; the compounds disclosed in EP-A-1092718; the compounds disclosed in EP-A-1092719; and the compounds disclosed in International Patent Application Publication No. WO93/07124.

Preferred PDE5 inhibitors for use as a second compound in a combination of this invention include: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl ]-2-(pyridin-2-yl)methyl-2,6-dihydro-7H-pyrazolo[4,3-d]pyrimidin-7-one (see WO99/54333); 6-benzo[1,3]dioxol-5-yl-2-methyl-2,3,6,7,12,12a-hexahydro-pyrazino[1',2':1,6]pyrido[3,4-b]indole-1,4-dione (cialis); (+)-3-ethyl-5-[5-(4-ethylpiperazin-1-ylsulphonyl)-2-(2-methoxy-1 (R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo [4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-(2-methoxyethyl)-7--oxo-2H-pyrazolo[4,3-d]pyrimidin-5-yl]-3-pyridylsulphonyl}-4-ethylpiperazine (see WO01/27113, Example 8); 5-[2-iso-butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO01/27113, Example 15); 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO01/27113, Example 66); 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one (see WO1/27112, Example 124); 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one (see WO01/27112, Example 132); (6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), i.e. the compound of examples 78 and 95 of published international application WO95/19978, as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5, 1-f ][1,2,4]triazin-4-one (vardenafil) also known as 1-[[3-(3,4-dihydro-5-methyl-4-oxo-7-propylimidazo [5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 in WO93/07124 (EISAI); and compounds 3 and 14 from Rotella D P, *J. Med. Chem.*, 2000, 43, 1257.

Still other type cGMP PDE5 inhibitors useful in conjunction with the present invention include: 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2, 1-b]purin-4(3H)one; furaziocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophe propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866; selected from: sildenafil, 5-(2-ethoxy-5-morpholinoacetylphenyl)-1-ethyl-3-n-propyl-1,6-dihydro-7H-pyrazolo[4,3-d]pyrimidin-7-one, 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one, 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-(2-methoxyethyl)-2,6-dihydro-7H-pyrazolo[4,3-d]pyrimidin-7-one and 1-[[3-(3,4-dihydro-5-methyl-4-oxo-7-propylimidazolo[5, 1-f]-as-trizin-2-yl)-4-ethoxyphenyl]sulphonyl]-4-ethylpiperzine or a pharmaceutically acceptable salt, solvate, pro-drug or polymorph thereof.

More preferred cGMP PDE5 inhibitors for use as the second compound in a combination of this invention include sildenafil, sildenafil citrate (also known as Viagra®; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); 6-benzo[1,3]dioxol-5-yl-2-methyl -2,3,6,7,12,12a-hexahydro-pyrazino[1',2':1,6]pyrido[3,4-b]indole-1,4-dione (cialis); and 5-[2-ethoxy-5-(4-ethylpiperazin-1-ylsulphonyl)pyridin-3-yl]-3-ethyl-1-(2-methoxyethyl)-1,6-dihydro-7H-pyrazolo[4,3-d]pyrimidin-7-one.

Any melanocortin receptor agonist, melanocortin receptor modulator or melanocortin receptor enhancer may be used as the second compound of a combination of this invention. Suitable melanocortin receptor agonists, modulators or enhancers include melanotan II; PT-14; PT-141; and compounds disclosed in International Patent Application Publication Nos. WO99/64002, WO00/74679, WO99/55679, WO01/05401, WO00/58361, WO01/14879, WO01/13112 and WO99/54358.

Any serotonin receptor agonist, antagonist or modulator may be used as the second compound in a combination of this invention. It is particularly preferred to use agonists, antagonists or modulators of 5HT1A. Suitable such agonists, antagonists or modulators include VML 670; 5HT2A; 5HT2C; 5HT3; and 5HT6 receptors, including those described in International Patent Application Publication Nos. WO99/02159, WO00/02550 and WO00/28993.

Any testosterone replacement agent may be used as the second compound in a combination of this invention. Suitable testosterone replacement agents include dehydroandrostendione, testosternone (Tostrelle), dihydrotestosterone and testosterone implants.

Any hormone replacement therapy (HRT) agent may be used as the second compound of a combination of this invention. Suitable HRT agents include Premarin®, Cenestin®, Oestrofeminal®, Equin®, Estrace®, Estrofem®, Elleste Solo®, Estring®, Eastraderm TTS®, Eastraderm Matrix®, Dermestril®, Premphase®, Preempro®, Prempak®, Premique®, Estratest®, Estratest HS® and Livial® (tibolone).

Any modulator of transporters for noradrenaline, dopamine and/or serotonin may be used as the second compound of a combination of this invention. Suitable such modulators include bupropion and GW-320659.

Any neurokinin (NK) receptor antagonist may be used as the second compound of a combination of this invention. Suitable NK receptor antagonists include those described in International Patent Application Publication No. WO99/64008.

Any angiotensin converting enzyme inhibitor (ACE inhibitor) may be used as the second compound of a combination of this invention. Suitable ACE inhibitors include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,452,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361.

Any compound which is a combined inhibitor of angiotensin-converting enzyme and neutral endopeptidase may be used as the second compound of a combination of this invention. A suitable such combined inhibitor is, e.g., omapatrilat.

Any protein kinase C-$\beta$ inhibitor may be used as the second compound of a combination of this invention. A suitable protein kinase C-$\beta$ inhibitor is, e.g., LY333531.

Any activator of AMP-activated protein kinase may be used as the second compound of a combination of this invention. A suitable such activator is, e.g., 5-amino-4-imidazolecarboxamide ribonucleoside.

Any weight loss agent may be used as the second compound of a combination of this invention. Suitable weight loss agents include sibutramine and orlistat.

Any dipeptidyl peptidase IV (DPPIV) inhibitor may be used as the second compound of a combination of this invention. Suitable DPPIV inhibitors include NVP DPP728 and P32/98.

Any glucagon antagonist may be used as the second compound of a combination of this invention. A suitable glucagon antagonist is, e.g., NNC25-2504.

Any IKK-$\beta$ inhibitor may be used as the second compound of a combination of this invention. A suitable IKK-$\beta$ inhibitor is, e.g., salicylate.

Any PTP1B inhibitor may be used as the second compound of a combination of this invention. A suitable PTP1B inhibitor is, e.g., PTP112.

Any glycogen synthase kinase-3 (GSK-3) inhibitor may be used as the second compound of a combination of this invention. A suitable GSK-3 inhibitor is, e.g., Chir98014

Any GLP-1 agonist may be used as the second compound of a combination of this invention. Suitable GLP-1 agonists include GLP1, NN-2211 and exendin 4.

Any PPAR-$\gamma$ agonist may be used as the second compound of a combination of this invention. Suitable PPAR-$\gamma$ agonists include Rezulin®, Avandia®, Actos® or CS011.

Any PPAR-$\gamma$ antagonist may be used as the second compound of a combination of this invention. A suitable PPAR-$\gamma$ antagonist is, e.g., bisphenol A diglycidyl ether (BADGE).

Any PPAR-$\alpha$ agonist may be used as the second compound of a combination of this invention. A suitable PPAR-$\alpha$ agonist is, e.g., fenofibrate.

Any dual PPAR-$\alpha$/PPAR-$\gamma$ agonist may be used as the second compound of a combination of this invention. Suitable such dual agonists include farglitazar, GW1929, DRF2725, AZ242 and KRP 297.

Any RXR antagonist may be used as the second compound of a combination of this invention. A suitable RXR antagonist is, e.g., HX531.

Any glycogen phosphorylase inhibitor may be used as the second compound of a combination of this invention. A suitable glycogen phosphorylase inhibitor is, e.g., CP-316819.

Any sorbitol dehydrogenase inhibitor (SDI) may be used as the second compound of a combination of this invention. Suitable SDIs include those dislcosed in International Patent Application Publication No. WO00/59510. A particuarly preferred SDI is 1R-(4-(4-(4,6-dimethyl)-[1,3,5]triazin-2-yl)-2R,6S-dimethyl-piperazin-1-yl)-pyrimidin-2-yl)-ethanol.

Any aldose reductase inhibitor (ARI) may be used as the second compound of a combination of this invention. Suitable ARIs include zopolrestat, epalrestat, ponalrestat, zenarestat or fidarestat.

Other suitable ARIs for use as the second compound in a combination of this invention include compounds of the Formula ARI

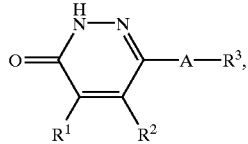

ARI 5 prodrugs thereof and pharmaceutically acceptable salts of said compounds and said prodrugs, wherein:

A is S, SO or $SO_2$;

$R^1$ and $R^2$ are each independently hydrogen or methyl;

$R^3$ is $Het^1$, —$CHR^4Het^1$ or $NR^6R^7$;

$R^4$ is hydrogen or $(C_1-C_3)$alkyl;

$R^6$ is $(C_1-C_6)$alkyl, aryl or $Het^2$;

$R^7$ is $Het^3$;

$Het^1$ is pyridyl, pyrimidyl, pyrazinyl, pyridazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; $Het^1$ is optionally substituted with up to a total of four substituents each independently selected from halo, formyl, $(C_1-C_6)$alkoxycarbonyl, $(C_1-C_6)$alkylenyloxycarbonyl, $(C_1-C_4)$alkoxy-$(C_1-C_4)$alkyl, $C(OH)R^{12}R^{13}$, $(C_1-C_4)$alkylcarbonylamido, $(C_3-C_7)$cycloalkylcarbonylamido, phenylcarbonylamido, benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$cycloalkyl, $(C_1-C_6)$alkyl optionally substituted with up to three fluoro, or $(C_1-C_4)$alkoxy optionally substituted with up to five fluoro; said benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for $Het^1$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_6)$alkylsulfenyl $(C_1-C_6)$alkylsulfinyl, $(C_1-C_6)$alkylsulfonyl, $(C_1-C_6)$alkyl optionally substituted with up to five fluoro and $(C_1-C_6)$alkoxy optionally substituted with up to five fluoro; said imidazolyl, oxazolyl, isoxazolyl, thiazolyl and pyrazolyl in the definition of substituents for $Het^1$ are optionally substituted with up to two substituents independently selected from hydroxy, halo, $C_1-C_6)$alkyl, hydroxy-$(C_1-C_4)$alkyl, $(C_1-C_4)$alkoxy-$(C_1-C_4)$alkyl, $C_1-C_4$-alkyl-phenyl optionally substituted in the phenyl portion with one Cl, Br, OMe, Me or $SO_2$-phenyl wherein said $SO_2$-phenyl is optionally substituted in the phenyl portion with one Cl, Br, OMe, Me, $(C_1-C_4)$alkyl optionally substituted with up to five fluoro, or $(C_1-C_4)$alkoxy optionally substituted with up to three fluoro;

$R^{12}$ and $R^{13}$ are each independently hydrogen or $(C_1-C_4)$alkyl;

$Het^2$ and $Het^3$ are each independently imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy; $Het^2$ and $Het^3$ are each independently optionally substituted with up to a total of four substituents each independently selected from halo, formyl, $(C_1-C_6)$alkoxycarbonyl, $(C_1-C_6)$alkylenyloxycarbonyl, $(C_1-C_4)$alkoxy-$(C_1-C_4)$alkyl, $C(OH)R^1R^{19}$, $(C_1-C_4)$alkylcarbonylamido, $(C_3-C_7)$cycloalkylcarbonylamido, phenylcarbonylamido, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$cycloalkyl, $(C_1-C_4)$alkyl optionally substituted with up to three fluoro or $(C_1-C_4)$alkoxy optionally substituted with up to five fluoro; said phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for $Het^2$ and $Het^3$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of substituents for $Het^2$ and $Het^3$ are optionally substituted with up to two substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to three fluoro; and $R^{18}$ and $R^{19}$ are each independently hydrogen or $(C_1-C_4)$alkyl, provided that when $R^3$ is $NR^6R^7$, then A is $SO_2$. A particularly preferred compound of the Formula ARI for use as the second compound of a combination of this invention is 6-(5-chloro-3-methyl-benzofuran-2-sulfonyl)-2H-pyridazin-3-one.

Any soluble guanylate cyclase (sGC) activator may be used as the second compound of a combination of this invention. Suitable sGC activators include BAY 41-2272 and BAY 41-8543.

Any growth hormone secretagogue may be used as the second compound of a combination of this invention. Suitable growth hormone secretagogues include those disclosed in U.S. Pat. Nos. 6,124,264; 6,110,932; 6,278,000; and 6,251,902. A particularly preferred growth hormone secretagogue is 2-amino-N-(2-(3a(R)-benzyl-2-methyl-3-oxo-2,3,3a,4,6,7-hexahydro-pyrazolo-[4,3c]pyridin-5-yl)-1 (R)-benzyloxymethyl-2-oxo-ethyl) -isobutyramide.

Particularly preferred compounds for use as the second compound in the combinations and pharmaceutical compositions for use according to the present invention include compounds selected from the following classes of compounds: insulin sensitizing agents, PDE5 inhibitors, protein kinase C-β inhibitors, AMP-activated protein kinase activators, insulin, weight loss agents, PPAR-γ agonists, PPAR-α agonists, dual PPAR-γ/PPAR-α agonists, sorbitol dehydrogenase inhibitors and aldose reductase inhibitors, each as described above.

PDE9 INHIBITOR—TEST METHODS

Phosphodiesterase (PDE) Inhibitory Activity

Preferred PDE compounds suitable for use in accordance with the present invention are potent and cGMP PDE9 inhibitors. In vitro PDE inhibitory activities against cyclic guanosine 3',5'-monophosphate (cGMP) and cyclic adenosine 3',5'-monophosphate (cAMP) phosphodiesterases are determined by measurement of their $IC_{50}$ values (the concentration of compound required for 50% inhibition of enzyme activity).

Phosphodiesterase 9 can be generated from full length human recombinant clones transfected into SF9 cells as described in Fisher et al., Journal of Biological Chemistry, 1998, 273, 15559–15564.

Assays are performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE9 inhibitors is investigated by assaying a fixed amount of enzyme in the presence of varying inhibitor concentrations and low substrate, (cGMP in a 3:1 ratio unlabelled to [$^3$H]-labeled at a concentration of about ⅓ $K_m$) such that $IC_{50} \cong K_i$. The final assay volume is made up to 100 μl with assay buffer [20 mM Tris-HCl pH 7.4, 5 mM $MgCl_2$, 1 mg/ml bovine serum albumin]. Reactions are initiated with enzyme, incubated for 30–60 minutes at 30° C. to give <30% substrate turnover and terminated with 50 μl yttrium silicate SPA beads (containing 3 mM of the respective unlabelled cyclic nucleotide for PDEs 9 and 11). Plates are re-sealed and shaken for 20 minutes, after which the beads are allowed to settle for 30 minutes in the dark and then counted on a TopCount plate reader (Packard, Meriden, Conn.) Radioactivity units are converted to percent activity of an uninhibited control (100%), plotted against inhibitor concentration and inhibitor $IC_{50}$ values obtained using the 'Fit Curve' Microsoft Excel extension.

Effect of Specific PDE9 Inhibitors on Insulin Resistance Syndrome in Animals—Effects on Plasma Glucose, Triglyceride, Insulin, and cGMP Levels in ob/ob Mice.

Biological Data

Experimental Protocol

Test Compounds:

The PDE9 inhibitor compounds to be tested are solubilized in 10% DMSO/0.1% pluronics and dosed via oral gavage using mouse oral feeding needles (20 gauge, Popper & Sons, Inc., New Hyde Park, N.Y.). A volume of 4 ml/kg weight is administered for each dose. Compounds are tested at doses ranging from 1–50 mg/kg.

Experimental Animals:

Male ob/ob mice obtained from Jackson Laboratories (Bar Harbor, Me.) are used in the studies at 6 to 10 weeks of age. Mice are housed five per cage and allowed free access to D11 mouse chow (Purina, Brentwood, Mo.) and water.

Experimental Protocol:

Mice are allowed to acclimate to the Pfizer animal facilities for one week prior to the start of the study. On day one, retro-orbital blood samples are obtained and plasma glucose is determined as described hereinafter. Mice are then sorted into groups of five such that mean plasma glucose concentrations for each group do not differ. On day one, mice are dosed with vehicle or a test PDE9 inhibitor compound only in the afternoon. Subsequently, mice are dosed twice a day on day 2–4 in the morning and in the afternoon. On day five, the mice receive an a.m. dose and are bled 3 hours later for plasma preparation for glucose and triglyceride analysis as described below. Terminal plasma samples are collected on day five following the retro-orbital sinus bleed as described below. Body weight is measured on days one and five of the study, and food consumption is assessed over the five day period.

Terminal Bleed and Tissue Collection:

On the morning of the last day of the study mice are dosed with test compound or vehicle at approximately 8:00 am. Three hours after dosing, 25 μL of blood is obtained via the retro-orbital sinus and is added to 100 μL of 0.025 percent heparinized-saline in Denville Scientific microtubes. The tubes are spun at the highest setting in a Beckman Microfuge 12 for 2 minutes. Plasma is collected for plasma glucose and triglyceride determination. The mice are then sacrificed by decapitation and about one milliliter of blood is collected in Becton-Dickinson Microtainer brand plasma separator tubes with lithium heparin. The tubes are spun in a Beckman Microfuge 12 at the maximum setting for five minutes. Plasma is collected in 1.5 ml Eppendorf tubes and snap frozen in liquid nitrogen. Plasma samples are stored at −80° C. until analyzed.

Metabolite and Hormone Analysis:

Plasma glucose and triglycerides are measured using the Alcyon Clinical Chemistry Analyzer (Abbott Laboratories, Abbott Park, Ill.) using kits supplied by Abbott. Plasma cGMP is measured using the Biotrak enzyme-immunoassay system by Amersham (Piscataway, N.J.). Via a similar technique the plasma insulin is assessed by the Mercodia ELISA Insulin kit by ALPCO (Uppsala, Sweden). All assays are conducted according to instructions provided by the manufacturers.

Results

Table 1 illustrates the changes in plasma glucose, triglyceride, and insulin levels over a five day period observed with Compound A, 5-(3-chloro-benzyl)-3-isopropyl-1,6-dihydro-pyrazolo[4,3-d]pyrimidin-7-one.

Taken together, these experimental results in the hyperglycemic, insulin-resistant ob/ob mouse suggest that selective PDE9 inhibition improves metabolic parameters associated with IRS.

TABLE 1

| Treatment | Plasma Glucose (mg/dl) | Plasma Triglyceride (mg/dl) | Plasma Insulin (pmol/ml) |
|---|---|---|---|
| Vehicle | 370 ± 23 | 207 ± 9 | 12.0 ± 1.5 |
| Compound A (10 mg/kg) | 304 ± 17 | 155 ± 8 | 8.2 ± 1.5 |

The data in Table 1 are presented as mean±standard error of the mean.

Table 2 illustrates the elevation of plasma cGMP produced by five day treatment with 5-(3-chloro-benzyl)-3-isopropyl-1,6-dihydro-pyrazolo[4,3-d]pyrimidin-7-one.

TABLE 2

| Treatment | Plasma cGMP (pmol/ml) |
|---|---|
| Vehicle | 9.8 ± 0.5 |
| Compound A (10 mg/kg) | 16.8 ± 3.1 |

The data in Table 2 are presented as mean±standard error of the mean.

General Procedure For the Preparation of Examples 1 to 77

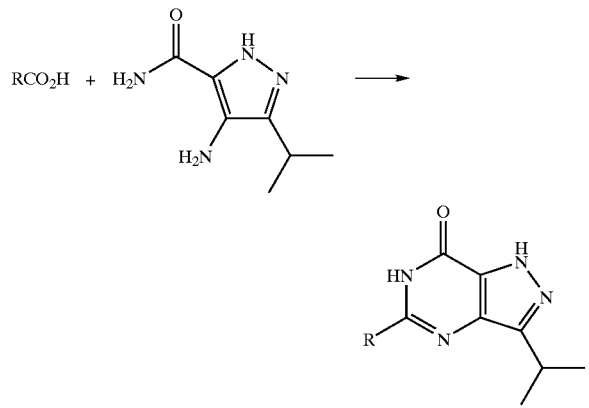

The carboxylic acids (80 μmol) were dissolved in a 3.75% solution of triethylamine in dimethylacetamide (400 μl) and administered to a 96 well plate. Carbonyldiimidazole (13 mg, 80 μmol) dissolved in pyridine (212 μl) was then added into each well, and the plates were left to stand at room temperature for 2 hours. A solution of 4-amino-5-isopropyl-2H-pyrazole-3-carboxylic acid amide (13.5 mg, 80 μmol) dissolved in dimethylacetamide (100 μl) was then added, and the plates were sealed and heated to 70° C. in an oven under nitrogen. This was maintained for 18 hours, upon which the plates were removed and allowed to cool to room temperature (2 hours). The solvent was removed using a GENEVAC (45° C., 0.15 mbar) over 5.5 hours. A solution of potassium t-butoxide (268 mg, 240 μmol) in isopropylalcohol (0.5 ml) was added to each well, and the plates were sealed and transferred to an oven at 110° C. under nitrogen. This was maintained for 15 hours, upon which the plates were removed and allowed to cool to room temperature (2 hours). The solvent was again removed using the GENEVAC (45° C., 0.15 mbar) over 5.5 hours, and a solution of p-toluenesulfonic acid (30 mg, 160 μl) in isopropylalcohol (0.5 ml) was added to each well. The plates were left to stand at room temperature for 18 hours, and the solvent was removed using the GENEVAC (45° C., 0.15 mbar) over 5.5 hours. The residues were dissolved in dimethylsulfoxide (450 μl per well) and each compound was purified by preparative HPLC. The compounds were characterised by LC-MS analysis.

Preparative HPLC Conditions

Column: Phenomenex Luna C18, 5 μm, 150×10 mm id
Temperature: Ambient
Eluent A: 0.05% Diethylamine (aqueous)
Eluent B: Acetonitrile
Sample solvent: 90% dimethylsulfoxide in water
Initial pump conditions: A % 90, B % 10, flow 6 ml/minute
Detection: Gilston 119 uv detector—225 nm
Injection volume—600 μL

| Gradient Timetable | | | |
|---|---|---|---|
| Time (min) | A % | B % | Flow (ml/min) |
| 0.0 | 95 | 5 | 6 |
| 0.2 | 95 | 5 | 6 |
| 7.0 | 5 | 95 | 6 |
| 9.0 | 5 | 95 | 6 |
| 9.1 | 95 | 5 | 6 |
| 10.5 | 95 | 5 | 6 |

LC-MS Conditions

Column: Phenomenex Luna C18, 5 μm, 30×4.6 mm id.
Temperature: 40° C.
Eluent A: 0.05% Diethylamine (aqueous)
Eluent B: Acetonitrile
Initial pump conditions: A % 90, B % 10, flow 3 ml/minute
Injection volume—5 μ
Detection: Start range 210 nm, End range 280 nm, Range interval 5 nm, threshold 0.1 mAU, peakwidth 0.4 min.

| Gradient Timetable | | | | |
|---|---|---|---|---|
| Time (min) | A % | B % | Flow (ml/min) | Pressure (bar) |
| 0.0 | 90 | 10 | 3 | 400 |
| 2.2 | 5 | 95 | 3 | 400 |
| 2.4 | 5 | 95 | 3 | 400 |
| 2.5 | 90 | 10 | 3 | 400 |

ELSD: Sedere Dedex 55, Temperature: 40° C., Gas Flow: 2.3 bar
MS: Platform LC, ES+ Cone voltage: 26 v, Capillary: 4.08 kv
ES− Cone voltage: −24 v, Capillary: −3.58 kv Blanket gas: 500 l/min, Temperature: 130° C.

| Example No. | Compound | Molecular Weight | Retention time (min) |
|---|---|---|---|
| 1 | 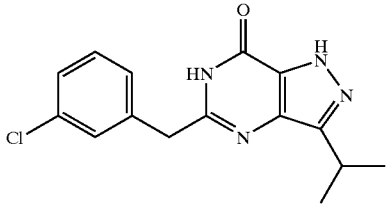<br>5-(3-Chloro-benzyl)-3-isopropyl-1,6-dihydro-pyrazolo[4,3-d]pyrimidin-7-one | 302.1 | 1.95 |
| 2 | 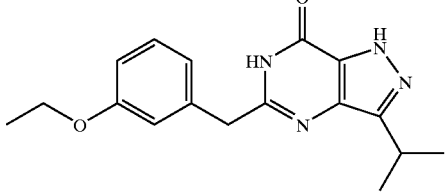<br>5-(3-Ethoxy-benzyl)-3-isopropyl-1,6-dihydro-pyrazolo[4,3-d]pyrimidin-7-one | 312.2 | 1.85 |
| 3 | 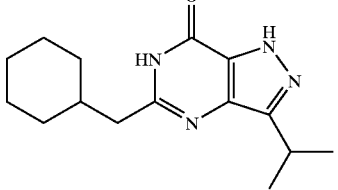<br>5-Cyclohexylmethyl-3-isopropyl-1,6-dihydro-pyrazolo[4,3-d]pyrimidin-7-one | 274.2 | 1.92 |
| 4 | 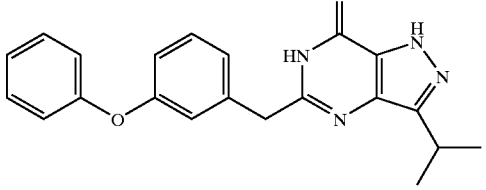<br>3-Isopropyl-5-(3-phenoxy-benzyl)-1,6-dihydro-pyrazolo[4,3-d]pyrimidin-7-one | 360.2 | 2.02 |
| 5 | 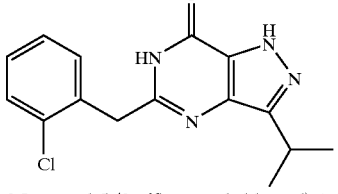<br>3-Isopropyl-5-(2-trifluoromethyl-benzyl)-1,6-dihydro-pyrazolo[4,3-d]pyrimidin-7-one | 302.1 | 1.85 |
| 6 | 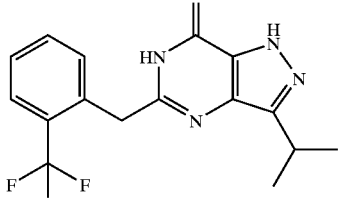<br>5-(3-Chloro-benzyl)-3-isopropyl-1,6-dihydro-pyrazolo[4,3-d]pyrimidin-7-one | 336.1 | 1.96 |

-continued

| Example No. | Compound | Molecular Weight | Retention time (min) |
|---|---|---|---|
| 7 | 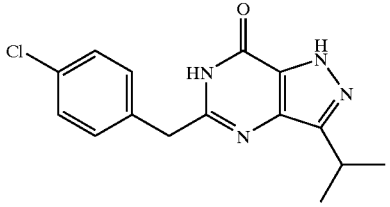<br>5-(4-Chloro-benzyl)-3-isopropyl-1,6-dihydro-pyrazolo[4,3-d]pyrimidin-7-one | 302.1 | 1.91 |
| 8 | 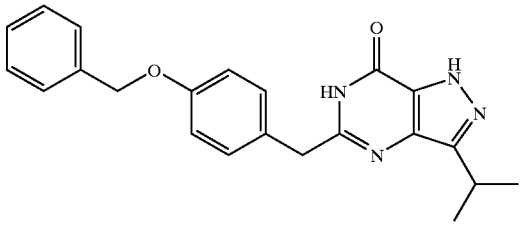<br>5-(4-Benzyloxy-benzyl)-3-isopropyl-1,6-dihydro-pyrazolo[4,3-d]pyrimidin-7-one | 374.2 | 2.05 |
| 9 | 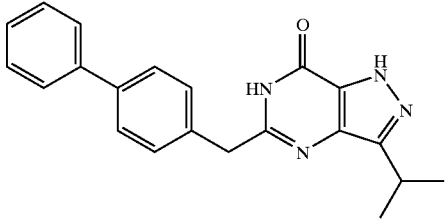<br>5-Biphenyl-4-ylmethyl-3-isopropyl-1,6-dihydro-pyrazolo[4,3-d]pyrimidin-7-one | 344.2 | 2.04 |
| 10 | 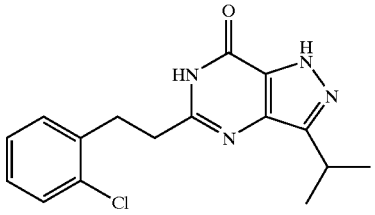<br>5-[2-(2-Chloro-phenyl)-ethyl]-3-isopropyl-1,6-dihydro-pyrazolo[4,3-d]pyrimidin-7-one | 316.1 | 1.93 |
| 11 | 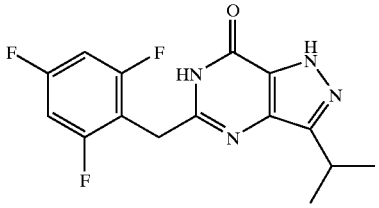<br>3-Isopropyl-5-(2,4,6-trifluoro-benzyl)-1,6-dihydro-pyrazolo[4,3-d]pyrimidin-7-one | 322.1 | 1.89 |

-continued

| Example No. | Compound | Molecular Weight | Retention time (min) |
|---|---|---|---|
| 12 | 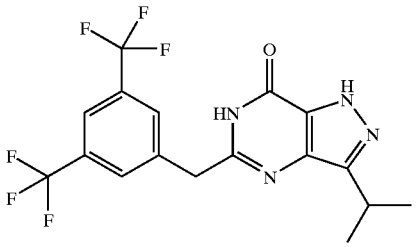<br>5-(3,5-Bis-trifluoromethyl-benzyl)-3-isopropyl-1,6-dihydro-pyrazolo[4,3-d]pyrimidin-7-one | 404.1 | 2.07 |
| 13 | 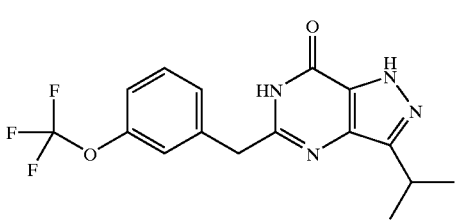<br>3-Isopropyl-5-(3-trifluoromethoxy-benzyl)-1,6-dihydro-pyrazolo[4,3-d]pyrimidin-7-one | 352.1 | 1.97 |
| 14 | 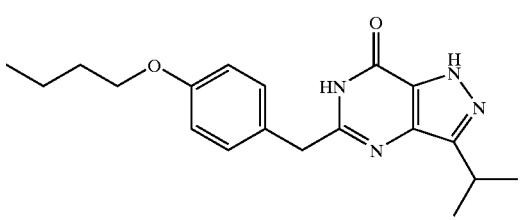<br>5-(4-Butoxy-benzyl)-3-isopropyl-1,6-dihydro-pyrazolo[4,3-d]pyrimidin-7-one | 340.2 | 2.08 |
| 15 | 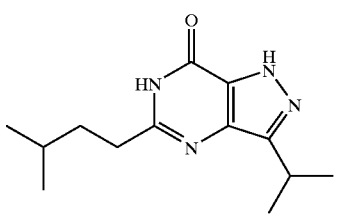<br>3-Isopropyl-5-(3-methyl-butyl)-1,6-dihydro-pyrazolo[4,3-d]pyrimidin-7-one | 248.2 | 1.80 |
| 16 | 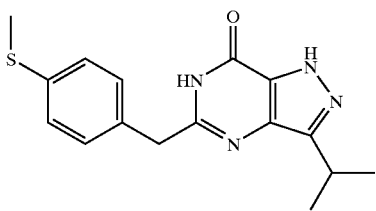<br>3-Isopropyl-5-(4-methylsulfanyl-benzyl)-1,6-dihydro-pyrazolo[4,3-d]pyrimidin-7-one | 314.2 | 1.83 |
| 17 | 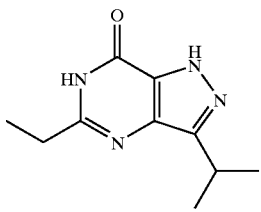<br>5-Ethyl-3-isopropyl-1,6-dihydro-pyrazolo[4,3-d]pyrimidin-7-one | 206.1 | 1.42 |

-continued

| Example No. | Compound | Molecular Weight | Retention time (min) |
|---|---|---|---|
| 18 | 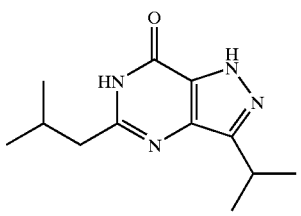<br>5-Isobutyl-3-isopropyl-1,6-dihydro-pyrazolo[4,3-d]pyrimidin-7-one | 234.2 | 1.63 |
| 19 | 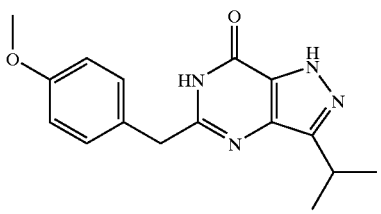<br>3-Isopropyl-5-(4-methoxy-benzyl)-1,6-dihydro-pyrazolo[4,3-d]pyrimidin-7-one | 298.1 | 1.77 |
| 20 | 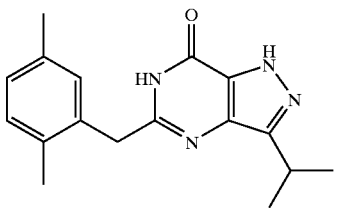<br>5-(2,5-Dimethyl-benzyl)-3-isopropyl-1,6-dihydro-pyrazolo[4,3-d]pyrimidin-7-one | 296.2 | 1.93 |
| 21 | 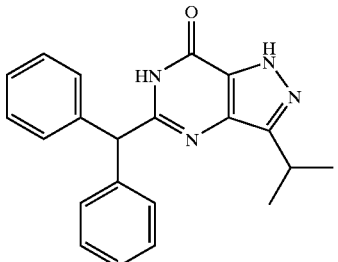<br>5-Benzhydryl-3-isopropyl-1,6-dihydro-pyrazolo[4,3-d]pyrimidin-7-one | 344.2 | 2.07 |
| 22 | 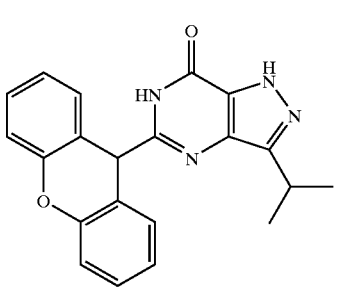<br>3-Isopropyl-5-(9H-xanthen-9-yl)-1,6-dihydro-pyrazolo[4,3-d]pyrimidin-7-one | 358.1 | 2.08 |

| Example No. | Compound | Molecular Weight | Retention time (min) |
|---|---|---|---|
| 23 | 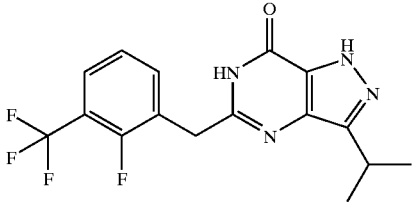 5-(2-Fluoro-3-trifluoromethyl-benzyl)-3-isopropyl-1,6-dihydro-pyrazolo[4,3-d]pyrimidin-7-one | 354.1 | 1.95 |
| 24 | 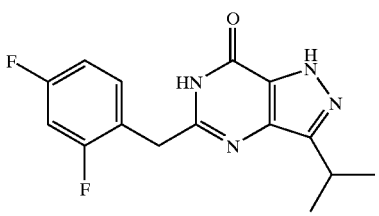 5-(2,4-Difluoro-benzyl)-3-isopropyl-1,6-dihydro-pyrazolo[4,3-d]pyrimidin-7-one | 304.1 | 1.82 |
| 25 | 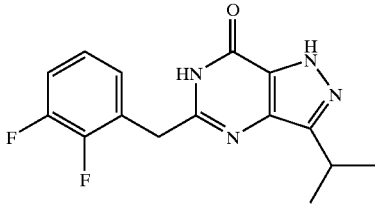 5-(2,3-Difluoro-benzyl)-3-isopropyl-1,6-dihydro-pyrazolo[4,3-d]pyrimidin-7-one | 304.1 | 1.86 |
| 26 | 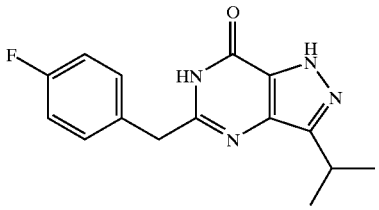 5-(4-Fluoro-benzyl)-3-isopropyl-1,6-dihydro-pyrazolo[4,3-d]pyrimidin-7-one | 286.1 | 1.80 |
| 27 | 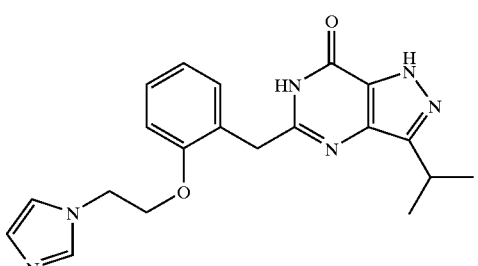 5-[2-(2-Imidazol-1-yl-ethoxy)-benzyl]-3-isopropyl-1,6-dihydro-pyrazolo[4,3-d]pyrimidin-7-one | 378.2 | 1.44 |

-continued

| Example No. | Compound | Molecular Weight | Retention time (min) |
|---|---|---|---|
| 28 | 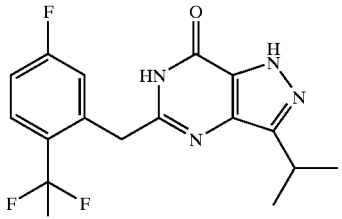<br>5-(5-Fluoro-2-trifluoromethyl-benzyl)-3-isopropyl-1,6-dihydro-pyrazolo[4,3-d]pyrimidin-7-one | 354.1 | 1.98 |
| 29 | 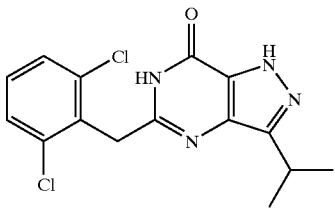<br>5-(2,6-Dichloro-benzyl)-3-isopropyl-1,6-dihydro-pyrazolo[4,3-d]pyrimidin-7-one | 336.1 | 1.97 |
| 30 | 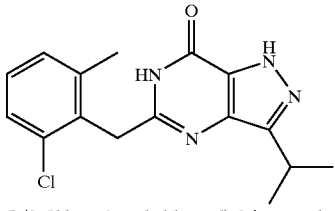<br>5-(2-Chloro-6-methyl-benzyl)-3-isopropyl-1,6-dihydro-pyrazolo[4,3-d]pyrimidin-7-one | 332.1 | 2.03 |
| 31 | 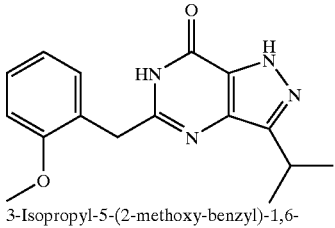<br>3-Isopropyl-5-(2-methoxy-benzyl)-1,6-dihydro-pyrazolo[4,3-d]pyrimidin-7-one | 298.1 | 1.76 |
| 32 | 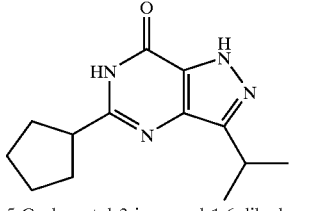<br>5-Cyclopentyl-3-isopropyl-1,6-dihydro-pyrazolo[4,3-d]pyrimidin-7-one | 246.2 | 1.83 |
| 33 | 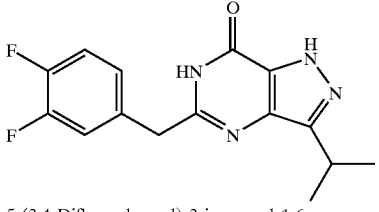<br>5-(3,4-Difluoro-benzyl)-3-isopropyl-1,6-dihydro-pyrazolo[4,3-d]pyrimidin-7-one | 304.1 | 1.83 |

| Example No. | Compound | Molecular Weight | Retention time (min) |
|---|---|---|---|
| 34 | N-{1R-1-(3-Isopropyl-7-oxo-6,7-dihydro-1H-pyrazolo[4,3-d]pyrimidin-5-yl)-2-phenyl-ethyl}-acetamide | 339.2 | 1.73 |
| 35 | 5-(4-Methyl-benzyl)-3-isopropyl-1,6-dihydro-pyrazolo[4,3-d]pyrimidin-7-one | 282.2 | 1.83 |
| 36 | 3-Isopropyl-5-[2-(4-methoxy-phenyl)-1-phenyl-ethyl]-1,6-dihydro-pyrazolo[4,3-d]pyrimidin-7-one | 388.2 | 2.13 |
| 37 | 3-Isopropyl-5-napthalen-1-ylmethyl-1,6-dihydro-pyrazolo[4,3-d]pyrimidin-7-one | 318.2 | 2.05 |
| 38 | 5-Cyclopentylmethyl-3-isopropyl-1,6-dihydro-pyrazolo[4,3-d]pyrimidin-7-one | 260.2 | 1.77 |

-continued

| Example No. | Compound | Molecular Weight | Retention time (min) |
|---|---|---|---|
| 39 | 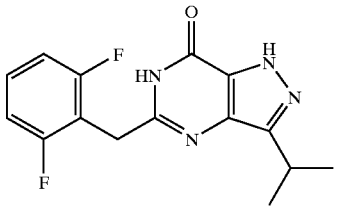<br>5-(2,6-Difluoro-benzyl)-3-isopropyl-1,6-dihydro-pyrazolo[4,3-d]pyrimidin-7-one | 304.1 | 1.83 |
| 40 | 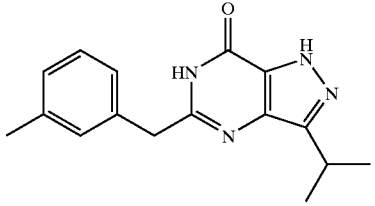<br>5-(3-Methyl-benzyl)-3-isopropyl-1,6-dihydro-pyrazolo[4,3-d]pyrimidin-7-one | 282.2 | 1.84 |
| 41 | 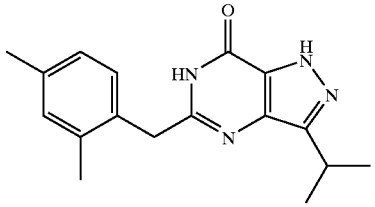<br>5-(2,4-Dimethyl-benzyl)-3-isopropyl-1,6-dihydro-pyrazolo[4,3-d]pyrimidin-7-one | 296.2 | 1.99 |
| 42 | 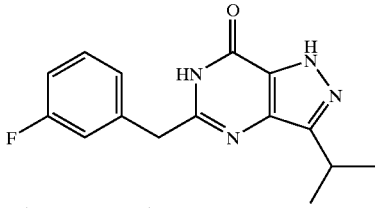<br>5-(3-Fluoro-benzyl)-3-isopropyl-1,6-dihydro-pyrazolo[4,3-d]pyrimidin-7-one | 286.1 | 1.82 |
| 43 | 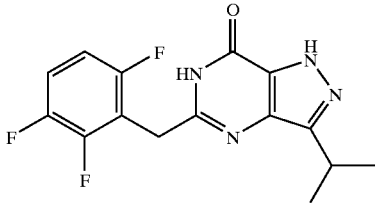<br>5-(2,3,6-Trifluoro-benzyl)-3-isopropyl-1,6-dihydro-pyrazolo[4,3-d]pyrimidin-7-one | 322.1 | 1.91 |
| 44 | 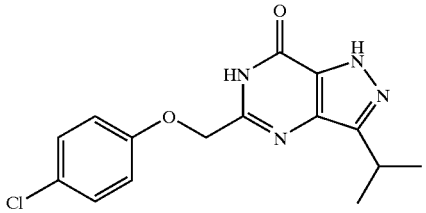<br>5-(4-Chloro-phenoxymethyl)-3-isopropyl-1,6-dihydro-pyrazolo[4,3-d]pyrimidin-7-one | 318.1 | 1.97 |

-continued

| Example No. | Compound | Molecular Weight | Retention time (min) |
|---|---|---|---|
| 45 | 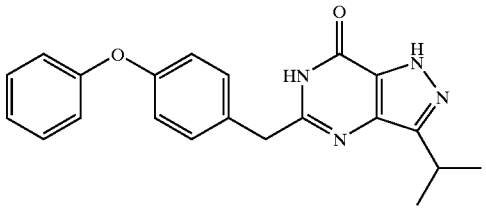<br>3-Isopropyl-5-(4-phenoxy-benzyl)-1,6-dihydro-pyrazolo[4,3-d]pyrimidin-7-one | 360.2 | 2.05 |
| 46 | 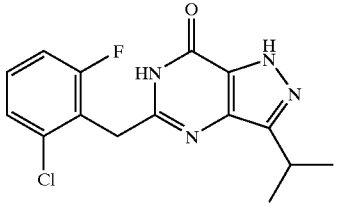<br>5-(2-Chloro-6-fluoro-benzyl)-3-isopropyl-1,6-dihydro-pyrazolo[4,3-d]pyrimidin-7-one | 320.1 | 1.88 |
| 47 | 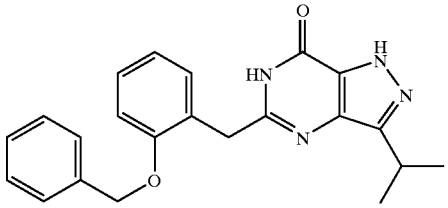<br>5-(2-Benzyloxy-benzyl)-3-isopropyl-1,6-dihydro-pyrazolo[4,3-d]pyrimidin-7-one | 374.2 | 2.04 |
| 48 | 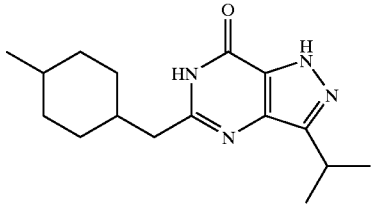<br>3-Isopropyl-5-(4-methyl-cyclohexylmethyl)-1,6-dihydro-pyrazolo[4,3-d]pyrimidin-7-one | 288.2 | 2.02 |
| 49 | 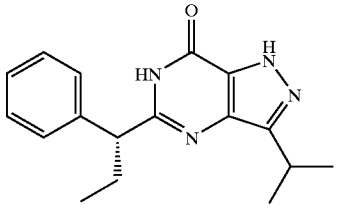<br>3-Isopropyl-5-(1R-1-phenyl-propyl)-1,6-dihydro-pyrazolo[4,3-d]pyrimidin-7-one | 296.2 | 2.09 |
| 50 | 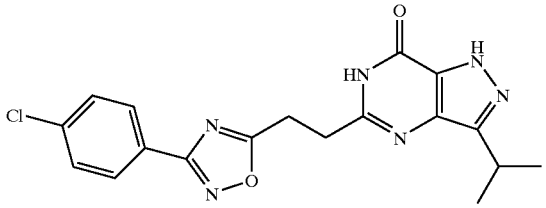<br>5-{2-[3-(4-Chloro-phenyl)-[1,2,4]oxadiazol 5-yl]-ethyl}-3-isopropyl-1,6-dihydro pyrazolo[4,3-d]pyrimidin-7-one | 384.1 | 2.05 |

-continued

| Example No. | Compound | Molecular Weight | Retention time (min) |
|---|---|---|---|
| 51 | 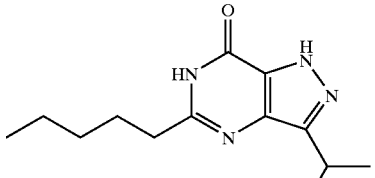<br>3-Isopropyl-5-pentyl-1,6-dihydro-pyrazolo[4,3-d]pyrimidin-7-one | 248.2 | 1.83 |
| 52 | 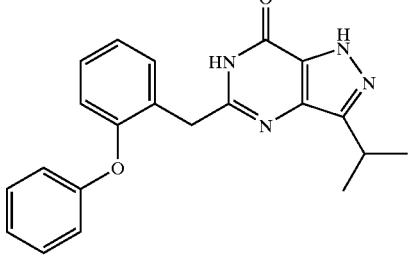<br>3-Isopropyl-5-(2-phenoxy-benzyl)-1,6-dihydro-pyrazolo[4,3-d]pyrimidin-7-one | 360.2 | 2.03 |
| 53 | 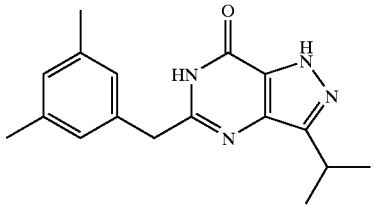<br>5-(3,5-Dimethyl-benzyl)-3-isopropyl-1,6-dihydro-pyrazolo[4,3-d]pyrimidin-7-one | 296.2 | 1.97 |
| 54 | 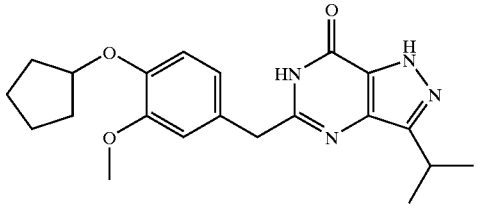<br>5-(4-Cyclopentyloxy-3-methoxy-benzyl)-3-isopropyl-1,6-dihydro-pyrazolo[4,3-d]pyrimidin-7-one | 382.2 | 1.95 |
| 55 | 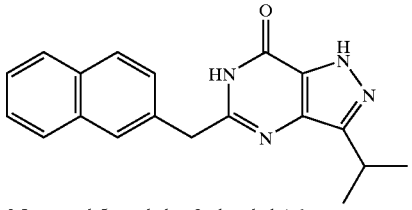<br>3-Isopropyl-5-napthalen-2-ylmethyl-1,6-dihydro-pyrazolo[4,3-d]pyrimidin-7-one | 318.2 | 1.97 |
| 56 | 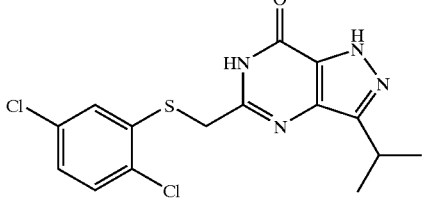<br>5-(2,5-Dichloro-phenylsulfanylmethyl)-3-isopropyl-1,6-dihydro-pyrazolo[4,3-d]pyrimidin-7-one | 368.0 | 2.09 |

-continued

| Example No. | Compound | Molecular Weight | Retention time (min) |
|---|---|---|---|
| 57 | 3-Isopropyl-5-(1S-1-phenyl-ethyl)-1,6-dihydro-pyrazolo[4,3-d]pyrimidin-7-one | 282.2 | 1.95 |
| 58 | 3-Isopropyl-5-(2-methyl-butyl)-1,6-dihydro-pyrazolo[4,3-d]pyrimidin-7-one | 248.2 | 1.78 |
| 59 | 5-(2,5-Difluoro-benzyl)-3-isopropyl-1,6-dihydro-pyrazolo[4,3-d]pyrimidin-7-one | 304.1 | 1.86 |
| 60 | 5-Benzyl-3-isopropyl-1,6-dihydro-pyrazolo[4,3-d]pyrimidin-7-one | 268.1 | 1.77 |
| 61 | 3-Isopropyl-5-(4-methyl-pentyl)-1,6-dihydro-pyrazolo[4,3-d]pyrimidin-7-one | 262.2 | 1.94 |
| 62 | 5-(2-Cyclohexyl-ethyl)-3-isopropyl-1,6-dihydro-pyrazolo[4,3-d]pyrimidin-7-one | 288.2 | 2.07 |

| Example No. | Compound | Molecular Weight | Retention time (min) |
|---|---|---|---|
| 63 | 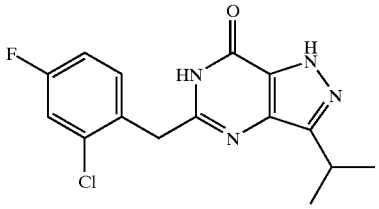<br>5-(2-Chloro-4-fluoro-benzyl)-3-isopropyl-1,6-dihydro-pyrazolo[4,3-d]pyrimidin-7-one | 320.1 | 1.92 |
| 64 | 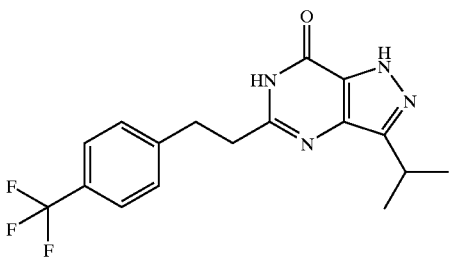<br>3-Isopropyl-5-[2-(4-trifluoromethyl-phenyl)-ethyl]-1,6-dihydro-pyrazolo[4,3-d]pyrimidin-7-one | 350.1 | 2.03 |
| 65 | 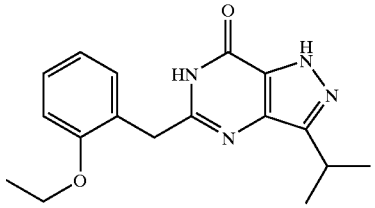<br>5-(2-Ethoxy-benzyl)-3-isopropyl-1,6-dihydro-pyrazolo[4,3-d]pyrimidin-7-one | 312.2 | 1.88 |
| 66 | 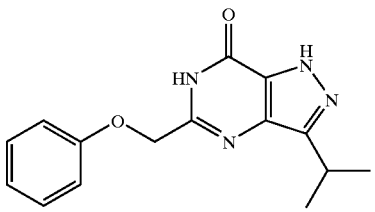<br>3-Isopropyl-5-phenoxymethyl-1,6-dihydro-pyrazolo[4,3-d]pyrimidin-7-one | 284.1 | 1.85 |
| 67 | 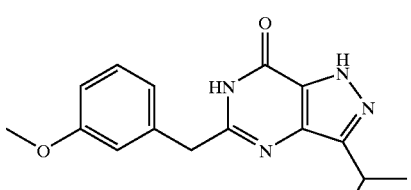<br>5-(3-Methoxy-benzyl)-3-isopropyl-1,6-dihydro-pyrazolo[4,3-d]pyrimidin-7-one | 298.1 | 1.76 |

-continued

| Example No. | Compound | Molecular Weight | Retention time (min) |
|---|---|---|---|
| 68 | 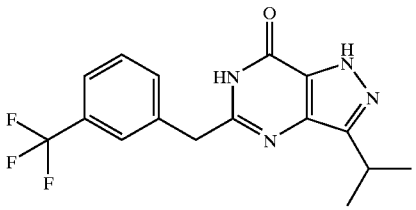<br>5-(3-Trifluoromethyl-benzyl)-3-isopropyl-1,6-dihydro-pyrazolo[4,3-d]pyrimidin-7-one | 336.1 | 1.99 |
| 69 | 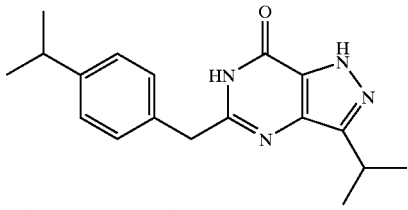<br>5-(4-Isopropyl-benzyl)-3-isopropyl-1,6-dihydro-pyrazolo[4,3-d]pyrimidin-7-one | 310.2 | 2.04 |
| 70 | 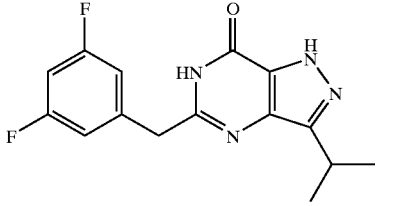<br>5-(3,5-Difluoro-benzyl)-3-isopropyl-1,6-dihydro-pyrazolo[4,3-d]pyrimidin-7-one | 304.1 | 1.89 |
| 71 | 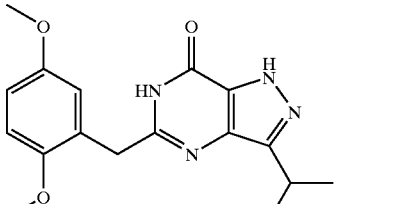<br>5-(2,5-Dimethoxy-benzyl)-3-isopropyl-1,6-dihydro-pyrazolo[4,3-d]pyrimidin-7-one | 328.2 | 1.80 |
| 72 | 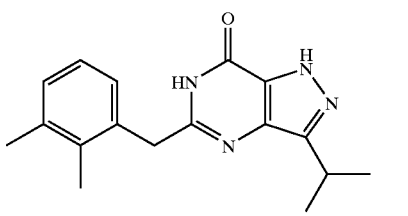<br>5-(2,3-Dimethyl-benzyl)-3-isopropyl-1,6-dihydro-pyrazolo[4,3-d]pyrimidin-7-one | 312.2 | 2.04 |
| 73 | 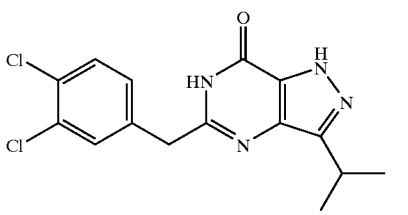<br>5-(3,4-Dichloro-benzyl)-3-isopropyl-1,6-dihydro-pyrazolo[4,3-d]pyrimidin-7-one | 336.1 | 2.02 |

-continued

| Example No. | Compound | Molecular Weight | Retention time (min) |
|---|---|---|---|
| 74 | 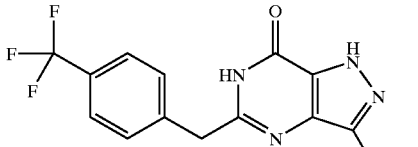 5-(4-Trifluoromethyl-benzyl)-3-isopropyl-1,6-dihydro-pyrazolo[4,3-d]pyrimidin-7-one | 336.1 | 1.93 |
| 75 | 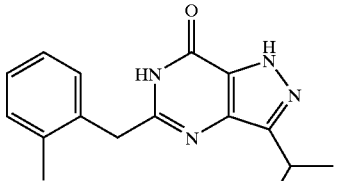 5-(2-Methyl-benzyl)-3-isopropyl-1,6-dihydro-pyrazolo[4,3-d]pyrimidin-7-one | 282.2 | 1.85 |
| 76 | 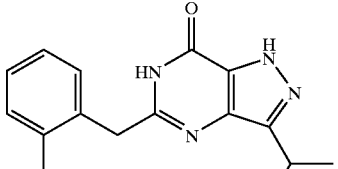 5-(2-Fluoro-benzyl)-3-isopropyl-1,6-dihydro-pyrazolo[4,3-d]pyrimidin-7-one | 286.1 | 1.80 |
| 77 | 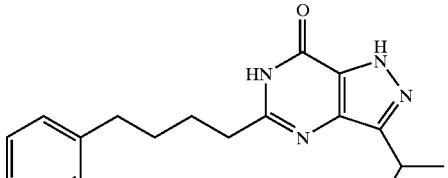 3-Isopropyl-5-(4-phenyl-butyl)-1,6-dihydro-pyrazolo[4,3-d]pyrimidin-7-one | 310.2 | 1.98 |

General Procedure for the Preparation of Examples 78 to 159

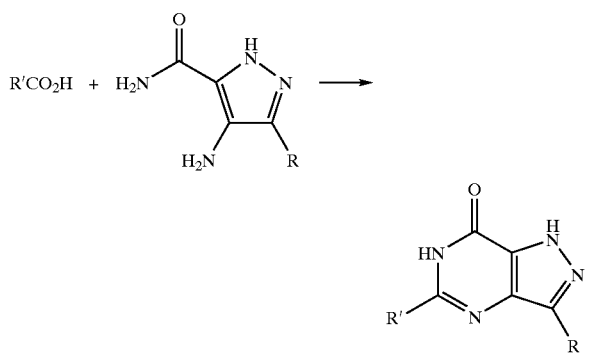

The carboxylic acids (80 μmol) were dissolved in a 3.75% solution of triethylamine in dimethylacetamide (400 μl) and administered to a 96 well plate. Carbonyidiimidazole (13 mg, 80 μmol) dissolved in pyridine (212 μl) was then added into each well, and the plates were left to stand at room temperature for 2 hours. A solution of 5-substituted-4-amino-pyrazole3-carboxamide (80 μmol) dissolved in dimethylacetamide (100 μl) was then added, and the plates were sealed and heated to 70° C. in an oven under nitrogen. This was maintained for 18 hours, upon which the plates were removed and allowed to cool to room temperature (2 hours). The solvent was removed using a GENEVAC (30° C., 0.15 mbar) over 11 hours. A solution of potassium t-butoxide (268 mg, 240 μmol) in isopropylalcohol (0.5 ml) was added to each well, and the plates were sealed and transferred to an oven at 110° C. under nitrogen. This was maintained for 15 hours, upon which the plates were removed and allowed to cool to room temperature (2 hours). The solvent was again removed using the GENEVAC (30° C., 0.15 mbar) over 11 hours, and a solution of p-toluenesulfonic acid (30 mg, 160 μl) in isopropylalcohol (0.5 ml) was added to each well. The plates were left to stand at room temperature for 18 hours, and the solvent was removed using the GENEVAC (30° C., 0.15 mbar) over 11 hours. The residues were dissolved in dimethylsulfoxide (450 μl per well) and each compound was purified by preparative HPLC. The compounds were characterised by LC-MS analysis.

Preparative HPLC Conditions

Column: Phenomenex Luna C18, 5 μm, 150×10 mm id
Temperature: Ambient
Eluent A: 0.05% Diethylamine (aqueous)
Eluent B: Acetonitrile
Sample solvent: 90% dimethylsulfoxide in water
Initial pump conditions: A % 90, B % 10, flow 6 ml/minute
Detection: Gilston 119 uv detector—225 nm
Injection volume—600 μl

| Gradient Timetable | | | |
|---|---|---|---|
| Time (min) | A % | B % | Flow (ml/min) |
| 0.0 | 95 | 5 | 6 |
| 0.2 | 95 | 5 | 6 |
| 7.0 | 5 | 95 | 6 |
| 9.0 | 5 | 95 | 6 |
| 9.1 | 95 | 5 | 6 |
| 10.5 | 95 | 5 | 6 |

LC-MS Conditions

Column: Phenomenex Luna C18, 5 μm, 30×4.6 mm id.
Temperature: 40° C.
Eluent A: 0.05% Diethylamine (aqueous)
Eluent B: Acetonitrile
Initial pump conditions: A % 90, B % 10, flow 3 ml/minute
Injection volume—5 μl
Detection: Start range 210 nm, End range 280 nm, Range interval 5 nm, threshold 0.1 mAU, peakwidth 0.4 min.

| Gradient Timetable | | | | |
|---|---|---|---|---|
| Time (min) | A % | B % | Flow (ml/min) | Pressure (bar) |
| 0.0 | 90 | 10 | 3 | 400 |
| 2.2 | 5 | 95 | 3 | 400 |
| 2.4 | 5 | 95 | 3 | 400 |
| 2.5 | 90 | 10 | 3 | 400 |

ELSD: Sedere Dedex 55, Temperature: 40° C., Gas Flow: 2.3 bar

MS: Platform LC, ES+ Cone voltage: 26 v, Capillary: 4.08 kv ES− Cone voltage: −24 v, Capillary: −3.58 kv Blanket gas: 500 l/min, Temperature: 130° C.

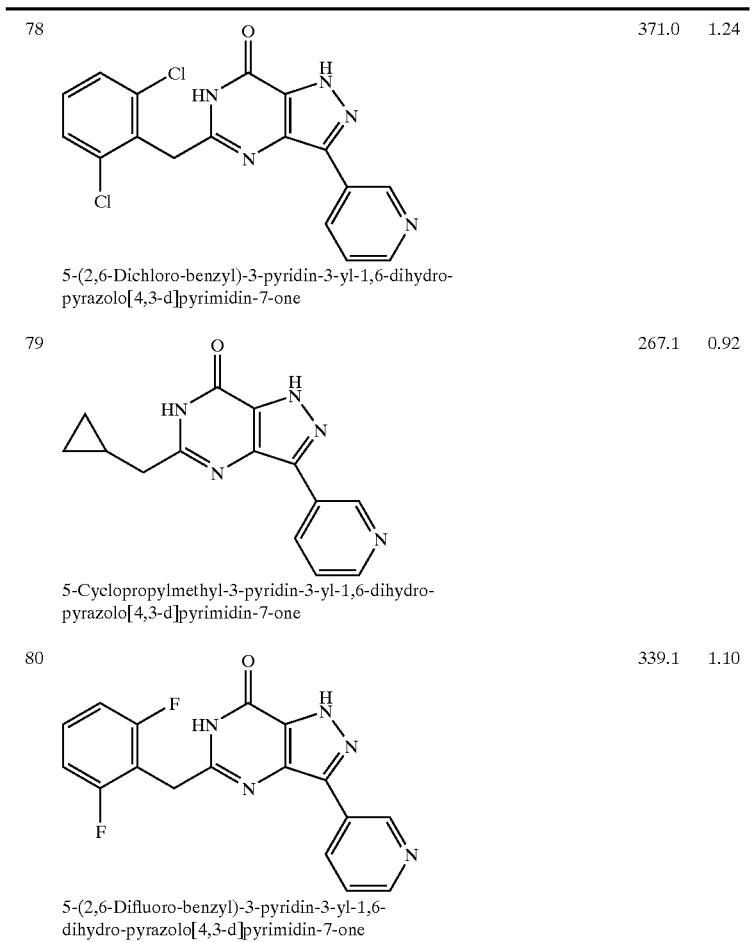

78  5-(2,6-Dichloro-benzyl)-3-pyridin-3-yl-1,6-dihydro-pyrazolo[4,3-d]pyrimidin-7-one  371.0  1.24

79  5-Cyclopropylmethyl-3-pyridin-3-yl-1,6-dihydro-pyrazolo[4,3-d]pyrimidin-7-one  267.1  0.92

80  5-(2,6-Difluoro-benzyl)-3-pyridin-3-yl-1,6-dihydro-pyrazolo[4,3-d]pyrimidin-7-one  339.1  1.10

| | | | |
|---|---|---|---|
| 81 | 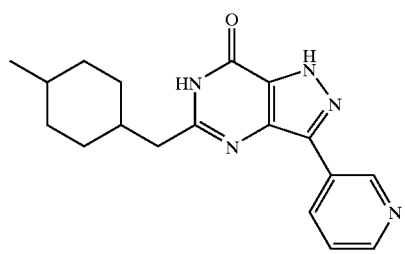<br>5-(4-Methyl-cyclohexylmethyl)-3-pyridin-3-yl-1,6-dihydro-pyrazolo[4,3-d]pyrimidin-7-one | 323.2 | 1.46 |
| 82 | 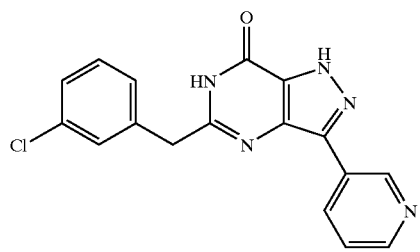<br>5-(3-Chloro-benzyl)-3-pyridin-3-yl-1,6-dihydro-pyrazolo[4,3-d]pyrimidin-7-one | 337.1 | 1.23 |
| 83 | 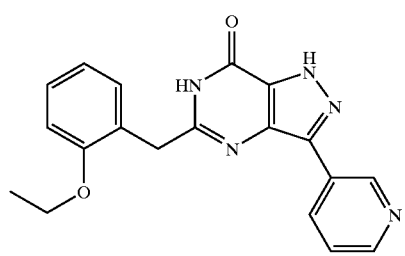<br>5-(2-Ethoxy-benzyl)-3-pyridin-3-yl-1,6-dihydro-pyrazolo[4,3-d]pyrimidin-7-one | 347.1 | 1.24 |
| 84 | 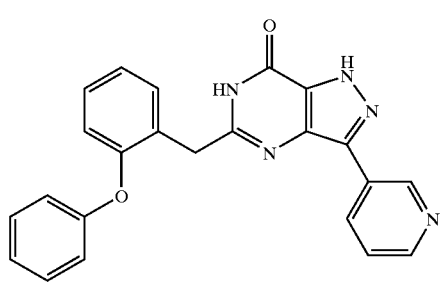<br>5-(2-Phenoxy-benzyl)-3-pyridin-3-yl-1,6-dihydro-pyrazolo[4,3-d]pyrimidin-7-one | 395.1 | 1.46 |
| 85 | 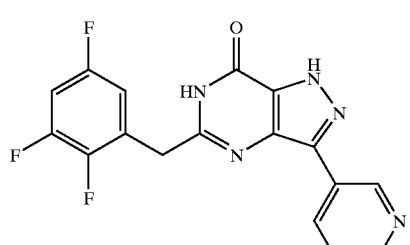<br>5-(2,3,5-Trifluoro-benzyl)-3-pyridin-3-yl-1,6-dihydro-pyrazolo[4,3-d]pyrimidin-7-one | 357.1 | 1.18 |

-continued
| | | | |
|---|---|---|---|
| 86 | 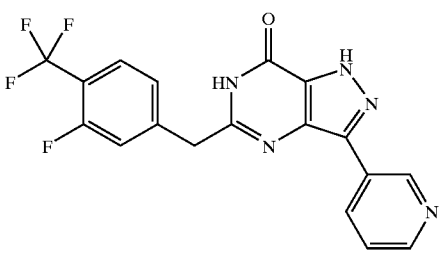5-(3-Fluoro-4-trifluoromethyl-benzyl)-3-pyridin-3-yl-1,6-dihydro-pyrazolo[4,3-d]pyrimidin-7-one | 389.1 | 1.37 |
| 87 | 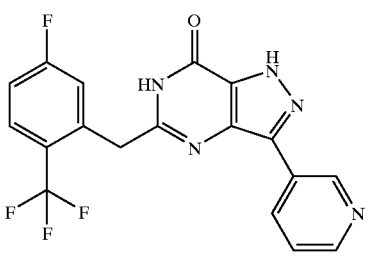5-(5-Fluoro-2-trifluoromethyl-benzyl)-3-pyridin-3-yl-1,6-dihydro-pyrazolo[4,3-d]pyrimidin-7-one | 389.1 | 1.29 |
| 88 | 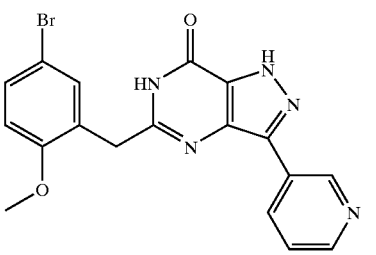5-(5-Bromo-2-methoxy-benzyl)-3-pyridin-3-yl-1,6-dihydro-pyrazolo[4,3-d]pyrimidin-7-one | 411.0 | 1.30 |
| 89 | 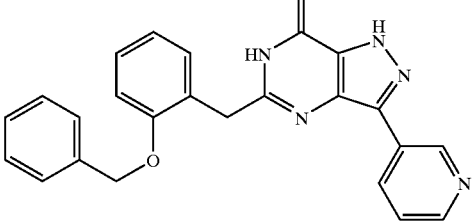5-(2-Benzyloxy-benzyl)-3-pyridin-3-yl-1,6-dihydro-pyrazolo[4,3-d]pyrimidin-7-one | 409.2 | 1.42 |
| 90 | 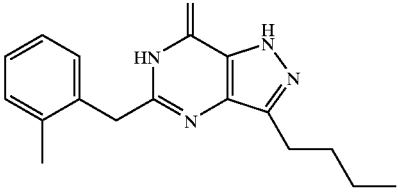3-Butyl-5-(2-methyl-benzyl)-1,6-dihydro-pyrazolo[4,3-d]pyrimidin-7-one | 296.2 | 1.44 |

-continued
| | | | |
|---|---|---|---|
| 91 | 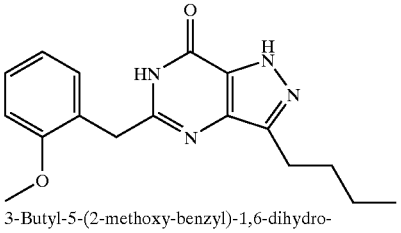 3-Butyl-5-(2-methoxy-benzyl)-1,6-dihydro-pyrazolo[4,3-d]pyrimidin-7-one | 312.2 | 1.36 |
| 92 | 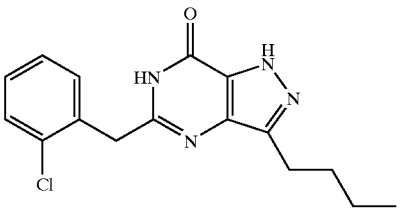 3-Butyl-5-(2-chloro-benzyl)-1,6-dihydro-pyrazolo[4,3-d]pyrimidin-7-one | 316.1 | 1.45 |
| 93 | 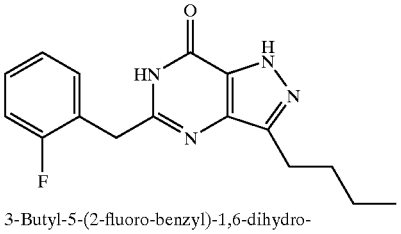 3-Butyl-5-(2-fluoro-benzyl)-1,6-dihydro-pyrazolo[4,3-d]pyrimidin-7-one | 300.14 | 1.34 |
| 94 | 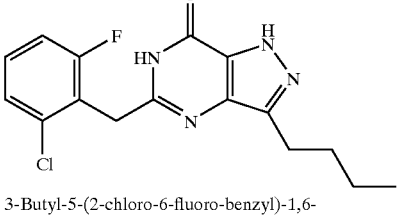 3-Butyl-5-(2-chloro-6-fluoro-benzyl)-1,6-dihydro-pyrazolo[4,3-d]pyrimidin-7-one | 334.1 | 1.47 |
| 95 | 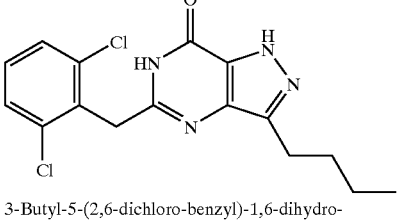 3-Butyl-5-(2,6-dichloro-benzyl)-1,6-dihydro-pyrazolo[4,3-d]pyrimidin-7-one | 350.1 | 1.56 |
| 96 | 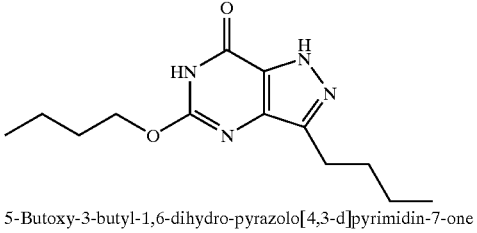 5-Butoxy-3-butyl-1,6-dihydro-pyrazolo[4,3-d]pyrimidin-7-one | 354.2 | 1.72 |

-continued

| | | | |
|---|---|---|---|
| 97 | 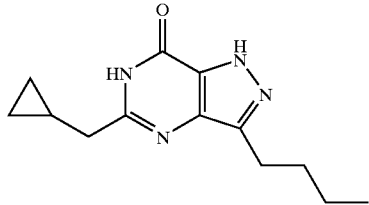<br>3-Butyl-5-cyclopropylmethyl-1,6-dihydro-pyrazolo[4,3-d]pyrimidin-7-one | 246.2 | 1.14 |
| 98 | 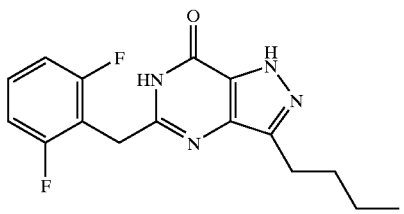<br>3-Butyl-5-(2,6-difluoro-benzyl)-1,6-dihydro-pyrazolo[4,3-d]pyrimidin-7-one | 318.1 | 1.38 |
| 99 | 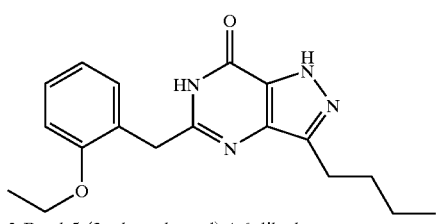<br>3-Butyl-5-(2-ethoxy-benzyl)-1,6-dihydro-pyrazolo[4,3-d]pyrimidin-7-one | 326.2 | 1.48 |
| 100 | 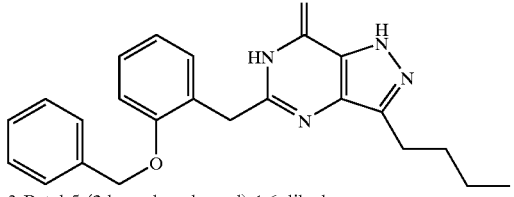<br>3-Butyl-5-(2-benzyloxy-benzyl)-1,6-dihydro-pyrazolo[4,3-d]pyrimidin-7-one | 388.2 | 1.67 |
| 101 | 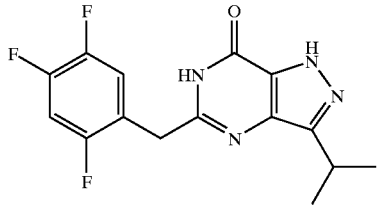<br>5-(2,4,5-Trifluoro-benzyl)-3-isopropyl-1,6-dihydro-pyrazolo[4,3-d]pyrimidin-7-one | 322.1 | 1.36 |
| 102 | 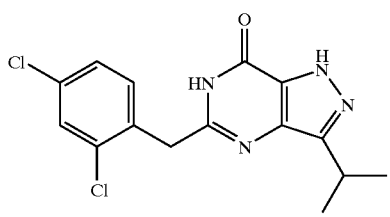<br>5-(2,4-Dichloro-benzyl)-3-isopropyl-1,6-dihydro-pyrazolo[4,3-d]pyrimidin-7-one | 336.1 | 1.54 |

| | | -continued | | |
|---|---|---|---|---|
| 103 | 5-(5-Bromo-2-methoxy-benzyl)-3-isopropyl-1,6-dihydro-pyrazolo[4,3-d]pyrimidin-7-one | | 376.1 | 1.46 |
| 104 | 5-(2,3,6-Trichloro-benzyl)-3-isopropyl-1,6-dihydro-pyrazolo[4,3-d]pyrimidin-7-one | | 370.0 | 1.59 |
| 105 | 5-(3-Benzyloxy-benzyl)-3-isopropyl-1,6-dihydro-pyrazolo[4,3-d]pyrimidin-7-one | | 374.2 | 1.59 |
| 106 | 3-isopropyl-5-propyl-1,6-dihydro-pyrazolo[4,3-d]pyrimidin-7-one | | 220.1 | 0.96 |
| 107 | 5-(2-Trifluoromethoxy-benzyl)-3-isopropyl-1,6-dihydro-pyrazolo[4,3-d]pyrimidin-7-one | | 352.1 | 1.49 |
| 108 | 3-tert-Butyl-5-(3-chloro-benzyl)-1,6-dihydro-pyrazolo[4,3-d]pyrimidin-7-one | | 316.1 | 1.61 |

-continued

| | | | |
|---|---|---|---|
| 109 | 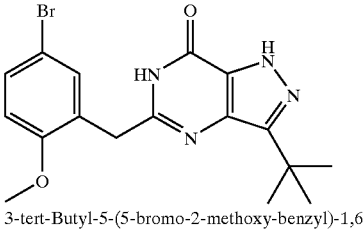 3-tert-Butyl-5-(5-bromo-2-methoxy-benzyl)-1,6-dihydro-pyrazolo[4,3-d]pyrimidin-7-one | 390.1 | 1.68 |
| 110 | 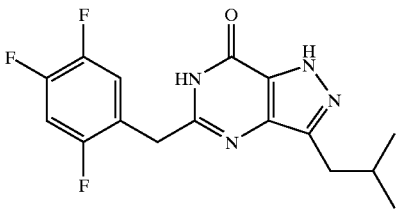 3-Isobutyl-5-(2,4,5-trifluoro-benzyl)-1,6-dihydro-pyrazolo[4,3-d]pyrimidin-7-one | 336.1 | 1.42 |
| 111 | 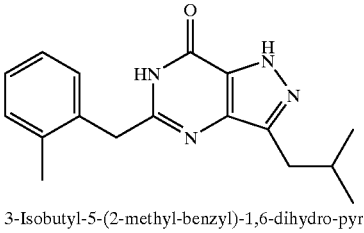 3-Isobutyl-5-(2-methyl-benzyl)-1,6-dihydro-pyrazolo[4,3-d]pyrimidin-7-one | 296.2 | 1.40 |
| 112 | 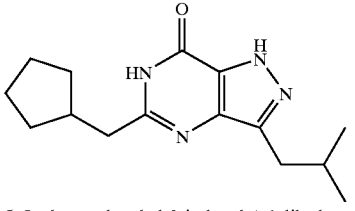 5-Cyclopentylmethyl-3-isobutyl-1,6-dihydro-pyrazolo[4,3-d]pyrimidin-7-one | 274.2 | 1.39 |
| 113 | 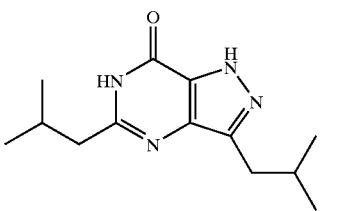 3,5-Diisobutyl-1,6-dihydro-pyrazolo[4,3-d]pyrimidin-7-one | 248.2 | 1.20 |
| 114 | 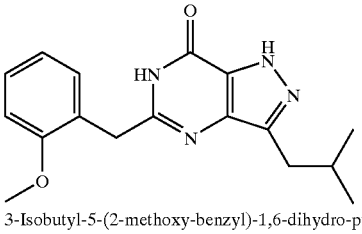 3-Isobutyl-5-(2-methoxy-benzyl)-1,6-dihydro-pyrazolo[4,3-d]pyrimidin-7-one | 312.2 | 1.32 |

-continued

| # | Structure / Name | Mass | RT |
|---|---|---|---|
| 115 | 3-Isobutyl-5-(2-chloro-benzyl)-1,6-dihydro-pyrazolo[4,3-d]pyrimidin-7-one | 316.1 | 1.41 |
| 116 | 3-Isobutyl-5-(2-fluoro-benzyl)-1,6-dihydro-pyrazolo[4,3-d]pyrimidin-7-one | 300.1 | 1.31 |
| 117 | 3-Isobutyl-5-(2-chloro-6-fluoro-benzyl)-1,6-dihydro-pyrazolo[4,3-d]pyrimidin-7-one | 334.1 | 1.44 |
| 118 | 3-Isopropyl-5-(2-methyl-butyl)-1,6-dihydro-pyrazolo[4,3-d]pyrimidin-7-one | 262.2 | 1.35 |
| 119 | 3-Isobutyl-5-(2-trifluoromethyl-benzyl)-1,6-dihydro-pyrazolo[4,3-d]pyrimidin-7-one | 350.1 | 1.53 |
| 120 | 3-Isobutyl-5-(2,4-dichloro-benzyl)-1,6-dihydro-pyrazolo[4,3-d]pyrimidin-7-one | 350.1 | 1.61 |

| | | | |
|---|---|---|---|
| 121 | 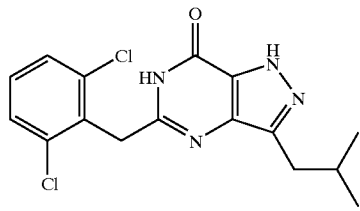<br>3-Isobutyl-5-(2,6-dichloro-benzyl)-1,6-dihydro-pyrazolo[4,3-d]pyrimidin-7-one | 350.1 | 1.54 |
| 122 | 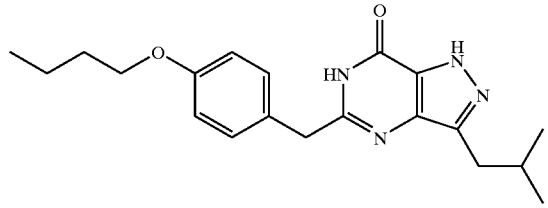<br>5-(4-Butoxy-benzyl)-3-Isopropyl-1,6-dihydro-pyrazolo[4,3-d]pyrimidin-7-one | 354.2 | 1.69 |
| 123 | 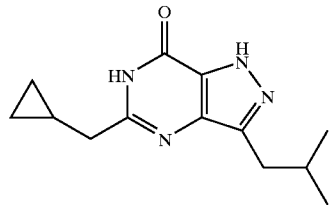<br>5-Cyclopropylmethyl-3-isobutyl-1,6-dihydro-pyrazolo[4,3-d]pyrimidin-7-one | 246.2 | 1.08 |
| 124 | 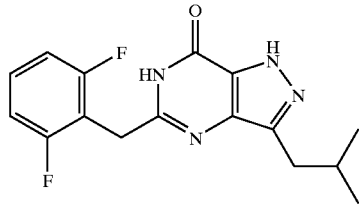<br>3-Isobutyl-5-(2,6-difluoro-benzyl)-1,6-dihydro-pyrazolo[4,3-d]pyrimidin-7-one | 318.1 | 1.34 |
| 125 | 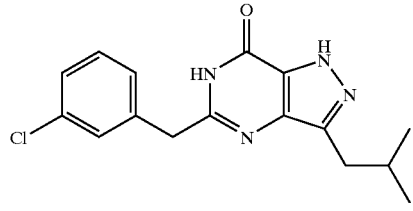<br>3-Isobutyl-5-(3-chloro-benzyl)-1,6-dihydro-pyrazolo[4,3-d]pyrimidin-7-one | 316.1 | 1.44 |
| 126 | 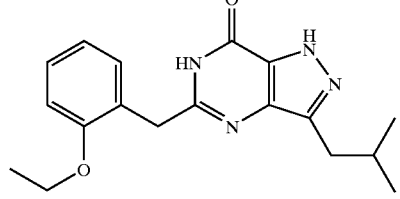<br>3-Isobutyl-5-(2-ethoxy-benzyl)-1,6-dihydro-pyrazolo[4,3-d]pyrimidin-7-one | 326.2 | 1.44 |

| | | | |
|---|---|---|---|
| 127 | 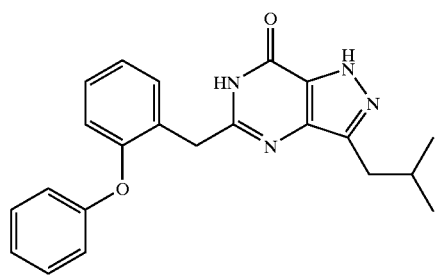 3-Isobutyl-5-(2-phenoxy-benzyl)-1,6-dihydro-pyrazolo[4,3-d]pyrimidin-7-one | 374.2 | 1.65 |
| 128 | 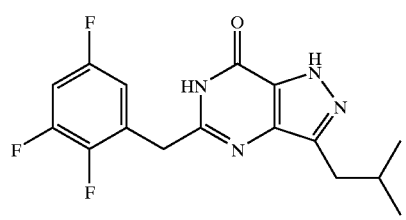 3-Isobutyl-5-(2,3,5-trifluoro-benzyl)-1,6-dihydro-pyrazolo[4,3-d]pyrimidin-7-one | 336.1 | 1.43 |
| 129 | 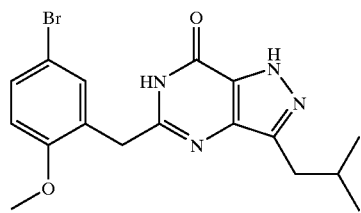 3-Isobutyl-5-(5-bromo-2-methoxy-benzyl)-1,6-dihydro-pyrazolo[4,3-d]pyrimidin-7-one | 390.1 | 1.53 |
| 130 | 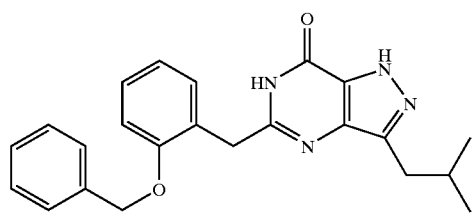 3-Isobutyl-5-(2-benzyloxy-benzyl)-1,6-dihydro-pyrazolo[4,3-d]pyrimidin-7-one | 388.2 | 1.64 |
| 131 | 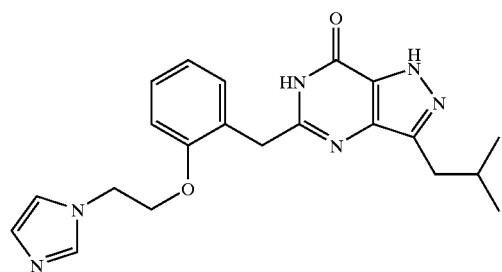 5-[2-(2-Imidazol-1-yl-ethoxy)-benzyl]-3-isobutyl-1,6-dihydro-pyrazolo[4,3-d]pyrimidin-7-one | 392.2 | 1.12 |

-continued

| | | | |
|---|---|---|---|
| 132 | 3-Isobutyl-5-(2,3,6-trichloro-benzyl)-1,6-dihydro-pyrazolo[4,3-d]pyrimidin-7-one | 384.0 | 1.66 |
| 133 | 3-Isobutyl-5-(3-benzyloxy-benzyl)-1,6-dihydro-pyrazolo[4,3-d]pyrimidin-7-one | 388.2 | 1.64 |
| 134 | 5-(2,3-Dihydro-benzofuran-5-ylmethyl)-3-isobutyl-1,6-dihydro-pyrazolo[4,3-d]pyrimidin-7-one | 324.2 | 1.25 |
| 135 | 3-Cyclopentyl-5-(2,4,5-trifluoro-benzyl)-1,6-dihydro-pyrazolo[4,3-d]pyrimidin-7-one | 348.1 | 1.51 |
| 136 | 3-Cyclopentyl-5-(2-methyl-benzyl)-1,6-dihydro-pyrazolo[4,3-d]pyrimidin-7-one | 308.2 | 1.52 |
| 137 | 3-Cyclopentyl-5-isobutyl-1,6-dihydro-pyrazolo[4,3-d]pyrimidin-7-one | 260.2 | 1.33 |

| | | | |
|---|---|---|---|
| 138 | 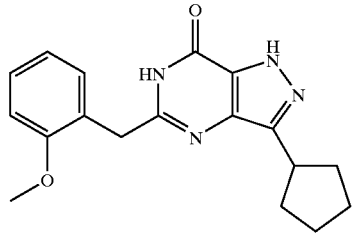 3-Cyclopentyl-5-(2-methoxy-benzyl)-1,6-dihydro-pyrazolo[4,3-d]pyrimidin-7-one | 324.2 | 1.44 |
| 139 | 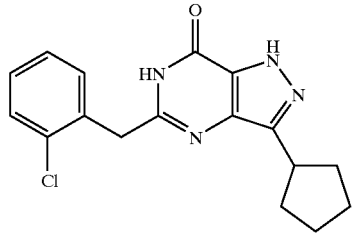 3-Cyclopentyl-5-(2-chloro-benzyl)-1,6-dihydro-pyrazolo[4,3-d]pyrimidin-7-one | 328.1 | 1.52 |
| 140 | 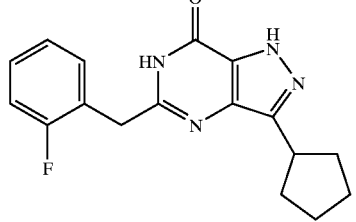 3-Cyclopentyl-5-(2-fluoro-benzyl)-1,6-dihydro-pyrazolo[4,3-d]pyrimidin-7-one | 312.1 | 1.42 |
| 141 | 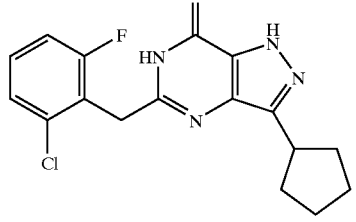 3-Cyclopentyl-5-(2-chloro-6-fluoro-benzyl)-1,6-dihydro-pyrazolo[4,3-d]pyrimidin-7-one | 346.1 | 1.53 |
| 142 | 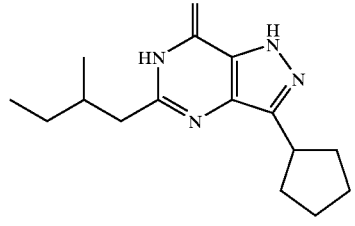 3-Cyclopentyl-5-(2-methyl-butyl)-1,6-dihydro-pyrazolo[4,3-d]pyrimidin-7-one | 274.2 | 1.49 |

-continued
| | | | |
|---|---|---|---|
| 143 | 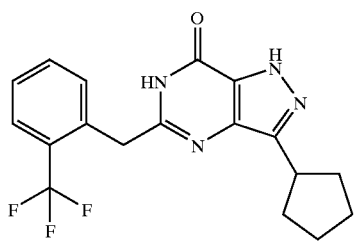 3-Cyclopentyl-5-(2-trifluoromethyl-benzyl)-1,6-dihydro-pyrazolo[4,3-d]pyrimidin-7-one | 362.1 | 1.62 |
| 144 | 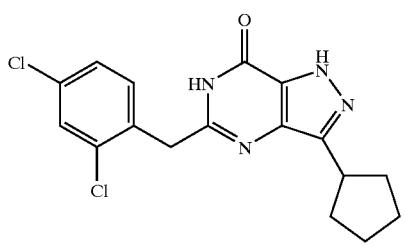 3-Cyclopentyl-5-(2,4-dichloro-benzyl)-1,6-dihydro-pyrazolo[4,3-d]pyrimidin-7-one | 362.1 | 1.70 |
| 145 | 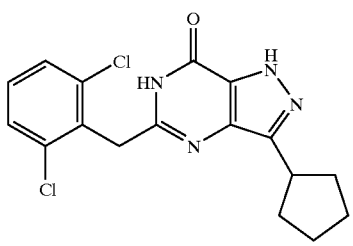 3-Cyclopentyl-5-(2,6-dichloro-benzyl)-1,6-dihydro-pyrazolo[4,3-d]pyrimidin-7-one | 362.1 | 1.61 |
| 146 | 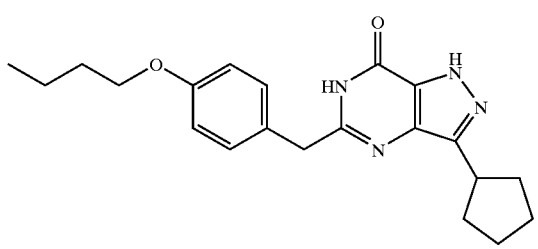 5-(4-Butoxy-benzyl)-3-cyclopentyl-1,6-dihydro-pyrazolo[4,3-d]pyrimidin-7-one | 366.2 | 1.80 |
| 147 | 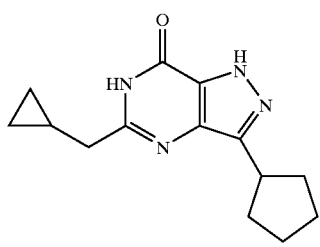 3-Cyclopentyl-5-cyclopropylmethyl-1,6-dihydro-pyrazolo[4,3-d]pyrimidin-7-one | 258.2 | 1.22 |

-continued
| | | | |
|---|---|---|---|
| 148 | 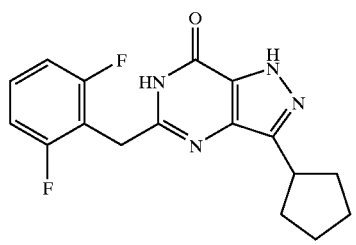<br>3-Cyclopentyl-5-(2,6-difluoro-benzyl)-1,6-dihydro-pyrazolo[4,3-d]pyrimidin-7-one | 330.1 | 1.44 |
| 149 | 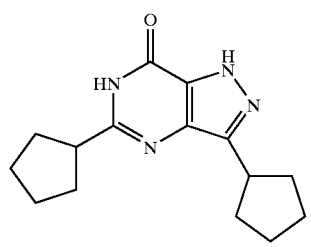<br>3,5-Dicyclopentyl-1,6-dihydro-pyrazolo[4,3-d]pyrimidin-7-one | 272.2 | 1.52 |
| 150 | 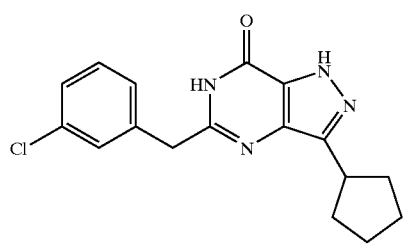<br>3-Cyclopentyl-5-(3-chloro-benzyl)-1,6-dihydro-pyrazolo[4,3-d]pyrimidin-7-one | 328.1 | 1.55 |
| 151 | 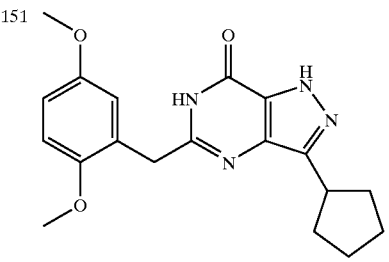<br>3-Cyclopentyl-5-(2,5-dimethoxy-benzyl)-1,6-dihydro-pyrazolo[4,3-d]pyrimidin-7-one | 354.2 | 1.41 |
| 152 | 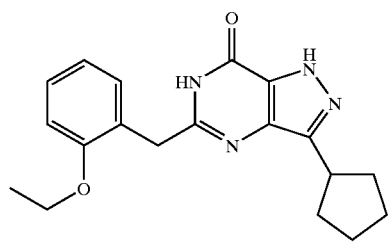<br>3-Cyclopentyl-5-(2-ethoxy-benzyl)-1,6-dihydro-pyrazolo[4,3-d]pyrimidin-7-one | 338.2 | 1.55 |

| | | | |
|---|---|---|---|
| 153 | 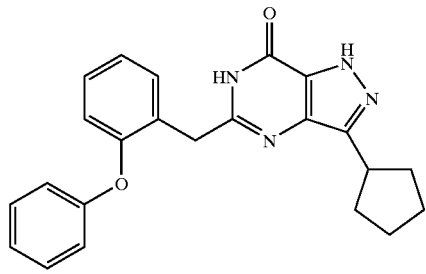 3-Cyclopentyl-5-(2-phenoxy-benzyl)-1,6-dihydro-pyrazolo[4,3-d]pyrimidin-7-one | 386.2 | 1.75 |
| 154 | 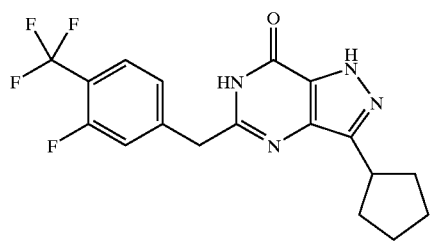 3-Cyclopentyl-5-(3-fluoro-4-trifluoromethyl-benzyl)-1,6-dihydro-pyrazolo[4,3-d]pyrimidin-7-one | 380.1 | 1.67 |
| 155 | 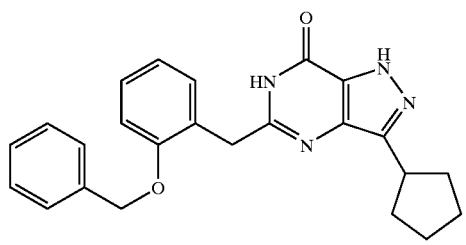 3-Cyclopentyl-5-(2-benzyloxy-benzyl)-1,6-dihydro-pyrazolo[4,3-d]pyrimidin-7-one | 400.2 | 1.73 |
| 156 | 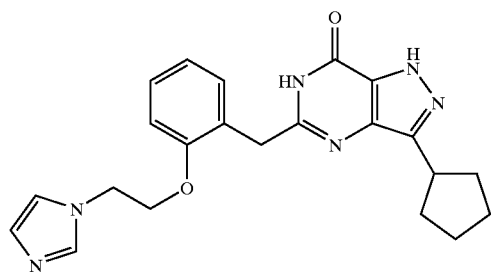 3-Cyclopentyl-5-[2-(2-imidazo-1-yl-ethoxy)-benzyl]-1,6-dihydro-pyrazolo[4,3-d]pyrimidin-7-one | 404.2 | 1.20 |
| 157 | 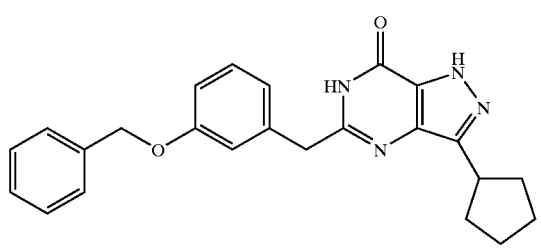 3-Cyclopentyl-5-(3-benzyloxy-benzyl)-1,6-dihydro-pyrazolo[4,3-d]pyrimidin-7-one | 400.2 | 1.73 |

| 158 | ![structure] 3-Cyclopentyl-5-propyl-1,6-dihydro-pyrazolo[4,3-d]pyrimidin-7-one | 246.2 | 1.19 |
| --- | --- | --- | --- |
| 159 | ![structure] 3-Cyclopentyl-5-(2,3-dihydro-benzofuran-5-ylmethyl)-1,6-dihydro-pyrazolo[4,3-d]pyrimidin-7-one | 336.2 | 1.35 |

EXAMPLE 160
3-Cyclopentyl-5-(2-trifluoromethoxy-benxyl)-1,6-dihydro-pyrazolo[4,3-d]pyrimidin-7-one.

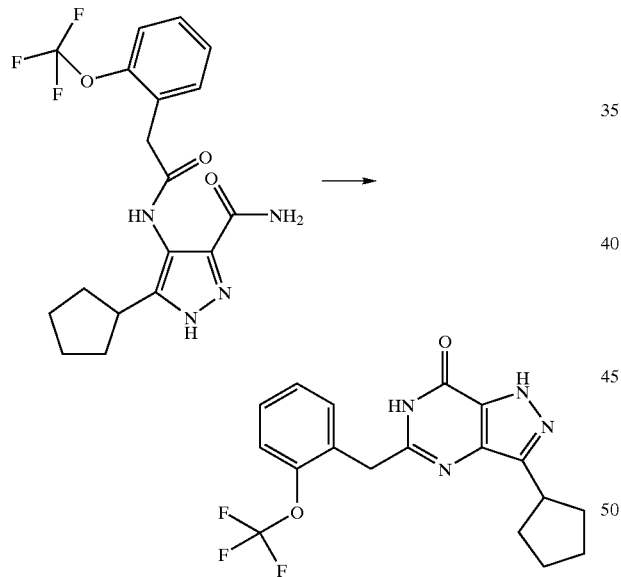

5-Cyclopentyl-4-[2-(2-trifluoromethoxy-phenyl)-acetylamino]-1H-pyrazole-3-carboxylic acid amide (120 mg, 0.303 mmol) and potassium tert-butoxide (102 mg, 0.909 mmol) were suspended in isopropylalcohol (5 ml) and the reaction was heated to reflux, under nitrogen, for 18 hours. The reaction mixture was concentrated under reduced pressure and the residue was partitioned between ethyl acetate (20 ml) and water (20 ml). The aqueous phase was removed, acidified to pH 2 with 2N HCl, and extracted with ethyl acetate (2×15 ml). The combined organic extracts were washed with saturated sodium carbonate solution (3×10 ml), dried over MgSO₄, concentrated under reduced pressure and the residue was purified by flash column chromatography on silica gel eluting with dichloromethane:methanol (95:5, by volume) to give 3-cyclopentyl-5-(2-trifluoromethoxy-benxyl)-1,6-dihydro-pyrazolo[4,3-d]pyrimidin-7-one (21 mg) as an off-white solid. $^1$H NMR (400 MHz, DMSO-d6): δ=7.36–7.41 (2H, m), 7.29–7.36 (2H, m), 3.97–4.03 (2H, brs), 2.39–2.45 (1H, m, partially masked by solvent), 1.82–1.94 (2H, m), 1.66–1.79 (2H, m), 1.58–1.65 (2H, m), 1.49–1.58 (2H, m) ppm. LRMS (electrospray): m/z [M−H]⁺ 377.

EXAMPLE 161
3-Isobutyl-5-(2-trifluoromethoxy-benxyl)-1,6-dihydro-pyrazolo[4,3-d]pyrimidin-7-one.

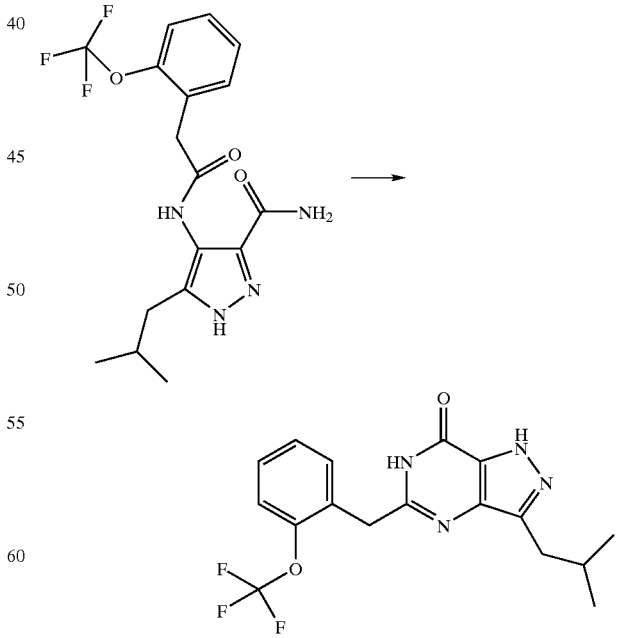

5-Isobutyl-4-[2-(2-trifluoromethoxy-phenyl)-acetylamino]-1H-pyrazole-3-carboxylic acid amide (140 mg, 0.365 mmol) and potassium tert-butoxide (123 mg, 1.09 mmol) were suspended in isopropylalcohol (6 ml) and the reaction was heated to reflux, under nitrogen, for 18 hours. The reaction mixture was concentrated under reduced pressure and the residue was partitioned between ethyl acetate (20 ml) and water (20 ml). The aqueous phase was removed, acidified to pH 2 with 2N HCl, and extracted with ethyl acetate (2×15 ml). The combined organic extracts were washed with saturated sodium carbonate solution (3×10 ml), dried over MgSO$_4$, concentrated under reduced pressure and the residue was purified by flash column chromatography on silica gel eluting with dichloromethane:methanol (95:5, by volume) to give 3-isobutyl-5-(2-trifluoromethoxy-benxyl)-1,6-dihydro-pyrazolo[4,3-d]pyrimidin-7-one (27 mg) as an off-white solid. $^1$H NMR (400 MHz, CDCl$_3$): δ=8.64–8.74 (1H, brs), 7.22–7.41 (4H, m, partially masked by solvent), 4.15 (2H, s), 2.79–2.84 (2H, d), 2.13–2.23 (1H, m), 0.92–1.00 (6H, d) ppm. LR (electrospray): m/z [M+H]$^+$ 367, [M–H]$^+$ 365.

EXAMPLE 162

3-Pyridin-3-yl-5-(2-trifluoromethoxy-benxyl)-1,6-dihydro-pyrazolo[4,3-d]pyrimidin-7-one.

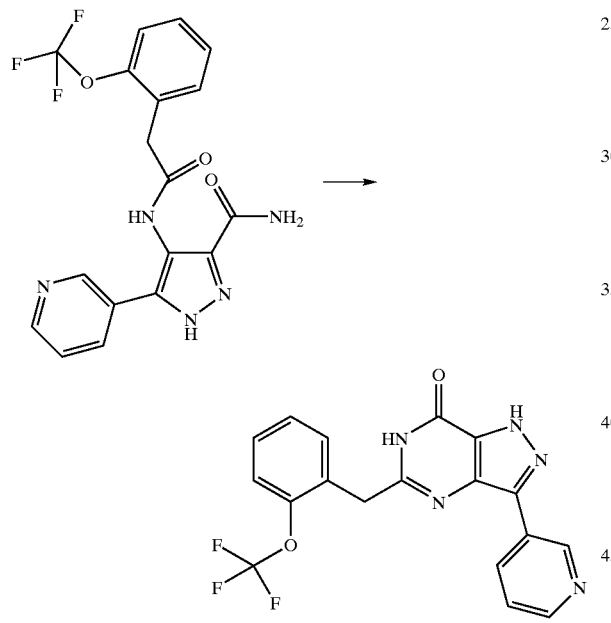

5-Pyridin-3-yl-4-[2-(2-trifluoromethoxy-phenyl)-acetylamino]-1H-pyrazole-3-carboxylic acid amide (345 mg, 0.85 mmol) and potassium tert-butoxide (286 mg, 2.55 mmol) were suspended in isopropylalcohol (5 ml) and the reaction was heated to 55° C. under nitrogen for 18 hours. The reaction mixture was concentrated under reduced pressure and the residue was partitioned between ethyl acetate (20 ml) and water (20 ml). The aqueous phase was removed, acidified to pH 2 with 2N HCl, and extracted with ethyl acetate (2×15 ml) and dichloromethane (2×15 ml). The combined organic extracts were dried over MgSO$_4$, concentrated under reduced pressure and the residue was purified by flash column chromatography on silica gel eluting with a solvent gradient of dichloromethane:methanol (99:1 changing to 95:5, by volume). The product was triturated with methanol (3 ml), dichloromethane (3 ml) and diethylether (3 ml) to give 3-pyridin-3-yl-5-(2-trifluoromethoxy-benxyl)-1,6-dihydro-pyrazolo[4,3-d]pyrimidin-7-one (13 mg) as an off-white solid. $^1$H NMR (400 MHz, CD$_3$OD): δ=9.34 (1H, brs), 8.57–8.61 (1H, d), 8.43–8.48 (1H, m), 7.32–7.47 (5H, m), 4.18 (2H, s) ppm. LRMS (electrospray): m/z [M–H]$^+$ 386.

Preparation 1
4-Methyl-3-oxo-pentanoic Acid Ethyl Ester.

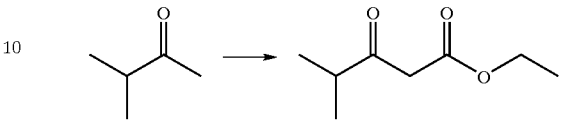

Sodium pellets (3.39 g, 148 mmol) were dissolved in ethanol (100 ml) under nitrogen at room temperature and a solution of diethyloxalate (20 ml, 147 mmol) in 3-methyl-2-butanone (18.9 ml, 177 mmol) was added dropwise at room temperature over 30 minutes. The reaction was diluted with ethanol (100 ml), heated to 60° C. and stirred at this temperature for 2 hours. After cooling to room temperature the reaction was poured onto ice-cold 2N HCl (200 ml) and extracted with diethylether (300 ml) and ethyl acetate (300 ml). The combined organic extracts were dried over MgSO$_4$, concentrated under reduced pressure and the residue was purified by flash column chromatography on silica gel eluting with a solvent gradient of pentane:ethyl acetate (99:1 changing to 95:5, by volume) to give 4-methyl-3-oxo-pentanoic acid ethyl ester (23.8 g) as a yellow oil. $^1$H NMR (400 MHz, CDCl$_3$): δ=14.40–14.80 (1H, brs), 6.40 (1H, s), 4.30–4.39 (2H, quart), 260–2.71 (1H, quin), 1.35–1.40 (3H, t), 1.15–1.20 (6H, d) ppm. LRMS (electrospray): m/z [M–H]$^+$ 185.

Preparation 2
5-Isopropyl-1H-pyrazol-3-carboxylic Acid Ethyl Ester.

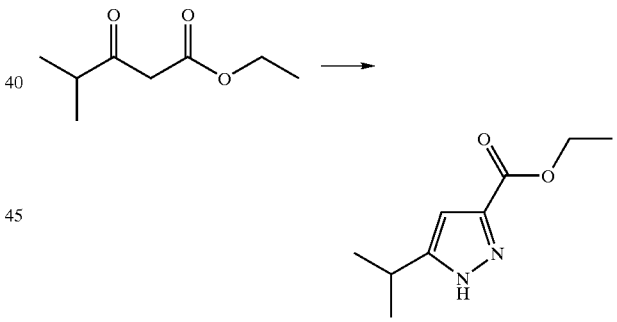

Hydrazine hydrate (6.6 ml, 134 mmol) was added to a solution of 4-methyl-3-oxo-pentanoic acid ethyl ester (23.8 g, 188 mmol) in ethanol (100 ml) at room temperature under nitrogen. The reaction was allowed to proceed at room temperature for 18 hours, and the solvent was removed under reduced pressure. The residue was partitioned between dichloromethane (300 ml) and water (300 ml) and the aqueous phase was removed. The organic phase was washed with water (2×200 ml), dried over MgSO$_4$ and concentrated under reduced pressure. The residue was purified by flash column chromatography on silica gel eluting with a solvent gradient of pentane:ethyl acetate (4:1 changing to 2:1, by volume) to give 5-isopropyl-1H-pyrazol-3-carboxylic acid ethyl ester (18.9 g) as a white solid. $^1$H NMR (400 MHz, CDCl$_3$): δ=10.80–10.95 (1H, brs), 6.61 (1H, s), 4.33–4.40 (2H, quart), 2.98–3.08 (1H, quin), 1.35–1.41 (3H, t), 1.24 ppm. LRMS (electrospray): m/z [M–H]$^+$ 181.

Preparation 3

5-Isopropyl-1H-pyrazol-3-carboxylic Acid.

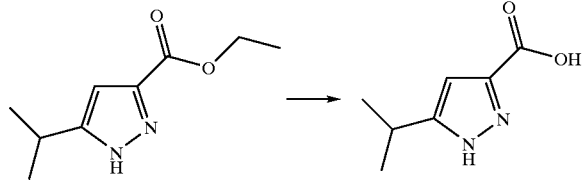

5-Isopropyl-1H-pyrazol-3-carboxylic acid ethyl ester (18.9 g, 104 mmol) and 1M NaOH solution (260 ml, 259 mmol) were dissolved in 1,4-dioxan (300 ml), the reaction was heated to 50° C. under nitrogen and stirred for 3 hours. The reaction mixture was cooled, adjusted to pH 2 using concentrated hydrochloric acid and the solvent was removed under reduced pressure. The residual solid was azeotroped with toluene (2×30 ml), dissolved in ethyl acetate (500 ml) and washed with water (200 ml). The aqueous phase was removed, extracted with ethyl acetate (2×200 ml) and the combined organic extracts were dried over $MgSO_4$. The solvent was removed under reduced pressure and the residue was azeotroped with dichloromethane (2×50 ml) to give 5-isopropyl-1H-pyrazol-3-carboxylic acid (14.7 g) as a white solid. $^1$H NMR (400 MHz, DMSO-D6): δ=12.50–13.30 (2H, brs), 6.42 (1H, s), 2.84–2.94 (1H, quin), 1.15–1.19 (6H, d) ppm. LRMS (electrospray) m/z $[M-H]^+$ 153.

Preparation 4

5-Isopropyl-4-nitro-1H-pyrazol-3-carboxylic Acid.

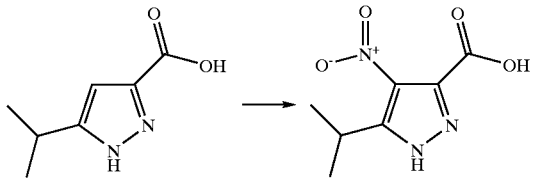

5-Isopropyl-1H-pyrazol-3-carboxylic acid (5 g, 32.5 mmol) was added portionwise to concentrated sulfuric acid (25 ml) at room temperature with stirring. The reaction mixture was then heated to 60° C. and concentrated nitric acid (70%, 6 ml, 90 mmol) was added dropwise, keeping the temperature at 60° C. The reaction was then stirred at 60° C. for 3 hours, cooled to room temperature and poured onto 50 ml of ice with stirring. After 15 minutes the white precipitate was isolated by filtration, washed with water and dried under reduced pressure to give 5-isopropyl-4-nitro-1H-pyrazol-3-carboxylic acid (5.2 g) as a white solid. $^1$H NMR (400 MHz, DMSO-D6): δ=13.86–13.93 (1H, brs), 13.50–13.80 (1H, brs), 3.39–3.52 (1H, m), 1.18–1.30 (6H, d) ppm. LRMS (electrospray): m/z $[M-H]^+$ 198.

Preparation 5

5-Isopropyl-4-nitro-1H-pyrazol-3-carboxylic Acid Amide.

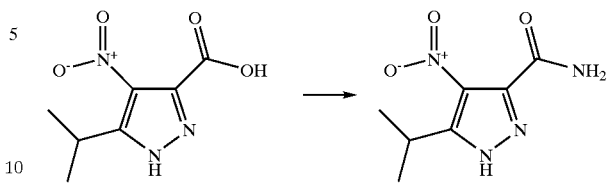

Oxalyl chloride (6.8 ml, 77.6 mmol) was added dropwise to a suspension of 5-isopropyl-4-nitro-1H-pyrazol-3-carboxylic acid (5.15 g, 25.9 mmol) in dichloromethane (80 ml) containing dimethylformamide (0.1 ml) under nitrogen at 0° C. The reaction was stirred at 0° C. for 1 hours, allowed to warm to room temperature and stirred for a further 2 hours. The solvent was removed under reduced pressure, the residue was dissolved in toluene (100 ml) and ammonia gas was bubbled into the solution for 2 hours. The reaction was stirred under nitrogen at room temperature for 18 hours, concentrated under reduced pressure and the residue was dissolved in hot methanol (300 ml). The resultant precipitate was filtered and the filtrate was concentrated under reduced pressure. The residue was azeotroped with water (300 ml), concentrated to approximately 80 ml under reduced pressure and the precipitate was isolated by filtration. This was washed with water and dried under to give 5-isopropyl-4-nitro-1H-pyrazol-3-carboxylic acid amide (3.1 g) as an orange solid. $^1$H NMR (400 MHz, DMSO-D6): δ=7.94–7.99 (1H, brs), 7.68-7.72 (1H, brs), 3.45–3.55 (1H, m), 1.24–1.30 (6H, d) ppm. LRMS (electrospray): m/z $[M+Na]^+$ 221, $[M-H]^+$ 197.

Preparation 6

4-Amino-5-isopropyl-1H-pyrazol-3-carboxylic Acid Amide.

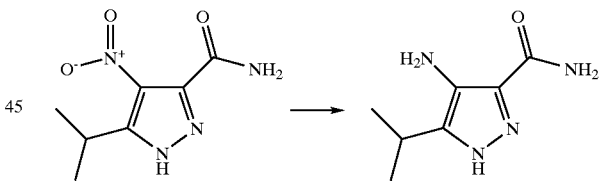

5-Isopropyl-4-nitro-1H-pyrazol-3-carboxylic acid amide (3 g, 15.1 mmol) and 10% palladium on carbon (500 mg) in ethanol (30 ml) were stirred under hydrogen (50 psi) at room temperature for 18 hours. The reaction mixture was filtered and the solid was washed with methanol (50 ml), dichloromethane (50 ml), ethanol (50 ml) and ethyl acetate (50 ml). The filtrate was concentrated under reduced pressure and the residue was purified by flash column chromatography on silica gel eluting with dichloromethane methanol (9:1, by volume) to give 4-amino-5-isopropyl-1H-pyrazol-3-carboxylic acid amide (2.6 g) as an off-white solid. $^1$H NMR (400 MHz, DMSO-D6): δ=12.20–12.30 (1H, brs), 7.02–7.14 (1H, brs), 6.85–6.95 (1H, brs), 4.30–4.46 (2H, brs), 2.90–3.00 (1H, m), 1.15–1.21 (6H, d) ppm. LRMS (electrospray): m/z $[M-H]^+$ 167, $[2M-H]^+$ 335. Anal. Found C, 49.86; H, 7.21; N, 33.07. $C_7H_{12}N_4O$ requires C, 49.99; H, 7.19; N, 33.31%.

Preparation 7
3-Oxo-heptanoic Acid Ethyl Ester.

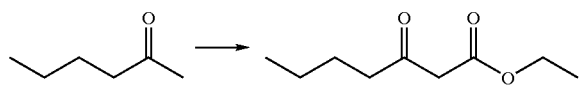

Sodium pellets (3.82 g, 166 mmol) were dissolved in ethanol (100 ml) under nitrogen at room temperature and a solution of diethyloxalate (22.6 ml, 166 mmol) hexan-2-one (20 g, 198 mmol) was added dropwise at room temperature over 30 minutes. The reaction was diluted with ethanol (100 ml), heated to 60° C. and stirred at this temperature for 2 hours. After cooling to room temperature the reaction was poured onto ice-cold 2N HCl (200 ml) and extracted with diethylether (300 ml) and ethyl acetate (300 ml). The combined organic extracts were dried over $MgSO_4$, concentrated under reduced pressure and the residue was purified by flash column chromatography on silica gel eluting with a solvent gradient of pentane:ethyl acetate (99:1 changing to 95:5, by volume) to give 3-oxo-heptanoic acid ethyl ester (30.3 g) as an orange oil. $^1H$ NMR (400 MHz, $CDCl_3$): δ=14.30–14.80 (1H, brs), 6.37 (1H, s), 4.30–4.39 (2H, quart), 2.43–2.50 (2H, t), 1.59–1.62 (2H, quin), 1.31–1.40 (5H, t+m), 0.86–0.97 (3H, t) ppm. LRMS (electrospray): m/z $[M-H]^+$ 199.

Preparation 8
5-Butyl-1H-pyrazol-3-carboxylic Acid Ethyl Ester.

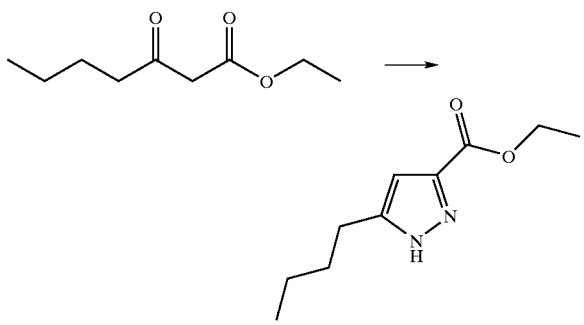

Hydrazine hydrate (7.75 ml, 157 mmol) was added dropwise to a solution of 3-oxo-heptanoic acid ethyl ester (30 g, 150 mmol) in ethanol (100 ml) at room temperature under nitrogen. The reaction was heated to 50° C. and allowed to proceed at this temperature for 18 hours, and the solvent was removed under reduced pressure. The residue was partitioned between dichloromethane (300 ml) and water (300 ml) and the aqueous phase was removed. The organic phase was washed with water (2×200 ml), dried over $MgSO_4$ and concentrated under reduced pressure. The residue was purified by flash column chromatography on silica gel eluting with pentane: ethyl acetate (8:1, by volume) to give 5-butyl-1H-pyrazol-3-carboxylic acid ethyl ester (24 g) as a yellow oil.

$^1H$ NMR (400 MHz, $CDCl_3$): δ=10.58–10.78 (1H, brs), 6.62 (1H, s), 4.35–4.40 (2H, quart), 2.63–2.70 (2H, t), 1.60–1.67 (2H, quin), 1.35–1.42 (5H, t+m), 0.90–0.96 (3H, t)ppm. LRMS (electrospray): m/z $[M-H]^+$ 195.

Preparation 9
5-Butyl-1H-pyrazol-3-carboxylic Acid.

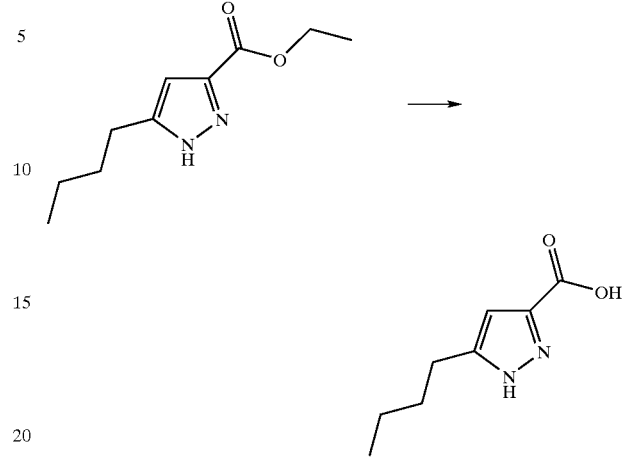

5-Butyl-1H-pyrazol-3-carboxylic acid ethyl ester (24 g, 122 mmol) and 1M NaOH solution (305 ml, 306 mmol) were dissolved in 1,4-dioxan (300 ml), the reaction was heated to 55° C. under nitrogen and stirred for 2 hours. The reaction mixture was cooled, adjusted to pH 2 using concentrated hydrochloric acid and the solvent was removed under reduced pressure. The residual solid was dissolved in ethyl acetate (300 ml) and washed with water (300 ml). The aqueous phase was removed, extracted with ethyl acetate (300 ml) and the combined organic extracts were dried over $MgSO_4$. The solvent was removed under reduced pressure and the residue was azeotroped with dichloromethane (2×50 ml) to give 5-butyl-1H-pyrazol-3-carboxylic acid (22.6 g) as a white solid. $^1H$ NMR (400 MHz, DMSO-D6): δ=12.50–13.00 (2H, brs), 6.41 (1H, s), 2.47–2.57 (2H, t), 1.46–1.56 (2H, quin), 1.19–1.29 (2H, sext), 1.15–1.19 (3H, t) ppm. LRMS (electrospray): m/z $[M-H]^+$ 167. Anal. Found C, 57.01; H, 7.23; N, 16.50. $C_8H_{12}N_2O_2$ requires C, 57.13; H, 7.19; N, 16.66%.

Preparation 10
5-Butyl-4-nitro-1H-pyrazol-3-carboxylic Acid.

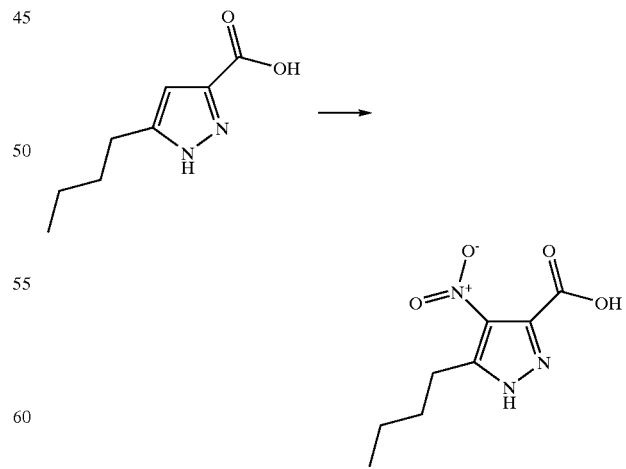

5-Butyl-1H-pyrazol-3-carboxylic acid (22.6 g, 134 mmol) was added portionwise to concentrated sulfuric acid (100 ml) at room temperature with stirring. The reaction mixture was then heated to 60° C. and concentrated nitric acid (70%, 23.7 ml, 376 mmol) was added dropwise, keeping the temperature at 60° C. The reaction was then stirred at 60° C. for 3 hours, cooled to room temperature and poured onto 50 ml of ice with stirring. After 15 minutes the pale yellow precipitate was isolated by filtration, washed with water and dried under reduced pressure to give 5-butyl-4-nitro-1H-pyrazol-3-carboxylic acid (21.9 g) as a pale yellow solid. $^1$H NMR (400 MHz, DMSO-D6): δ=2.83–2.92 (2H, t), 1.56–1.64 (2H, quin), 1.22–1.36 (2H, sext), 0.84–0.90 (3H, t) ppm. LRMS (electrospray): m/z [M–H]$^+$ 212. Anal. Found C, 30.19; H, 5.41; N, 13.12. $C_8H_{11}N_3O_4$. 6 mol $H_2O$ requires C, 29.91; H, 7.22; N, 13.08%.

Preparation 11
5-Butyl-4-nitro-1H-pyrazol-3-carboxylic Acid Amide.

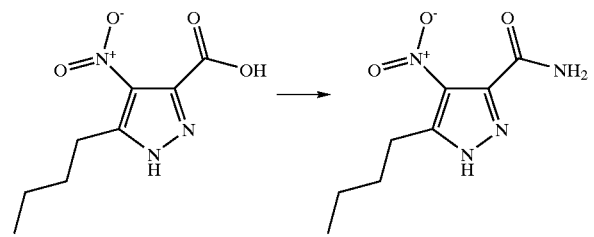

Oxalyl chloride (12.3 ml, 141 mmol) was added dropwise to a suspension of 5-butyl-4-nitro-1H-pyrazol-3-carboxylic acid (10 g, 46.9 mmol) in dichloromethane (100 ml) containing dimethylformamide (0.5 ml) under nitrogen at 0° C. The reaction was stirred at 0° C. for 1 hours, allowed to warm to room temperature and stirred for a further 2 hours. The solvent was removed under reduced pressure, the residue was dissolved in toluene (100 ml) and ammonia gas was bubbled into the solution for 2 hours. The reaction was stirred under nitrogen at room temperature for 18 hours, concentrated under reduced pressure and the residue was purified by flash column chromatography on silica gel eluting with dichloromethane:methanol (9:1, by volume) to give 5-butyl-4-nitro-1H-pyrazol-3-carboxylic acid amide (3.1 g) as an orange solid. $^1$H NMR (400 MHz, DMSO-D6): δ=7.87–7.96 (1H, brs), 7.57–7.66 (1H, brs), 2.83–2.90 (2H, t), 1.56–163 (2H, quin), 1.24–1.36 (2H, sext), 0.84–0.92 (3H, t) ppm. LRMS (electrospray): m/z [M–H]$^+$ 211. Anal. Found C, 44.66; H, 5.56; N, 25.50. $C_8H_{12}N_4O_3$.0.23 mol $H_2O$ requires C, 44.41; H, 580; N, 25.90%.

Preparation 12
4-Amino-5-butyl-1H-pyrazol-3-carboxylic Acid Amide.

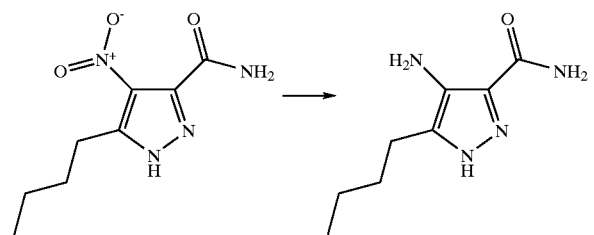

5-butyl-4-nitro-1H-pyrazol-3-carboxylic acid amide (3.1 g, 17.0 mmol) and 10% palladium on carbon (600 mg) in ethanol (50 ml) were stirred under hydrogen (50 psi) at room temperature for 18 hours. The reaction mixture was filtered and the solid was washed with methanol (50 ml), dichloromethane (50 ml), ethanol (50 ml) and ethyl acetate (50 ml). The filtrate was concentrated under reduced pressure and the residue was purified by flash column chromatography on silica gel eluting with a solvent gradient of dichloromethane:methanol (95:5 changing to 90:10, by volume) to give 4-amino-5-butyl-1H-pyrazol-3-carboxylic acid amide (2.37 g) as an an orange solid. $^1$H NMR (400 MHz, DMSO-D6): δ=12.24–12.32 (1H, brs), 7.02–7.14 (1H, brs), 6.80–6.95 (1H, brs 4.28–4.46 (2H, brs), 2.39–2.50 (2H, t, partially masked by solvent), 1.45–1.56 (2H, quin), 1.22–1.35 (2H, sext), 0.83–0.90 ppm. LRMS (electrospray): m/z [M–H]$^+$ 181, [2M–H]$^+$ 363. Anal. Found C, 52.58; H, 7.80; N, 30.56. $C_8H_{14}N_4O$ requires C, 52.73; H, 7.74; N, 30.75%.

Preparation 13
4,4-Dimethyl-3-oxo-pentanoic Acid Ethyl Ester.

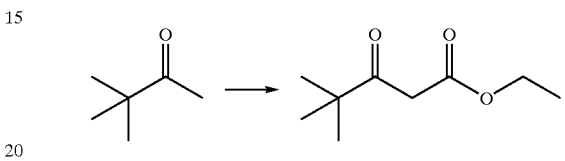

Sodium pellets (4.6 g, 200 mmol) were dissolved in ethanol (165 ml) under nitrogen at room temperature and a solution of diethyloxalate (27.2 ml, 200 mmol) in tert-butylmethyl ketone (20.1 g, 200 mmol) was added dropwise at room temperature over 15 minutes. The reaction was diluted with ethanol (100 ml), heated to 60° C. and stirred at this temperature for 2 hours. After cooling to room temperature the reaction was stirred for 64 hours, poured onto ice-cold 2N HCl (200 ml) and extracted with diethylether (3×200 ml). The combined organic extracts were washed with water, dried over $MgSO_4$ and concentrated under reduced pressure to give 4,4-dimethyl-3-oxo-pentanoic acid ethyl ester (36.7 g) as a yellow oil. $^1$H NMR (400 MHz, $CDCl_3$): δ=6.48 (1H, s), 4.26–4.37 (2H, quart), 1.29–1.38 (3H, t), 1.17 (9H, s) ppm. LRMS (electrospray): m/z [M+Na]$^+$ 223, [M–H]$^+$ 199.

Preparation 14
5-tert-Butyl-1H-pyrazol-3-carboxylic Acid Ethyl Ester.

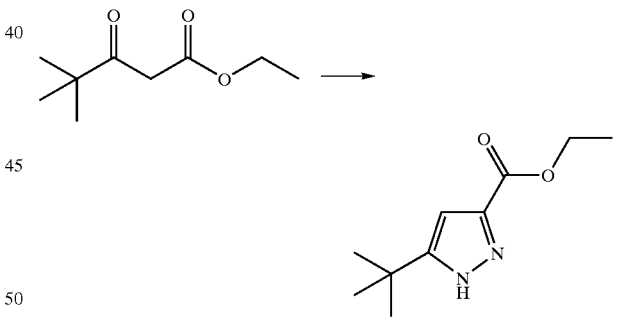

Hydrazine hydrate (9.5 ml, 180 mmol) was added to a solution of 4,4-dimethyl-3-oxo-pentanoic acid ethyl ester (36.7 g, 180 mmol) in ethanol (188 ml) at room temperature under nitrogen. The reaction was allowed to proceed at room temperature for 2 hours, and the solvent was removed under reduced pressure. The residue was partitioned between dichloromethane (500 ml) and water (400 ml) and the aqueous phase was removed. The organic phase was washed with brine (200 ml), dried over $MgSO_4$ and concentrated under reduced pressure to give 5-tert-butyl-1H-pyrazol-3-carboxylic acid ethyl ester (30.6 g) as a white solid. $^1$H NMR (400 MHz, $CDCl_3$): δ=14.50–14.90 (1H, brs), 6.45 (1H, s), 4.25–4.31 (2H, quart), 1.27–1.36 (3H, t), 1.16 (9H, s) ppm. LRMS (thermospray): m/z [M+H]$^+$ 197. Anal. Found C, 61.12; H, 8.20; N, 14.28. $C_{10}H_{16}N_2O$ requires C, 61.20; H, 8.22; N, 14.27%.

Preparation 15

5-tert-Butyl-1H-pyrazol-3-carboxylic Acid.

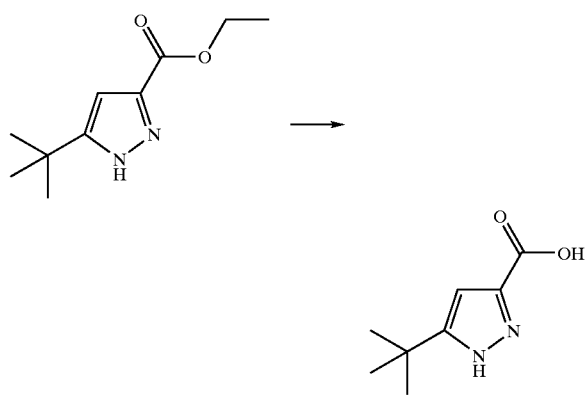

5-tert-Butyl-1H-pyrazol-3-carboxylic acid ethyl ester (20 g, 100 mmol) and 1M NaOH solution (250 ml, 250 mmol) were dissolved in 1,4-dioxan (300 ml), the reaction was heated to 60° C. under nitrogen and stirred for 2.5 hours. The reaction was then cooled to room temperature and stirred for a further 18 hours. The reaction mixture was adjusted to pH 2 using concentrated hydrochloric acid, extracted with ethyl acetate (4×200 ml) and the combined organic extracts washed with brine (100 ml). The organic phase was dried over MgSO$_4$ and the solvent was removed under reduced pressure to give 5-tert-butyl-1H-pyrazol-3-carboxylic acid (14.7 g) as a pale yellow solid. $^1$H NMR (400 MHz, DMSO-D6): δ=12.80–12.88 (2H, brs), 6.41 (1H, s), 1.11 (9H, s) ppm. LRMS (electrospray): m/z [M+H]$^+$ 169, [M+Na]$^+$ 191, [M−H]$^+$ 167.

Preparation 16

5-tert-Butyl-4-nitro-1H-pyrazol-3-carboxylic Acid.

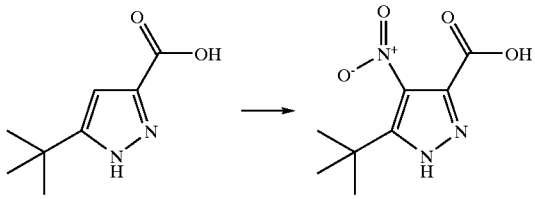

5-tert-Butyl-1H-pyrazol-3-carboxylic acid (5 g, 29.7 mmol) was added portionwise to concentrated sulfuric acid (25 ml) at room temperature with stirring. The reaction mixture was then heated to 60° C. and concentrated nitric acid (70%, 5.15 ml) was added dropwise, keeping the temperature at 60° C. The reaction was then stirred at 60° C. for 2.5 hours, cooled to room temperature and poured onto 50 ml of ice with stirring. After 15 minutes the white precipitate was isolated by filtration, washed with water and dried under reduced pressure to give 5-tert-butyl-4-nitro-1H-pyrazol-3-carboxylic acid (6.0 g) as a white solid. $^1$H NMR (400 MHz, DMSO-D6): δ=13.50–13.88 (2H, brs), 1.13 (9H, s) ppm. LRMS (electrospray): m/z [M+Na]$^+$ 236, [M−H]$^+$ 212.

Preparation 17

5-tert-Butyl-4-nitro-1H-pyrazol-3-carboxylic Acid Amide.

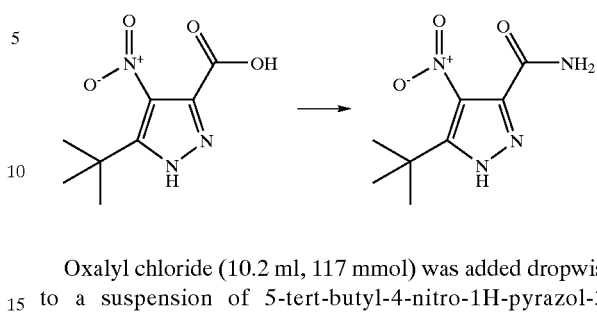

Oxalyl chloride (10.2 ml, 117 mmol) was added dropwise to a suspension of 5-tert-butyl-4-nitro-1H-pyrazol-3-carboxylic acid (6 g, 28 mmol) in dichloromethane (55 ml) containing dimethylformamide (0.1 ml) under nitrogen at 0° C. The reaction was stirred at 0° C. for 0.5 hours, allowed to warm to room temperature and stirred for a further 1.5 hours. The solvent was removed under reduced pressure, the residue was azeotroped with dichloromethane (50 ml) and the residue was dissolved in dichloromethane (100 ml). Ammonia gas was bubbled into the solution for 45 minutes and the reaction was stirred under nitrogen at room temperature for 18 hours, concentrated under reduced pressure and the residue was dissolved in ethyl acetate (250 ml). After washing with water (100 ml) and brine (100 ml) the organic phase was filtered, the filtrate was dried over MgSO$_4$ and concentrated under reduced pressure to give 5-tert-butyl-4-nitro-1H-pyrazol-3-carboxylic acid amide (4.0 g) as a light brown solid. $^1$H NMR (400 MHz, DMSO-D6): δ=12.90–13.08 (1H, brs), 7.78–7.86 (1H, brs), 7.49–7.60 (1H, brs), 1.30 (9H, s) (electrospray): m/z [M+H]$^+$ 213, [M+Na]$^+$ 235, [M−H]$^+$ 211.

Preparation 18

4-Amino-5-tert-butyl-1H-pyrazol-3-carboxylic Acid Amide.

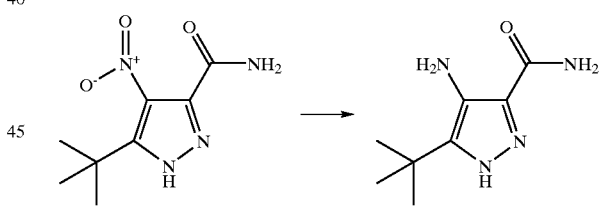

5-tert-Butyl-4-nitro-1H-pyrazol-3-carboxylic acid amide (4.6 g, 21 mmol) and 10% palladium on carbon (300 mg) in ethanol (80 ml) was stirred under hydrogen (60 psi) at room temperature for 18 hours. The reaction mixture was filtered and the filtrate was concentrated under reduced pressure. The residue was pre-absorbed onto silica gel and purified by flash column chromatography eluting with a solvent gradient of dichloromethane: methanol (100:0 changing to 95:5 then 90:10, by volume) to give 4-amino-5-tert-butyl-1H-pyrazol-3-carboxylic acid amide (2.96 g) as an off-white solid, which was a mixture of rotamers. $^1$H NMR (400 MHz, DMSO-D6): δ=12.10–12.20 (0.75H, brs), 11.75–11.85 (0.25H, brs), 7.04–7.16 (1.5H, brs), 6.88–6.96 (0.5H, brs), 4.27–4.59 (2H, 2×brs), 1.12 (9H, s) ppm. LRMS (electrospray): m/z [M+H]$^+$ 183, [M+Na]$^+$ 205, [M−H]$^+$ 181. Anal. Found C, 52.45; H, 7.84; N, 30.62. $C_8H_{14}N_4O$ requires C, 52.73; H, 7.74; N, 30.75%.

Preparation 19

5-Methyl-3-oxo-hexanoic Acid Ethyl Ester.

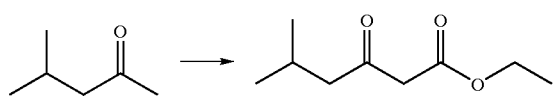

Sodium pellets (4.6 g, 200 mmol) were dissolved in ethanol (165 ml) under nitrogen at room temperature and a solution of diethyloxalate (13.5 ml, 100 mmol) in isobutyl-methyl ketone (30 ml, 200 mmol) was added dropwise at room temperature over 20 minutes. The reaction was heated to 60° C. and stirred at this temperature for one hour. After cooling to room temperature the reaction was poured onto ice-cold 2N HCl (200 ml) and extracted with diethylether (4×200 ml). The combined organic extracts were washed with water, dried over $MgSO_4$ and concentrated under reduced pressure to give 5-methyl-3-oxo-hexanoic acid ethyl ester (20 g) as a yellow oil. $^1$H NMR (400 MHz, $CDCl_3$): δ=14.40–14.70 (1H, brs), 6.27 (1H, s), 4.25–4.32 (2H, quart), 2.26–2.31 (2H, d) (1H, m), 1.29–1.34 (3H, t), 0.89–0.94 (6H, d) ppm. LRMS (thermospray): m/z $[M+NH_4]^+$ 218.

Preparation 20

5-Isobutyl-1H-pyrazol-3-carboxylic Acid Ethyl Ester.

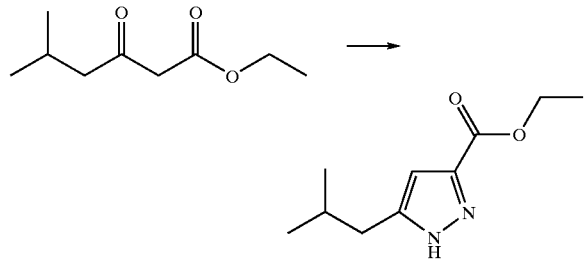

Hydrazine hydrate (5.7 ml, 115 mmol) was added to a solution of 5-methyl-3-oxo-hexanoic acid ethyl ester (22 g, 110 mmol) in ethanol (113 ml) at room temperature under nitrogen. The reaction was allowed to proceed at room temperature for 18 hours, and the solvent was removed under reduced pressure. The residue was partitioned between dichloromethane (400 ml) and water (400 ml) and the aqueous phase was removed. The organic phase was washed with brine (200 ml), water (200 ml), dried over $MgSO_4$ and concentrated under reduced pressure. The residue was purified by flash column chromatography on silica gel eluting with a solvent gradient of pentane: ethyl acetate (1:0 changing to 6:1, 5:1, 4:1, 3:1, 2:1 and finally 1:1, by volume) to give 5-isobutyl-1H-pyrazol-3-carboxylic acid ethyl ester (16.5 g) as a white solid. $^1$H NMR (400 MHz, $CDCl_3$): δ=11.60–12.60 (1H, brs), 6.53 (1H, s), 4.26–4.35 (2H, quart), 2.48–254 (2H; d), 1.80–1.90 (1H, m), 1.25–1.31 (3H, t), 0.81–0.88 (6H, d) ppm. LRMS (thermospray): m/z $[M+H]^+$ 197, $[2M+H]^+$ 393. Anal. Found C, 61.49; H, 8.30; N, 14.24. $C_{10}H_{16}N_2O_2$ requires C, 61.20; H, 8.22; N, 14.27%.

Preparation 21
5-Isobutyl-1H-pyrazol-3-carboxylic Acid.

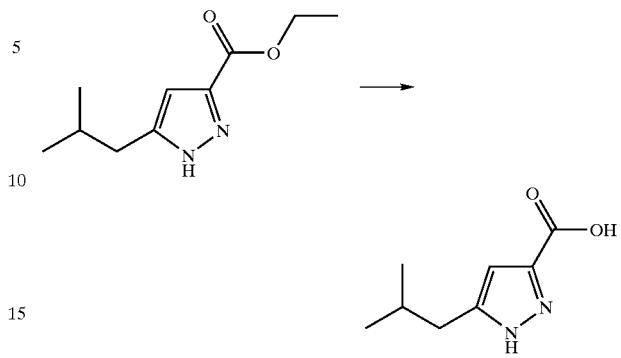

5-Isobutyl-1H-pyrazol-3-carboxylic acid ethyl ester (16.2 g, 83 mmol) and 1M NaOH solution (173 ml, 173 mmol) were dissolved in 1,4-dioxan (260 ml) and the reaction was stirred at room temperature under nitrogen for 64 hours. The reaction mixture was adjusted to pH 7 using concentrated hydrochloric acid, and concentrated under reduced pressure. Water (500 ml) was added, the slurry was adjusted to pH 1 with concentrated hydrochloric acid and the aqueous phase was extracted with ethyl acetate (5×300 ml). The combined organic extracts were dried over $MgSO_4$ and the solvent was removed under reduced pressure to give 5-isobutyl-1H-pyrazol-3-carboxylic acid (10 g) as a white solid. $^1$H NMR (400 MHz, DMSO-D6): δ=12.72–12.90 (1H, brs), 6.39 (1H, s), 2.39–2.43 (2H, d), 1.77–1.86 (1H, m), 0.78–0.83 (6H, d) ppm. LRMS (electrospray): m/z $[M+Na]^+$ 191, $[2M+Na]^+$ 359, $[M-H]^+$ 167, $[2M-H]^+$ 335.

Preparation 22
5-Isobutyl-4-nitro-1H-pyrazol-3-carboxylic Acid.

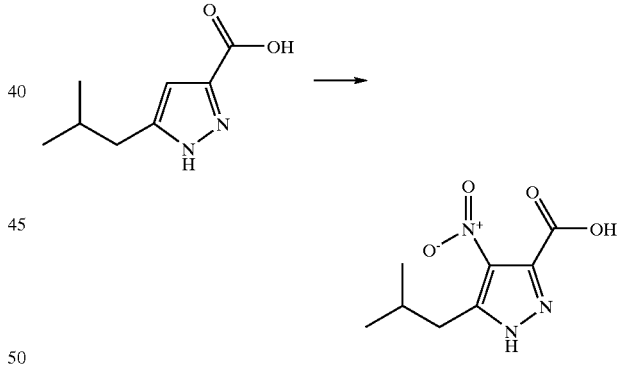

5-Isobutyl-1H-pyrazol-3-carboxylic acid (5 g, 29.7 mmol) was added portionwise to concentrated sulfuric acid (25 ml) at room temperature with stirring. The reaction mixture was then heated to 60° C. and concentrated nitric acid (70%, 5.15 ml) was added dropwise, keeping the temperature at 60° C. The reaction was then stirred at 60° C. for 3 hours, cooled to room temperature and poured onto 50 ml of ice with stirring. The resultant white precipitate was isolated by filtration, washed with water and dried under reduced pressure to give 5-isobutyl-4-nitro-1H-pyrazol-3-carboxylic acid (6.4 g) as a white solid. $^1$H NMR (400 MHz, DMSO-D6): δ=2.71–2.76 (2H, d), 1.88–2.00 (1H, m), 0.80–0.87 (6H, d) ppm. LRMS (thermospray): m/z $[M+NH_4]^+$ 231, $[M-H]^+$ 212. LRMS (electrospray): m/z $[M-H]^+$ 212, $[2M-H]^+$ 425. Anal. Found C, 42.54; H, 5.18; N, 18.63. $C_8H_{11}N_3O_4$. 0.7 mol $H_2O$ requires C, 42.55; H, 5.54; N, 18.61%.

Preparation 23
5-Isobutyl-4-nitro-1H-pyrazol-3-carboxylic Acid Amide.

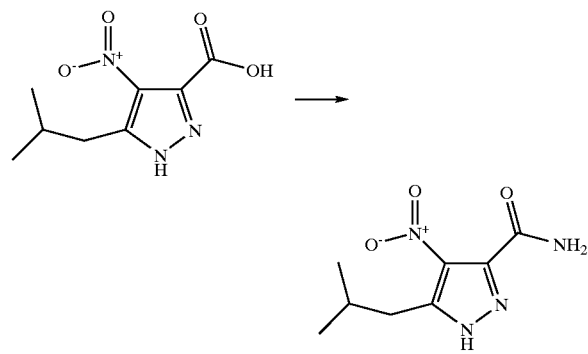

Oxalyl chloride (10 ml, 115 mmol) was added dropwise to a suspension of 5-isobutyl-4-nitro-1H-pyrazol-3-carboxylic acid (5.6 g, 26 mmol) in dichloromethane (70 ml) containing dimethylformamide (0.1 ml) under nitrogen at 0° C. The reaction was stirred at 0° C. for 0.5 hours, allowed to warm to room temperature and stirred for a further 2 hours. The solvent was removed under reduced pressure, the residue was azeotroped with dichloromethane (3×50 ml) and the residue was dissolved in toluene (100 ml). Ammonia gas was bubbled into the solution for 2 hours and the reaction was stirred under nitrogen at room temperature for 18 hours, concentrated under reduced pressure and the residue was suspended in methanol (250 ml). After filtration, the filtrates were concentrated under reduced pressure, the residue was dissolved in ethyl acetate (400 ml) and washed with water (50 ml). The organic phase was filtered, the filtrate was dried over $MgSO_4$ and concentrated under reduced pressure. The filtered solid and residue from the filtrates were combined to give 5-isobutyl-4-nitro-1H-pyrazol-3-carboxylic acid amide (4.8 g) as an off-white solid. $^1$H NMR (400 MHz, DMSO-D6): δ=13.61–13.81 (1H, brs), 7.80–7.96 (1H, brs), 7.50–7.66 (1H, brs), 2.70–2.76 (2H, d), 1.90–2.01 (1H, m), 0.83–0.88 (6H, d) ppm. LRMS (electrospray): m/z [M+Na]$^+$ 235, [2M+Na]$^+$ 447, [M−H]$^+$ 211, [2M−H]$^+$ 423. Anal. Found C, 45.12; H, 5.68; N, 26.31. $C_8H_{12}N_4O_3$ requires C, 45.28; H, 5.70; N, 26.40%.

Preparation 24
4-Amino-5-isobutyl-1H-pyrazol-3-carboxylic Acid Amide.

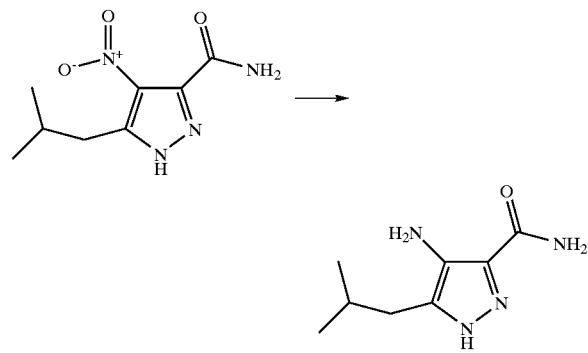

5-Isobutyl-4-nitro-1H-pyrazol-3-carboxylic acid amide (4.7 g, 22 mmol) and 10% palladium on carbon (300 mg) in ethanol (80 ml) was stirred under hydrogen (60 psi) at room temperature for 4 hours, and held under nitrogen for 64 hours. The reaction mixture was filtered and the filtrate was concentrated under reduced pressure of dichloromethane:methanol (100:0 changing to 95:5 then 90:10, by volume) to give 4-amino-5-isobutyl-1H-pyrazol-3-carboxylic acid amide (3.8 g) as an off-white solid, which was a mixture of rotamers. $^1$H NMR (400 MHz, DMSO-D6): δ=12.20–12.28 (1H, brs), 7.00–7.10 (1.34H, brs), 6.80–6.85 (0.66H, brs), 4.27–4.40 (2H, brs), 2.27–2.36 (2H, d), 1.78–1.88 (1H, m), 0.77–0.84 (6H, d) ppm. LRMS (electrospray): m/z [M+H]$^+$ 183, [M+Na]$^+$ 205. Anal. Found C, 52.27; H, 7.78; N, 30.59. $C_8H_{14}N_4O$ requires C, 52.73; H, 7.76; N, 30.75%.

Preparation 25
1-Cyclopentylethanone.

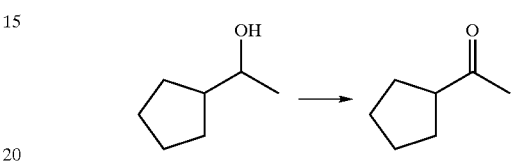

Concentrated sulfuric acid (22.4 ml, 420 mmol) was slowly added to a solution of chromium trioxide (26.3 g, 263 mmol) dissolved in water (50 ml) at room temperature. After 10 min this solution was added to 1-cyclopentylethanol (20 g, 175 mmol) dissolved in acetone (450 ml) maintaining the temperature below 35° C. The addition was continued until a bright orange colour persisted for 10 minutes. The reaction mixture was quenched with isopropyl alcohol to destroy excess chromic acid and it was then neutralised to pH 5 with the portionwise addition of sodium bicarbonate. After filtration the filtrate was concentrated under reduced pressure (to 50 ml) and extracted with diethylether (3×300 ml). The combined organic extracts were dried over $MgSO_4$ and concentrated under reduced pressure to give 1-cyclopentylethanone (16.7 g) as a colourless oil. $^1$H NMR (400 MHz, $CDCl_3$): δ 2.80–2.90 (1H, quin), 2.18 (3H, s), 1.53–1.86 (8H, 2×m) ppm.

Preparation 26
3-Cyclopentyl-3-oxo-propionic Acid Ethyl Ester.

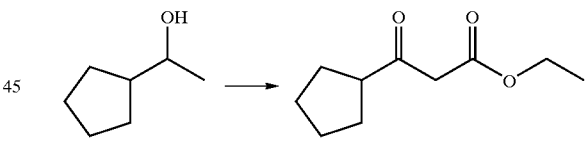

Sodium pellets (3.1 g, 135 mmol) were dissolved in ethanol (100 ml) under nitrogen at room temperature and a solution of diethyloxalate (18.4 ml, 135 mmol) and 1-cyclopentylethanone (16.7 g, 149 mmol) was added dropwise at room temperature over 30 minutes. The reaction was diluted with ethanol (100 ml), heated to 60° C. and stirred at this temperature for 2 hours. After cooling to room temperature the reaction was poured onto ice-cold 2N HCl (200 ml) and extracted with diethylether (300 ml) and ethyl acetate (300 ml). The combined organic extracts were dried over $MgSO_4$, concentrated under reduced pressure and the residue was purified by flash column chromatography on silica gel eluting with pentane:ethyl acetate (6:1, by volume) to give 3-cyclopentyl-3-oxo-propionc acid ethyl ester (23.8 g) as an orange oil. $^1$H NMR (400 MHz, $CDCl_3$): δ=14.38–14.65 (1H, brs), 6.83 (1H, s), 4.30–4.39 (2H, quart), 2.82–2.92 (1H, quin), 1.83–1.96 (2H, m), 1.57–1.83 (6H, 2×m), 1.33–1.40 (3H, t) ppm. LRMS (electrospray): m/z [M−H]$^+$ 211.

Preparation 27
5-Cyclopentyl-1H-pyrazol-3-carboxylic Acid Ethyl Ester.

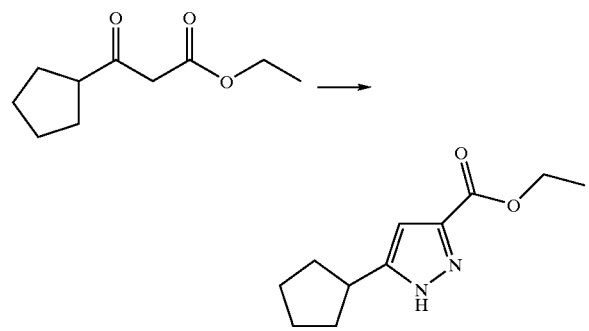

Hydrazine hydrate (5.8 ml, 117 mmol) was added to a solution of 3-cyclopentyl-3-oxo-propionc acid ethyl ester (23.7 g, 112 mmol) in ethanol (100 ml) at room temperature under nitrogen. The reaction was allowed to proceed at room temperature for 18 hours, then heated to 50° C. and held at this temperature for 4 hours. The solvent was removed under reduced pressure and the residue was partitioned between dichloromethane (300 ml) and water (300 ml) and the aqueous phase was removed. The organic phase was washed with water (2×200 ml), dried over MgSO$_4$ and concentrated under reduced pressure. The residue was purified by flash column chromatography on silica gel eluting with a solvent gradient of pentane: ethyl acetate (4:1, by volume) to give 5-cyclopentyl-1H-pyrazol-3-carboxylic acid ethyl ester (17.1 g) as a pale yellow solid. $^1$H NMR (400 MHz, CDCl$_3$): δ=10.40–10.60 (1H, brs), 6.58 (1H, s), 4.30–4.38 (2H, quart), 3.01–3.10 (1H, quin), 2.00–2.10 (2H, m), 1.56–1.80 (6H, 2×m), 1.33–1.39 (3H, t) ppm. LRMS (electrospray): m/z [M+H]$^+$ 209, [M+Na]$^+$ 231. Anal. Found C, 63.40; H, 7.75; N, 13.41. C$_{11}$H$_{16}$N$_2$O$_2$ requires C, 63.44; H, 7.74; N, 13.45%.

Preparation 28
5-Cyclopentyl-1H-pyrazol-3-carboxylic Acid.

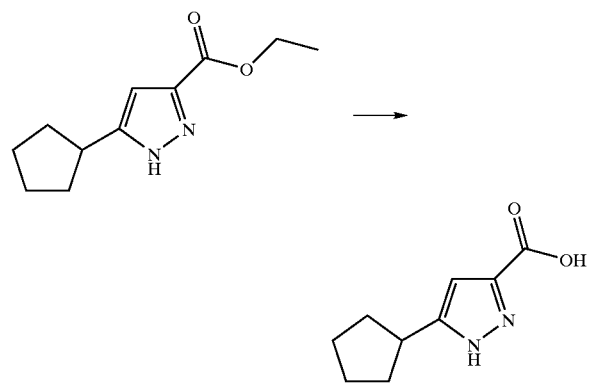

5-Cyclopentyl-1H-pyrazol-3-carboxylic acid ethyl ester (17.1 g, 82 mmol) and 1M NaOH solution (205 ml, 205 mmol) were dissolved in 1,4-dioxan (300 ml) and the reaction was heated to 50° C. under nitrogen and stirred for 3 hours. The reaction mixture was cooled, adjusted to pH 2 using concentrated hydrochloric acid and the solvent was removed under reduced pressure. The residual solid was azeotrped with toluene (2×30 ml), dissolved in ethyl acetate (500 ml) and washed with water (200 ml). The aqueous phase was removed, extracted with ethyl acetate (2×200 ml) and the combined organic extracts were dried over MgSO$_4$. The solvent was removed under reduced pressure and the residue was azeotrped with dichloromethane (2×50 ml) to give 5-cyclopentyl-1H-pyrazol-3-carboxylic acid (13 g) as a white solid. $^1$H NMR (400 MHz, DMSO-D6): δ=12.75–12.88 (2H, brs), 6.43 (1H, s), 2.97–3.08 (1H, quin), 1.91–2.02 (2H, m), 1.50–1.76 (6H, 2×m) ppm. LRMS (electrospray): m/z [M–H]$^+$ 179. Anal. Found C, 59.72; H, 6.74; N, 15.37. C$_9$H$_{12}$N$_2$ requires C, 59.99; H, 6.71; N, 15.55%.

Preparation 29
5-Cyclopentyl-4-nitro-1H-pyrazol-3-carboxylic Acid.

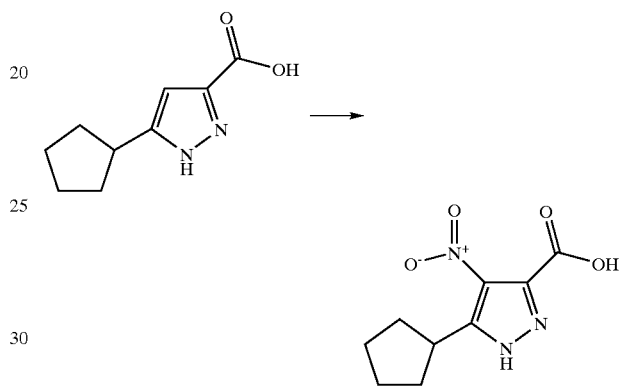

5-Cyclopentyl-1H-pyrazol-3-carboxylic acid (13 g, 72.1 mmol) was added portionwise to concentrated sulfuric acid (75 ml) at room temperature with stirring. The reaction mixture was then heated to 60° C. and concentrated nitric acid (70%, 12.7 ml, 202 mmol) was added dropwise, keeping the temperature at 60° C. The reaction was then stirred at 60° C. for 3 hours, cooled to room temperature and poured onto 50 ml of ice with stirring. After 15 minutes the precipitate was isolated by filtration, washed with water and dried under reduced pressure to give 5-cyclopentyl-4-nitro-1H-pyrazol-3-carboxylic acid (7.1 g) as a yellow solid. $^1$H NMR (400 MHz, DMSO-D6): δ=14.00–14.41 (1H, brs), 13.28–13.85 (1H, brs), 3.20–3.56 (1H, brs, partially masked by solvent), 1.96–2.10 (2H, m), 1.54–1.80 (6H, 2×m) ppm. LRMS (electrospray): m/z [M–H]$^+$ 224, [2M–H]$^+$ 449. Anal. Found C, 43.83; H, 5.35; N, 16.94. C$_9$H$_{11}$N$_3$O$_4$. 1.2 mol H$_2$O requires C, 43.80; H, 5.47; N, 17.02%.

Preparation 30
5-Cyclopentyl-4-nitro-1H-pyrazol-3-carboxylic Acid Amide.

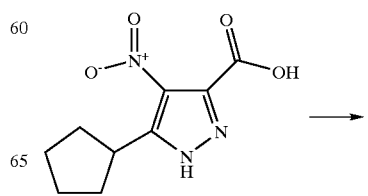

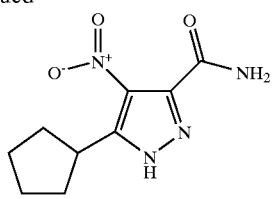

Oxalyl chloride (7.65 ml, 87.7 mmol) was added dropwise to a suspension of 5-isopropyl-4-nitro-1H-pyrazol-3-carboxylic acid (6.58 g, 29.2 mmol) in dichloromethane (100 ml) containing dimethylformamide (0.5 ml) under nitrogen at 0° C. The reaction was stirred at 0° C. for 1 hours, allowed to warm to room temperature and stirred for a further 2 hours. The solvent was removed under reduced pressure, the residue was azeotroped with dichloromethane (2×50 ml) and dissolved in toluene (100 ml). Ammonia gas was bubbled into the solution for 2 hours and the reaction was stirred under nitrogen at room temperature for 18 hours, concentrated under reduced pressure and purified by flash column chromatography on silica gel eluting with a solvent gradient of dichloromethane:methanol (95:5 changing to 90:10, by volume) to give 5-cyclopentyl-4-nitro-1H-pyrazol-3-carboxylic acid amide (5.48 g) as a yellow solid. $^1$H NMR (400 MHz, DMSO-D6): δ=13.67–13.79 (1H, brs), 7.88–8.03 (1H, brs), 7.59–7.77 (1H, brs), 3.46–3.60 (1H, quin), 1.97–2.11 (2H, m), 1.58–1.81 (6H, 2×m) ppm. LRMS (electrospray): m/z [M–H]$^+$ 223, [2M–H]$^+$ 447. Anal. Found C, 56.12; H, 7.39; N, 27.55. $C_9H_{12}N_4O_3$. 0.2 mol acetone requires C, 56.01; H, 7.44; N, 27.22%.

Preparation 31

4-Amino-5-cyclopentyl-1H-pyrazol-3-carboxylic Acid Amide.

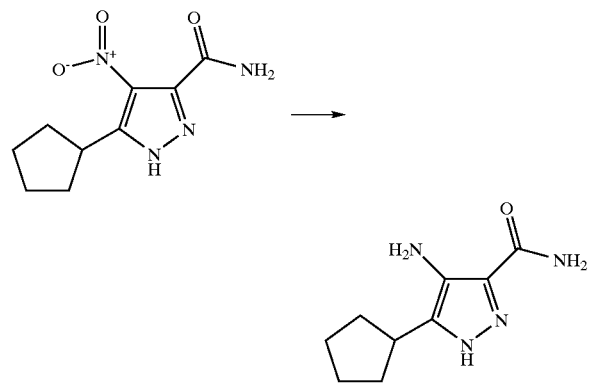

5-cyclopentyl-4-nitro-1H-pyrazol-3-carboxylic acid amide (4.48 g, 20 mmol) and 10% palladium on carbon (800 mg) in ethanol (50 ml) were stirred under hydrogen (50 psi) at room temperature for 18 hours. The reaction mixture was filtered through arbocel and the solid was washed with ethanol (50 ml), methanol (50 ml), dichloromethane (50 ml), and ethyl acetate (50 ml). The filtrate was concentrated under reduced pressure and the residue was purified by flash column chromatography on silica gel eluting with dichloromethane:methanol (9:1, by volume) to give 4-amino-5-cyclopentyl-1H-pyrazol-3-carboxylic acid amide (4.0 g) as an off-white solid which was a mixture of rotamers. $^1$H NMR (400 MHz, DMSO-D6): δ=12.20–12.31 (0.75H, brs), 11.78–11.87 (0.25H, brs), 7.02–7.18 (1.5H, brs), 6.80–6.93 (0.5H, brs), 4.22–4.56 (2H, 2×brs), 2.92–3.02 (1.96 2H, m), 1.48–1.78 (6H, 2×m) ppm. LRMS (electrospray): m/z [M–H]$^+$ 193. Anal. Found C, 56.12; H, 7.39; N, 27.55. $C_9H_{14}N_4O$. 0.2 mol acetone requires C, 56.01; H, 7.44; N, 27.22%.

Preparation 32

(3-Benzyloxy-phenyl)-acetic Acid Benzyl Ester.

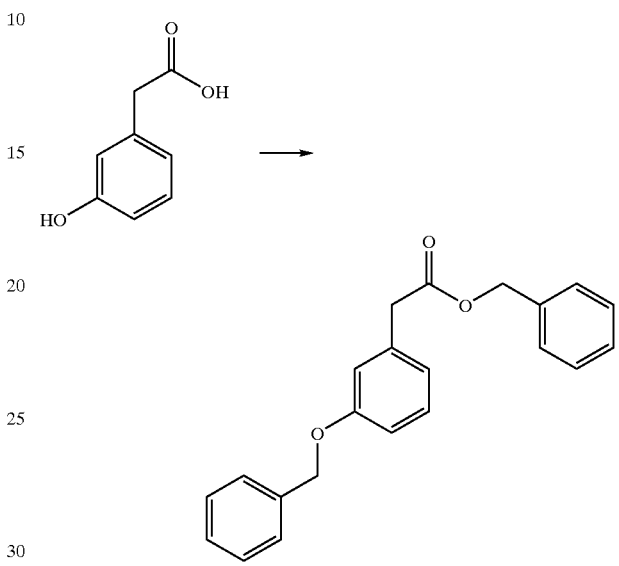

3-Hydroxy-phenyl-acetic acid (15.3 g, 101 mmol), benzyl bromide (36.2 g, 202 mmol) and potassium carbonate (29.2 g, 202 mmol) were suspended in dimethylformamide (300 ml) and the reaction was heated to reflux under nitrogen for 44 hours. The reaction mixture was cooled, filtered and the filtrate was concentrated under reduced pressure. The residue was partitioned between ethyl acetate (200 ml) and water (200 ml), and the aqueous phase was extracted with ethyl acetate. (2×200 ml). The combined organic extracts were washed with brine (200 ml), dried over $Na_2SO_4$ and the solvent was removed under reduced pressure. The residue was purified by flash column chromatography on silica gel eluting with pentane: ethyl acetate (95:5, by volume) to give (3-benzyloxy-phenyl)-acetic acid benzyl ester (10.7 g) as a white solid.

Preparation 33

(3-Benzyloxy-phenyl)-acetic Acid.

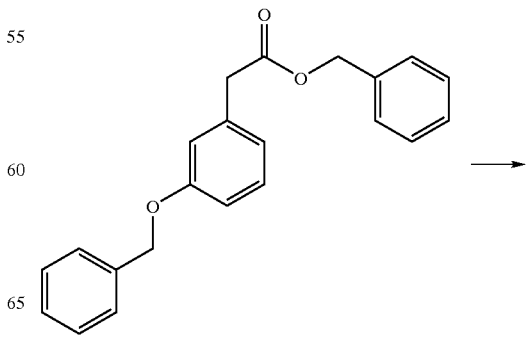

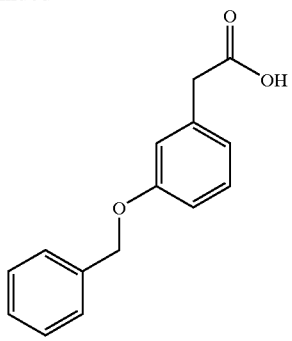

1N Sodium hydroxide solution (35 ml, 35 mmol) was added to a solution of (3-benzyloxy-phenyl)-acetic acid benzyl ester (5.3 g, 16 mmol) in methanol (350 ml) at room temperature under nitrogen. The reaction was heated to reflux for 2 hours, and the solvent was removed under reduced pressure. The residue was dissolved in water (500 ml) and extracted with ether (3×350 ml). The aqueous phase was acidified to pH 1 with concentrated hydrochloric acid and the resultant precipitate was isolated by filtration and dried under vacuum to give (3-benzyloxy-phenyl)-acetic acid (3.08 g) as a white solid. mp 127–129° C. $^1$H NMR (400 MHz, CDCl$_3$): δ=7.26–7.43 (5H, m), 7.20–7.26 (1H, m, partially masked by solvent), 6.84–6.96 (3H, m+s), 5.04 (2H, s), 3.62 (2H, s) ppm. LRMS (electrospray): m/z [M−H]$^+$ 241. Anal. Found C, 74.21; H, 5.82. C$_{15}$H$_{14}$O requires C, 74.36; H, 5.82%.

Preparation 34
(4-hydroxy-3-methoxy-phenyl)-acetic Acid Methyl Ester.

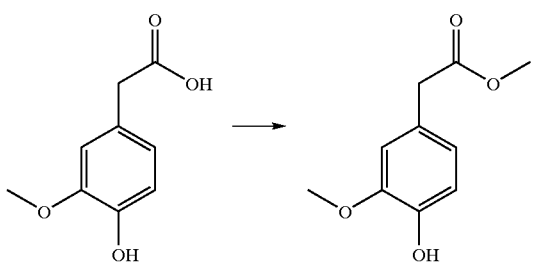

Concentrated sulfuric acid (12 ml) was added to a solution of (4-hydroxy-3-methyoxy-phenyl)-acetic acid (22.5 g, 123 mmol) in methanol (450 ml) at room temperature, and the reaction was heated to 90° C. for 2.45 hours. The reaction was then cooled to room temperature and stirred for 18 hours, and the solvent was removed under reduced pressure. The residue was suspended in ice water (300 ml) and extracted with diethylether (2×300 ml). The combined organic extracts were washed with saturated sodium bicarbonate solution (2×100 ml), brine (100 ml), dried over Na$_2$SO$_4$ and concentrated under reduced pressure. The residue was purified by flash column chromatography on silica gel eluting with a solvent gradient of cyclohexane:ethyl acetate (80:20 changing to 70:30, 60:40 and finally 1:1, by volume) to give (4-hydroxy-3-methoxy-phenyl)-acetic acid methyl ester (23 g) as a yellow oil. $^1$H NMR (400 MHz, CDCl$_3$): δ=6.82–6.85 (1H, d), 6.80 (1H, s), 6.76–6.79 (1H, d), 5.49 (1H 3.66 (3H, s), 3.53 (2H, s) ppm. LRMS (electrospray): m/z [M+Na]$^+$ 219.

Preparation 35
(4-Cyclopentyloxy-3-methoxy-phenyl)-acetic Acid Methyl Ester.

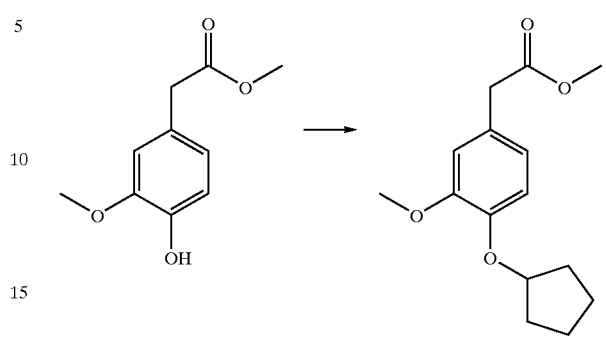

Cyclopentanol (7.7 ml, 85 mmol) and triphenylphosphine (28 g, 107 mmol) were added to a solution of (4-hydroxy-3-methyoxy-phenyl)-acetic acid methyl ester (14 g, 71 mmol) in tetrahydrofuran (280 ml) under nitrogen at 0° C. Diethylazodicarboxylate (15.7 ml, 100 mmol) was then added dropwise and the reaction was allowed to warm to room temperature and stirred for 44 hours. The solvent was removed under reduced pressure, pentane (200 ml) was added and the suspension was filtered. The filtrate was concentrated under reduced pressure and purified by flash column chromatography on silica gel eluting with a solvent gradient of cyclohexane:ethyl acetate (90:10 changing to 85:15, by volume) to give (4-cyclopentyloxy-3-methoxy-phenyl)-acetic acid methyl ester (12.4 g) as a colourless oil. $^1$H NMR (400 MHz, CD$_3$OD): δ=6.79–6.85 (2H, m), 6.73–6.79 (1H, d), 4.73–4.79 (1H, brs), 3.79 (3H, s), 3.64 (3H, s), 3.53 (2H, s), 1.74–1.89 (6H, m), 1.56–1.67 (2H, m) ppm. LRMS (electrospray): m/z [M+Na]$^+$ 287. Anal. Found C, 68.01; H, 7.74. C$_{15}$H$_{20}$O$_4$ requires C, 68.16; H, 7.63%.

Preparation 36
(4-Cyclopentyloxy-3-methoxy-phenyl)-Acetic Acid.

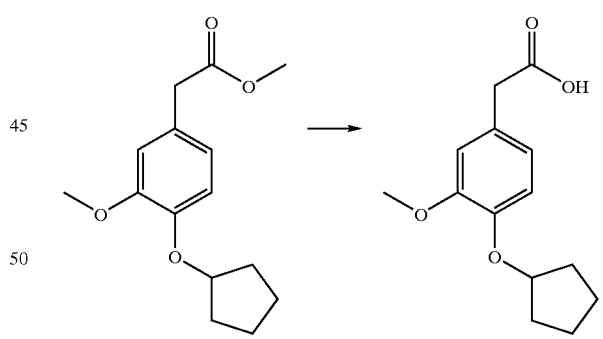

Sodium hydroxide (4.75 g, 119 mmol) was added to a solution of (4-cyclopentyloxy-3-methoxy-phenyl)-acetic acid methyl ester (12.4, 46.9 mmol) in methanol) 100 ml)/water (100 ml) and the reaction was stirred at room temperature for 3.5 hours. The methanol was removed under reduced pressure and the aqueous phase was washed with diethylether (100 ml) then acidified to pH 2 using concentrated hydrochloric acid. This was then extracted with ethyl acetate (2×200 ml) and the combined organic extracts were washed with brine (100 ml), dried over Na$_2$SO$_4$ and concentrated under reduced pressure to give (4-cyclopentyloxy-3-methoxy-phenyl)-acetic acid (11.1 g) as a white solid. $^1$H NMR (400 MHz, CD$_3$OD): δ=6.87 (1H, s), 6.81–6.86 (1H, d), 6.76–6.80 (1H, d), 4.75–4.79 (1H, brs), 3.78 (3H, s), 3.49 (2H, s), 1.71–1.89 (6H, m), 1.56–1.64 (2H, m) ppm. LRMS (electrospray): m/z [M–H]$^+$ 249, [2M–H]$^+$ 499. Anal. Found C, 67.15; H, 7.25. $C_{14}H_{18}O_4$ requires C, 67.18; H, 7.25%.

Preparation 37

2,4-Dimethyl-phenyl-acetic Acid.

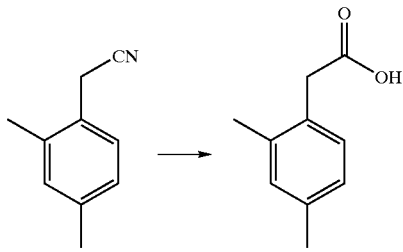

2,4-Dimethylbenzylcyanide (70 g, 0.48 mol) was mixed with water (134 ml) and concentrated sulfuric acid (106 ml, 1.98 mol) was added slowly. The reaction was heated to reflux for 3 hours, then cooled to room temperature over 18 hours. The mixture was poured onto crushed ice (500 ml), stirred for one hour and the resulting precipitate was isolated by filtration. After washing with water the solid was dissolved in 1.2M sodium hydroxide solution (500 ml), extracted with dichloromethane (2×250 ml) and the aqueous phase was treated with decolourising carbon (2 g) at reflux for 10 min and filtered hot through hyflo supercel. The filtrate was then acidified with concentrated hydrochloric acid and the resulting precipitate was isolated by filtration, washed with water and dried under vacuum to give 2,4-dimethyl-phenyl-acetic acid (52.6 g) as a white solid. $^1$H NMR (250 MHz, CD$_3$OD/D$_2$O): δ=6.88–7.03 (3H, m), 3.48–3.68 (2H, s), 2.23 (6H, s), ppm.

Preparation 38

Benzene Sulfonic Acid 2-chloro-ethyl Ester.

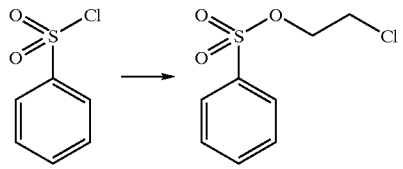

2-Chloroethanol (1168 g, 975 mol) and benzene sulfonyl chloride (2780 g, 2015 mol) were stirred together at −5° C. and pyridine (2158 g, 2200 mol) was added over a 3 hours period, maintaining the temperature below 0° C. The reaction was stirred for a further 3 hours at −5° C. to 0° C. and was then allowed to warm to room temperature over 18 hours. After pouring into a mixture of ice (10 liters) and water (10 liters) the reaction was stirred for 15 minutes, extracted with ether (10 liters) and the organic phase was washed with 5N HCl (2×2 liters) and water (2×4 liters). It was then dried over MgSO$_4$ and concentrated under reduced pressure to give benzene sulfonic acid 2-chloro-ethyl ester (1921 g) as an orange oil. $^1$H NMR (250 MHz, CDCl$_3$): δ=7.78–8.02 (2H, m), 7.58–7.78 (3H, m), 420–4.45 (2H, t), 3.60–3.81 (2H, t) ppm.

Preparation 39

2-Hydroxy-phenyl-acetic Acid Ethyl Ester.

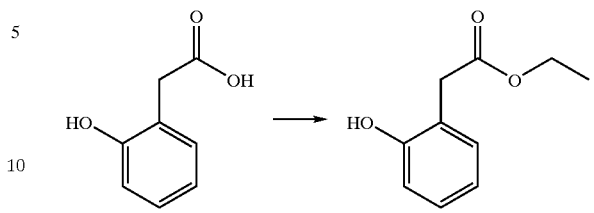

2-Hydroxy-phenyl-acetic acid (30.4 g, 0.2 mol) was dissolved in chloroform (200 ml) and thionyl chloride (50 ml, 0.2 mol) was added. The reaction was gently refluxed for 2 hours, upon which the mixture was concentrated under reduced pressure. The residue was slowly poured into ethanol (200 ml) maintaining a temperature of 10° C. to 20° C. The solvent was removed under reduced pressure and the residue was purified by thermal distillation to give 2-hydroxy-phenyl-acetic acid ethyl ester (31.6 g) as a yellow oil. Bp 146–150° C. $v_{max}$ (thin film) 1710 cm$^{-1}$ (C=O, ester).

Preparation 40

[2-(2-Chloro-ethoxy)-phenyl]-acetic Acid Ethyl Ester.

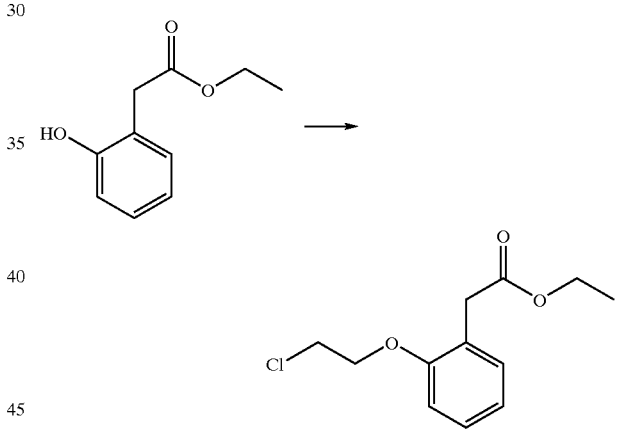

50% Sodium hydride in mineral oil (8.11 g, 169 mmol) was added portionwise to a solution of 2-hydroxy-phenyl-acetic acid ethyl ester (30.4 g, 169 mmol) in dimethylformamide (100 ml). After the initial effervescence had ended the reaction was heated to 100° C. for 10 minutes and was cooled to room temperature. A solution of benzene sulfonic acid 2-chloro-ethyl ester (37.2 g, 169 mmol) in dimethylformamide (5 ml) was then added and the reaction was heated to 100° C. for one hour, and allowed to cool to room temperature over 18 hours. The reaction mixture was partitioned between diethylether (300 ml) and water (300 ml) and the organic phase was removed and washed with water (100 ml), dried over MgSO$_4$ and the solvent was removed under reduced pressure. The residue was purified by thermal distillation to give [2-(2-chloro-ethoxy)-phenyl]-acetic acid ethyl ester (22.0 g) as a pale yellow oil. Bp 170° C. to 180° C. $v_{max}$ (thin film) 1735 cm$^{-1}$ (C=O, ester); no O—H stretch. Anal. Found C, 59.35; H, 6.29. $C_{12}H_{15}ClO_3$ requires C, 59.38; H, 6.23%.

Preparation 41
[2-(2-Imidazol-1-yl-ethoxy)-phenyl]-acetic Acid.

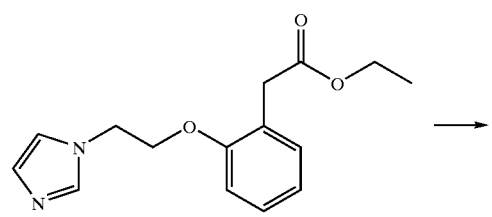

[2-(2-Imidazol-1-yl-ethoxy)-phenyl]-acetic acid ethyl ester (3.5 g, 113 mmol) was stirred in 50% aqueous hydrochloric acid (20 ml) at 100° C. for 6 hours. After cooling to room temperature the solvent was removed under reduced pressure and the residue was recrystallised from isopropylalcohol to give [2-(2-Imidazol-1-yl-ethoxy)-phenyl]-acetic acid (2.73 g) as a white solid. Mp 146–147° C. $\nu_{max}$ (thin film) 3410 (O—H), 1722 cm$^{-1}$ (C=O, acid). Anal. Found C, 54.89; H, 5.25; N, 9.80. $C_{13}H_{14}N_2O_3$. 1 mol HCl requires C, 55.22; H, 5.35; N, 9.91%.

Preparation 42
5-Cyclopentyl-4-[2-(2-trifluoromethoxy-phenyl)-acetylamino]-1H-pyrazole-3-carboxylic Acid Amide.

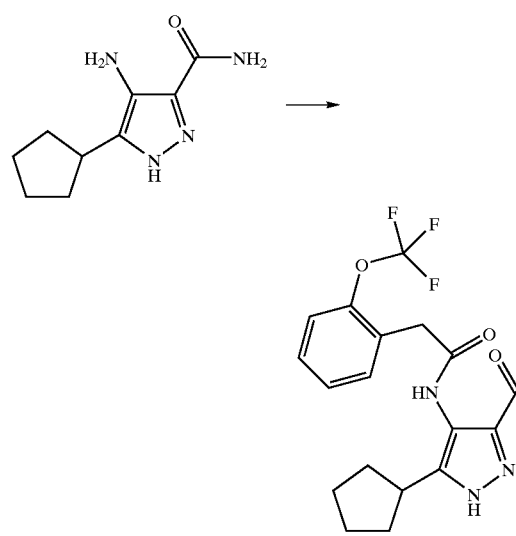

Carbonyldiimidazole (84 mg, 0.515 mmol) was added to a solution of 2-triflouoromethyoxy-phenyl-acetic acid (113 mg, 0.515 mmol) in tetrahydrofuran (4 ml) under nitrogen at room temperature, and the mixture was stirred for 3 hours. 4-Amino-5-cyclopentyl-1H-pyrazol-3-carboxylic acid amide (100 mg, 0.515 mmol) was then added and the reaction was stirred for 18 hours. The reaction mixture was diluted with water (20 ml), acidified to pH 2 with 2N HCl and extracted with ethyl acetate (2×20 ml). The combined organic extracts were dried over MgSO$_4$ and concentrated under reduced pressure to give 5-cyclopentyl-4-[2-(2-trifluoromethoxy-phenyl)-acetylamino]-1H-pyrazole-3-carboxylic acid amide (120 mg) as an off-white solid. LRMS (electrospray): m/z [M+H]$^+$ 397, [M–H]$^+$ 395.

Preparation 43
5-Isobutyl-4-[2-(2-trifluoromethoxy-phenyl)-acetylamino]-1H-pyrazole-3-carboxylic Acid Amide.

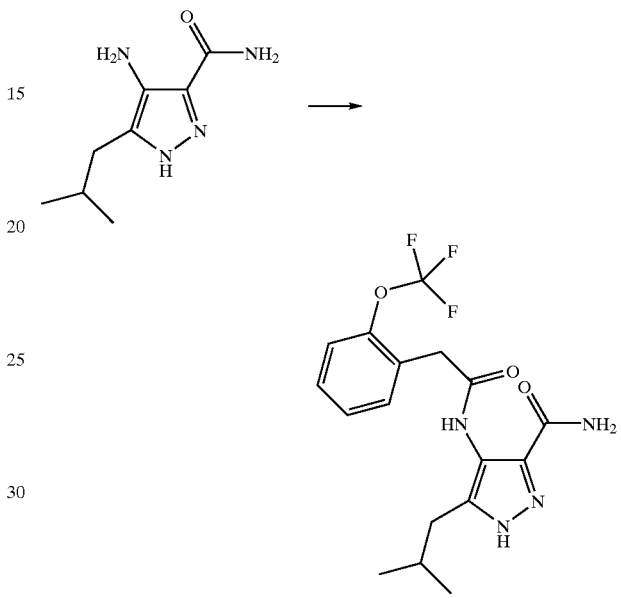

Carbonyldiimidazole (84 mg, 0.515 mmol) was added to a solution of 2-triflouoromethyoxy-phenyl-acetic acid (113 mg, 0.515 mmol) in tetrahydrofuran (4 ml) under nitrogen at room temperature, and the mixture was stirred for 3 hours. 4-Amino-5-isobutyl-1H-pyrazol-3-carboxylic acid amide (100 mg, 0.515 mmol) was then added and the reaction was stirred for 18 hours. The reaction mixture was diluted with water (20 ml), acidified to pH 2 with 2N HCl and extracted with ethyl acetate (2×20 ml). The combined organic extracts were dried over MgSO$_4$ and concentrated under reduced pressure to give 5-isobutyl-4-[2-(2-trifluoromethoxy-phenyl)-acetylamino]-1H-pyrazole-3-carboxylic acid amide (142 mg) as an off-white solid. LRMS (electrospray): m/z [M+H]$^+$ 385, [M–H]$^+$ 383.

Preparation 44
5-Pyridine-3-yl-4-[2-(2-trifluoromethoxy-phenyl)-acetylamino]-1H-pyrazole-3-carboxylic Acid Amide.

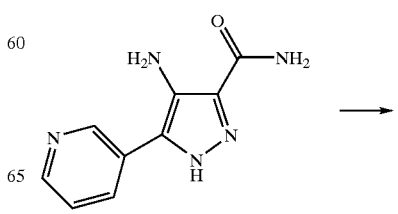

-continued

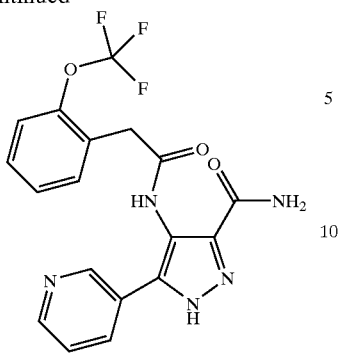

Carbonyldiimidazole (144 mg, 0.886 mmol) was added to a solution of 2-triflouoromethyoxy-phenyl-acetic acid (195 mg, 0.886 mmol) in tetrahydrofuran (5 ml) under nitrogen at room temperature, and the mixture was stirred for one hour. 4-Amino-5-cyclopropyl-1H-pyrazol-3-carboxylic acid amide (180 mg, 0.886 mmol) was then added and the reaction was stirred for 18 hours. The reaction mixture was diluted with brine (20 ml) and extracted with ethyl acetate (2×20 ml). The combined organic extracts were dried over MgSO$_4$ and concentrated under reduced pressure to give 5-pyridine-3-yl-4-[2-(2-trifluoromethoxy-phenyl)-acetylamino]-1H-pyrazole-3-carboxylic acid amide (345 mg) as an off-white solid. LRMS (electrospray): m/z [M+Na]$^+$ 428, [M−H]$^+$ 404.

What is claimed is:

1. A method of treating insulin resistance syndrome in a mammal comprising administering to said mammal a cGMP PDE9 inhibitor, or a pharmaceutically acceptable salt thereof, or a solvate of said inhibitor or of said salt.

2. A method of claim 1 wherein said cGMP PDE9 inhibitor is a compound of the formula (I)

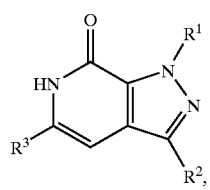

(I)

or a pharmaceutically acceptable salt thereof, or a solvate of said compound or of said salt, wherein:

$R^1$ is H or (C$_1$–C$_6$)alkyl;

$R^2$ is (C$_1$–C$_6$)alkyl, straight chain or branched chain, (C$_3$–C$_7$)cycloalkyl or heteroaryl;

$R^3$ is (C$_1$–C$_6$)alkyl, straight chain or branched chain, optionally substituted by 1–2 groups each independently selected from Ar, (C$_3$–C$_7$)cycloalkyl, OAr, SAr, NC(O)(C$_1$–C$_6$)alkyl, heteroaryl, xanthene, and naphthalene;

Ar is a group of formula

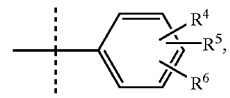

wherein $R^4$, $R^5$ and $R^6$ are each independently selected from H, halo, phenoxy, phenyl, CF$_3$, OCF$_3$, S(C$_1$–C$_6$)alkyl, (C$_1$–C$_6$)alkyl, O(C$_1$–C$_6$)alkyl, said alkyl optionally substituted by a heteroaryl group or by a phenyl group, wherein said phenyl group is optionally substituted by 1–3 groups selected from halo, CF$_3$, OCF$_3$ and (C$_1$–C$_6$)alkyl; or wherein $R^4$ and $R^5$ may combine to form a (C$_2$–C$_3$)alkyl link, wherein said link may optionally incorporate a heteroatom selected from O, S and N; and heteroaryl is aromatic 5–6 membered heterocycle containing 1–3 heteroatoms, each independently selected from O, S and N, said heterocycle optionally substituted by 1–3 substituents, each independently selected from (C$_1$–C$_6$)alkyl, halo and phenyl, said phenyl optionally substituted by 1–3 groups selected from halo and (C$_1$–C$_6$)alkyl; with the proviso that when $R^1$ is —CH$_3$, $R^2$ cannot be —CH$_2$CH$_2$CH$_3$.

3. A method of claim 2 wherein $R^1$ is H or CH$_3$; $R^2$ is (C$_3$–C$_4$)alkyl, cyclopentyl or pyridinyl; $R^3$ is (C$_1$–C$_3$)alkyl, optionally substituted by 1–2 groups selected from Ar, (C$_3$C$_7$)cycloalkyl and heteroaryl; $R^4$, $R^5$ and $R^6$ are each independently selected from H, halo, phenoxy, phenyl, CF$_3$, OCF$_3$, S(C$_1$–C$_6$)alkyl, (C$_1$–C$_6$)alkyl, O(C$_1$–C$_6$)alkyl; said alkyl in the definition of $R^4$, $R^5$ and $R^6$ is optionally substituted by a heteroaryl group or by a phenyl group optionally substituted by 1–3 groups selected from halo, CF$_3$, OCF$_3$ and (C$_1$–C$_6$)alkyl; or wherein $R^4$ and $R^5$ may combine to form a C$_2$ alkyl link, said link incorporating an O atom; and heteroaryl is an aromatic 5–6 membered heterocycle containing at least 2 nitrogen atoms, said heterocycle optionally substituted by 1–3 substituents, each independently selected from (C$_1$–C$_6$)alkyl, halo and phenyl, said phenyl in the definition of heterocycle optionally substituted by 1–3 groups selected from halo and (C$_1$–C$_6$)alkyl.

4. A method of claim 1 comprising administering to said mammal 5-(3-chloro-benzyl)-3-isopropyl-1,6-dihydro-pyrazolo[4,3-d]pyrimidin-7-one, or a pharmaceutically acceptable salt thereof.

* * * * *